United States Patent
Moreno et al.

(10) Patent No.: US 8,614,243 B2
(45) Date of Patent: Dec. 24, 2013

(54) SMALL-MOLECULE MODULATORS OF TRP-P8 ACTIVITY

(75) Inventors: Ofir Moreno, Seattle, WA (US); Sateesh Natarajan, Bellevue, WA (US); David F. Duncan, San Diego, CA (US)

(73) Assignee: Dendreon Corporation, Seattle, WA (US)

( * ) Notice: Subject to any disclaimer, the term of this patent is extended or adjusted under 35 U.S.C. 154(b) by 403 days.

(21) Appl. No.: 12/796,587

(22) Filed: Jun. 8, 2010

(65) Prior Publication Data

US 2012/0225871 A1 Sep. 6, 2012

Related U.S. Application Data

(63) Continuation of application No. 11/707,546, filed on Feb. 15, 2007, now Pat. No. 7,741,355.

(60) Provisional application No. 60/773,435, filed on Feb. 15, 2006.

(51) Int. Cl.
| | | |
|---|---|---|
| *A61K 31/415* | (2006.01) | |
| *A61K 31/4155* | (2006.01) | |
| *C07D 401/14* | (2006.01) | |
| *C07D 231/40* | (2006.01) | |

(52) U.S. Cl.
USPC ............... 514/407; 548/364.1; 548/365.7; 548/371.7

(58) Field of Classification Search
None
See application file for complete search history.

(56) References Cited

U.S. PATENT DOCUMENTS

| | | |
|---|---|---|
| 3,821,221 A | 6/1974 | Podesva et al. |
| 4,020,153 A | 4/1977 | Rosell et al. |
| 4,150,052 A | 4/1979 | Watson et al. |
| 4,153,679 A | 5/1979 | Rowsell et al. |
| 4,248,859 A | 2/1981 | Rowsell et al. |
| 4,296,093 A | 10/1981 | Rowsell et al. |
| 4,459,425 A | 7/1984 | Amano et al. |
| 5,266,592 A | 11/1993 | Grub et al. |
| 5,756,857 A | 5/1998 | Kuribayashi et al. |
| 6,328,982 B1 | 12/2001 | Shiroyama et al. |
| 6,497,859 B1 | 12/2002 | Zanone et al. |
| 2004/0001801 A1 | 1/2004 | Madison |
| 2005/0054651 A1 | 3/2005 | Natarajan |
| 2005/0084447 A1 | 4/2005 | Wei |
| 2007/0232603 A1 | 10/2007 | Moreno et al. |

FOREIGN PATENT DOCUMENTS

| | | |
|---|---|---|
| EP | 1 121 927 A2 | 8/2001 |
| EP | 1 157 617 A2 | 11/2001 |
| JP | 2000-247910 A | 9/2000 |
| WO | WO 93/23005 A1 | 11/1993 |
| WO | WO 93/25177 A1 | 12/1993 |
| WO | WO 02/095007 A2 | 11/2002 |
| WO | WO 02/095007 A3 | 11/2002 |
| WO | WO 2005/002582 A2 | 1/2005 |
| WO | WO 2005/002582 A3 | 1/2005 |
| WO | WO 2005/020897 A2 | 3/2005 |
| WO | WO 2005/020897 A3 | 3/2005 |
| WO | WO 2005/070460 A2 | 8/2005 |
| WO | WO 2005/070460 A3 | 8/2005 |
| WO | 2006/125334 A1 | 11/2006 |
| WO | WO 2007/095340 A2 | 8/2007 |
| WO | WO 2007/095340 A3 | 8/2007 |

OTHER PUBLICATIONS

Bardyshev, I.I. et al., "Synthesis and pesticide activity of some amino derivatives of terpenoids," *Vesti Akademii Navuk BSSR, Seryya Khimichnykh Navuk*, 1984, vol. 4, pp. 89-91, Abstract only.

Barren III, R.J. et al., "Monoclonal Antibody 7E11.C5 Staining of Viable LNCaP Cells," *The Prostate*, 1997, vol. 30, pp. 65-68.

Barry, M.J. et al., "Measuring the Symptoms and Health Impact of Benign Prostatic Hyperplasia and its Treatments," *Benign Prostatic Hyperplasia, 5th International Consultation on Benign Prostatic Hyperplasia (BPH)*, C. Chatelain et al., eds., Jun. 25-28, 2000, Paris, Health Publication, Ltd, 2001, pp. 203-225.

Beck, B. et al., "Prospects for prostate cancer imaging and therapy using high-affinity TRPM8 activators," *Cell Calcium*, 2007, vol. 41, pp. 285-294.

Bödding, M. et al., "Characterisation of TRPM8 as a pharmacophore receptor," *Cell Calcium*, 2007, vol. 42, pp. 618-628.

Clapham, D.E. et al., "The TRP Ion Channel Family," *Nature Reviews*, Jun. 2001, vol. 2, pp. 387-396.

Clapham, D.E., "Hot and Cold TRP Ion Channels," *Science*, Mar. 22, 2002, vol. 295, pp. 2228-2229.

Clapham, D.E. et al., *Transient Receptor Potential Channels, The IUPHAR Ion Channel Compendium*, IUPHAR Media, Communications Division of the International Union of Pharmacology, 2002, Royston: United Kingdom, pp. 209-235.

Correale, P. et al., "Generation of Human Cytolytic T Lymphocyte Lines Directed Against Prostate-Specific Antigen (PSA) Employing a PSA Oligoepitope Peptide," *The Journal of Immunology*, 1998, vol. 161, pp. 3186-3194.

(Continued)

*Primary Examiner* — Alicia L Otton
(74) *Attorney, Agent, or Firm* — Kilpatrick Townsend & Stockton LLP

(57) ABSTRACT

Provided are small-molecule Trp-p8 modulators, including Trp-p8 agonists and Trp-p8 antagonists, and compositions comprising small-molecule Trp-p8 agonists as well as methods for identifying and characterizing novel small-molecule Trp-p8 modulators and methods for decreasing viability and/or inhibiting growth of Trp-p8 expressing cells, methods for activating Trp-p8-mediated cation influx, methods for stimulating apoptosis and/or necrosis, and related methods for the treatment of diseases, including cancers such as lung, breast, colon, and/or prostate cancers as well as other diseases, such as benign prostatic hyperplasia, that are associated with Trp-p8 expression.

10 Claims, 19 Drawing Sheets

(56) References Cited

OTHER PUBLICATIONS

Costello, L.C. et al., "Citrate in the Diagnosis of Prostate Cancer," *The Prostate*, 1999, vol. 38, pp. 237-245.
Costello, L.C. et al., "The Intermediary Metabolism of the Prostate: A Key to Understanding the Pathogenesis and Progression of Prostate Malignancy," *Oncology*, 2000, vol. 59, pp. 269-282.
Costello, L.C. et al., "Zinc causes a shift toward citrate at equilibrium of the m-aconitase reaction of prostate mitochondria," *Journal of Inorganic Biochemistry*, 2000, vol. 78, pp. 161-165.
Duncan, L.M. et al., "Down-Regulation of the Novel Gene *Melastatin* Correlates with Potential for Melanoma Metastasis," *Cancer Research*, Apr. 1, 1998, vol. 58, pp. 1515-1520.
Fuessel, S. et al., "Multiple tumor marker analyses (PSA, hK2, PSCA, trp-p8) in primary prostate cancers using quantitative RT-PCR," *International Journal of Oncology*, 2003, vol. 23, pp. 221-228.
Hoffman, T. et al., "Transient receptor potential channels as molecular substrates of receptor-mediated cation entry," *J. Mol. Med.*, 2000, vol. 78, pp. 14-25.
Horoszewicz, J.S. et al., "Monoclonal Antibodies to a New Antigen Marker in Epithelial Prostatic Cells and Serum of Prostatic Cancer Patients," *Anticancer Research*, 1987, vol. 7, pp. 927-935.
Hunter, J.J. et al., "Chromosomal Localization and Genomic Characterization of the Mouse Melastatin Gene (*Mlsn1*)," *Genomics*, 1998, vol. 54, pp. 116-123.
John Hopkins Medicine, "BPH (Benign Prostatic Hyperplasia)," *John Hopkins Medicine, Health Alerts*, accessed on May 26, 2009, at <http://www.johnshopkinshealthalerts.com/symtpoms_remedies/benign_prostatic_hyperplasia/2077-1.html>.
Kozolov, N.G. et al., "Reduction amination of 1-menthol by aliphatic nitriles," *Khimiya Prirodnykh Soedinenii*, 1981, vol. 3, pp. 312-317, abstract only.
McKemy, D.D. et al., "Identification of a cold receptor reveals a general role for TRP channels in thermosensation," *Nature*, Mar. 7, 2002, vol. 416, pp. 52-58.
Murphy, G.P. et al., "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement," *The Prostate*, 1995, vol. 26, pp. 164-168.
Murphy, G.P. et al., "Comparison of Serum PSMA, PSA Levels With Results of Cytogen-356 ProstaScint® Scanning in Prostatic Cancer Patients," *The Prostate*, 1997, vol. 33, pp. 281-285.
Murphy, G.P. et al., "Infusion of Dendritic Cells Pulsed With HLA-A2-Specific Prostate-Specific Membrane Antigen Peptides: A Phase II Prostate Cancer Vaccine Trial Involving Patients With Hormone-Refractory Metastatic Disease," *The Prostate*, 1999, vol. 38, pp. 73-78.
Nagamine, K. et al., "Molecular Cloning of a Novel Putative $Ca^{2+}$ Channel Protein (TRPC7) Highly Expressed in Brain," *Genomics*, 1998, vol. 54, pp. 124-131.
Nealen, M.L. et al., "TRPM8 mRNA Is Expressed in a Subset of Cold-Responsive Trigeminal Neurons From Rat," *J. Neurophysiol*, Jul. 2003, vol. 90, pp. 515-520.
Parker, S.L. et al., "Cancer Statistics, 1996," *CA Cancer J. Clin,.* Jan./Feb. 1996, vol. 46, No. 1, pp. 5-27.
Patani et al., "Bioisosterism: A Rational Approach in Drug Design," *Chem. Rev.*, 1996, vol. 96, pp. 3147-3176.
Peier, A.M. et al., "A TRP Channel that Senses Cold Stimuli and Menthol," *Cell*, Mar. 8, 2002, vol. 108, pp. 705-715.
Reid, G. et al., "A Cold- and menthol-activated current in rat dorsal root ganglion neurones: properties and role in cold transduction," *Journal of Physiology*, 2002, vol. 545.2, pp. 595-614.
Rochon, Y.P. et al., "Western Blot Assay for Prostate-Specific Membrane Antigen in Serum of Prostate Cancer Patients," *The Prostate*, 1994, vol. 25, pp. 219-223.
Swierzewski, S.J., III., "Urologic Emergencies: Acute Urinary Retention, Risk Factors, Causes, Treatment," Jun. 10, 1998, accessed on May 26, 2009, at: <http://www.urologychannel.com/emergencies/acute.shtml>.
Tsavaler, L. et al., "*Trp-p8*, a Novel Prostate-specific Gene, Is Up-Regulated in Prostate Cancer and Other Malignancies and Shares High Homology with Transient Receptor," *Cancer Research*, May 1, 2001, vol. 61, pp. 3760-3769.
Voisin, D. et al., "Stereochemical studies. X. Solvent effects on the optical activity of conformers and on conformational equilibrium," *Bulletin de la Societe Chimique de France*, 1971, vol. 7, pp. 2643-2651, Abstract only.

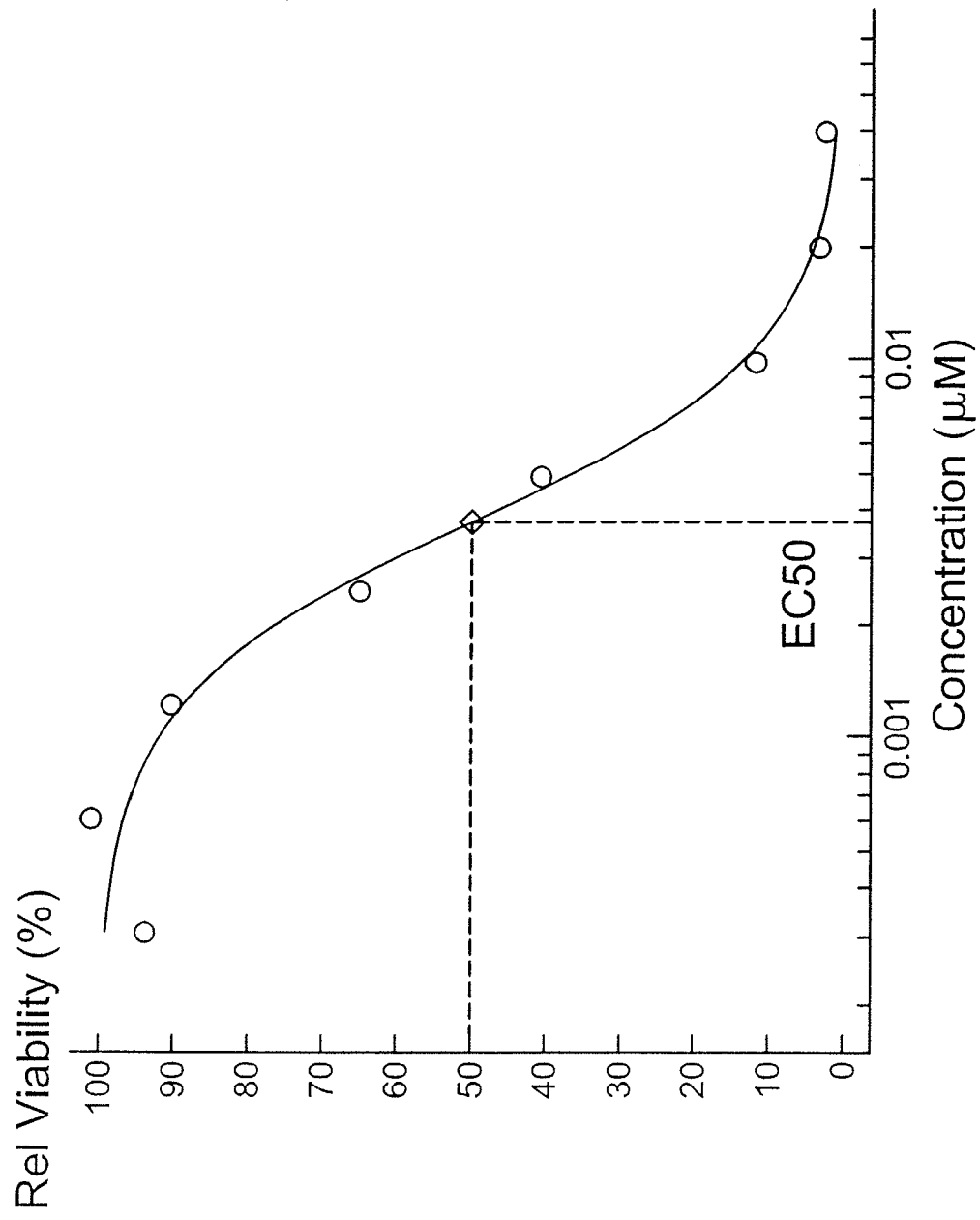

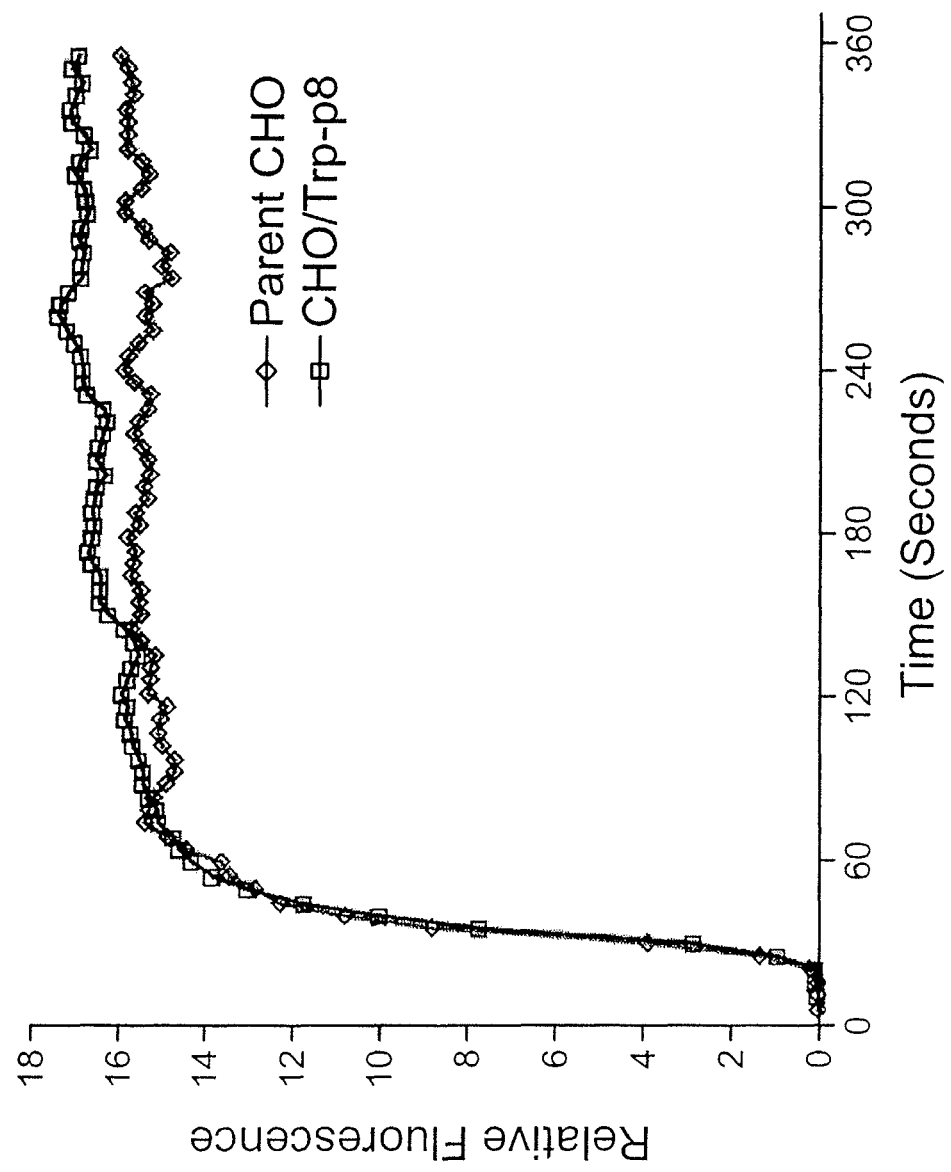

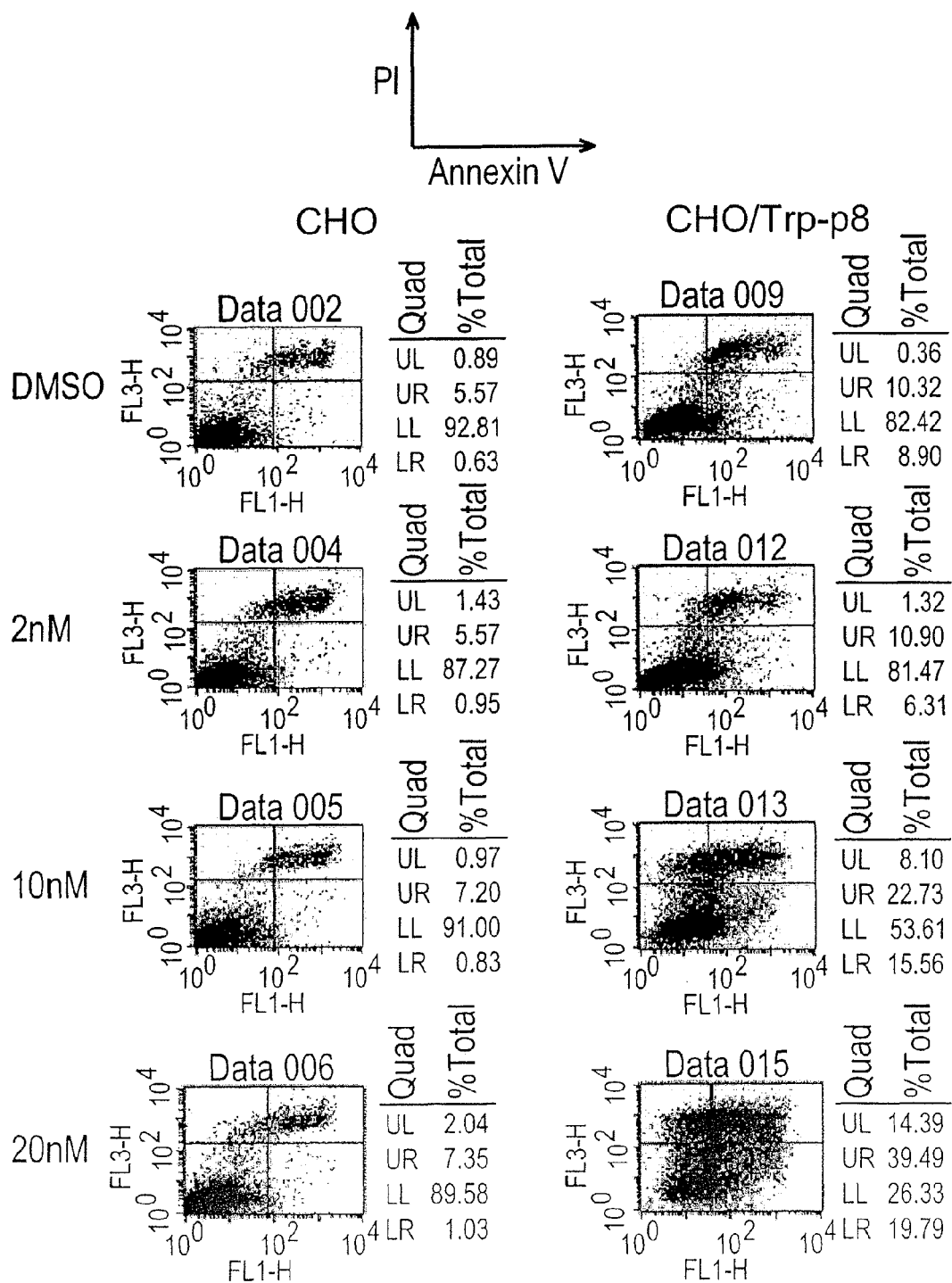

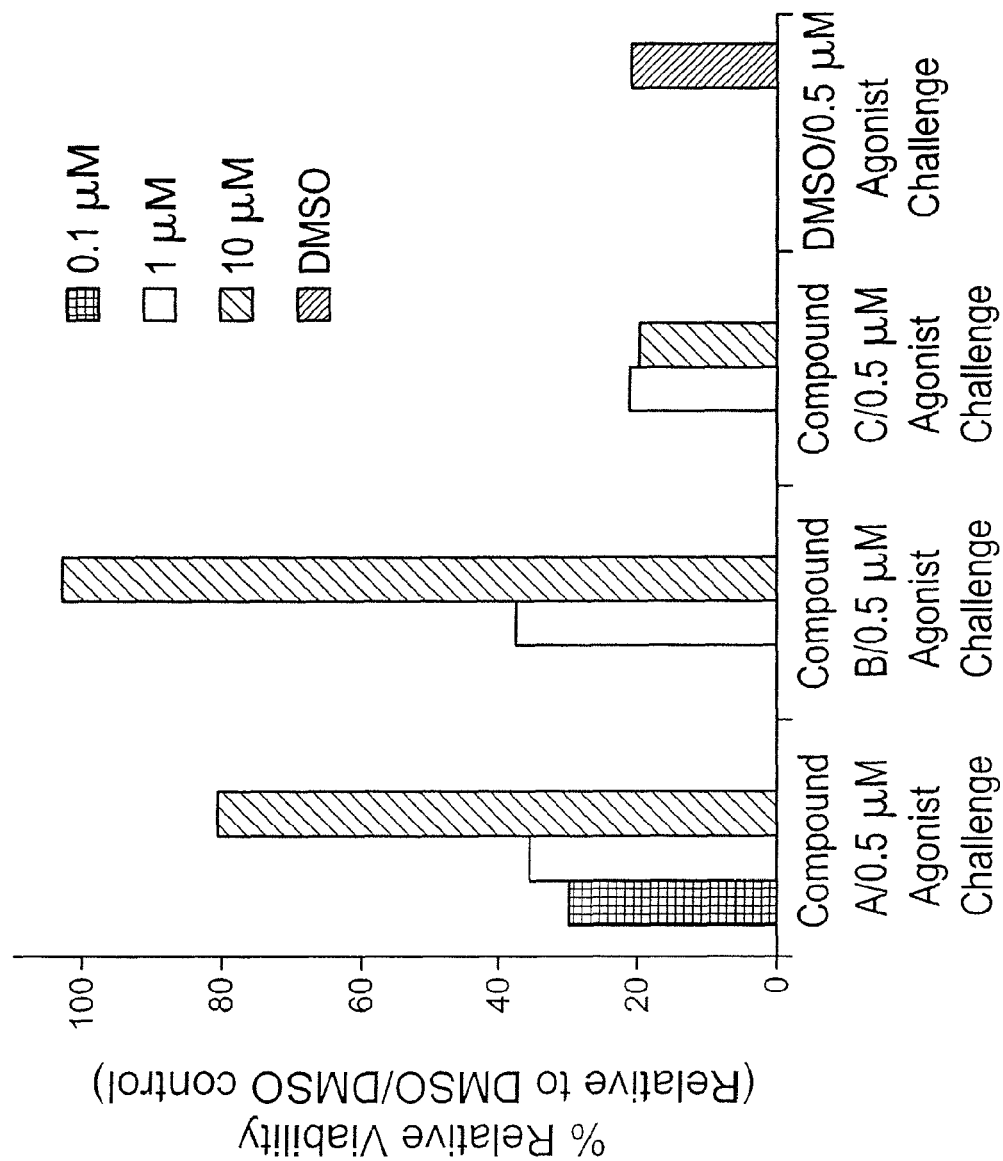

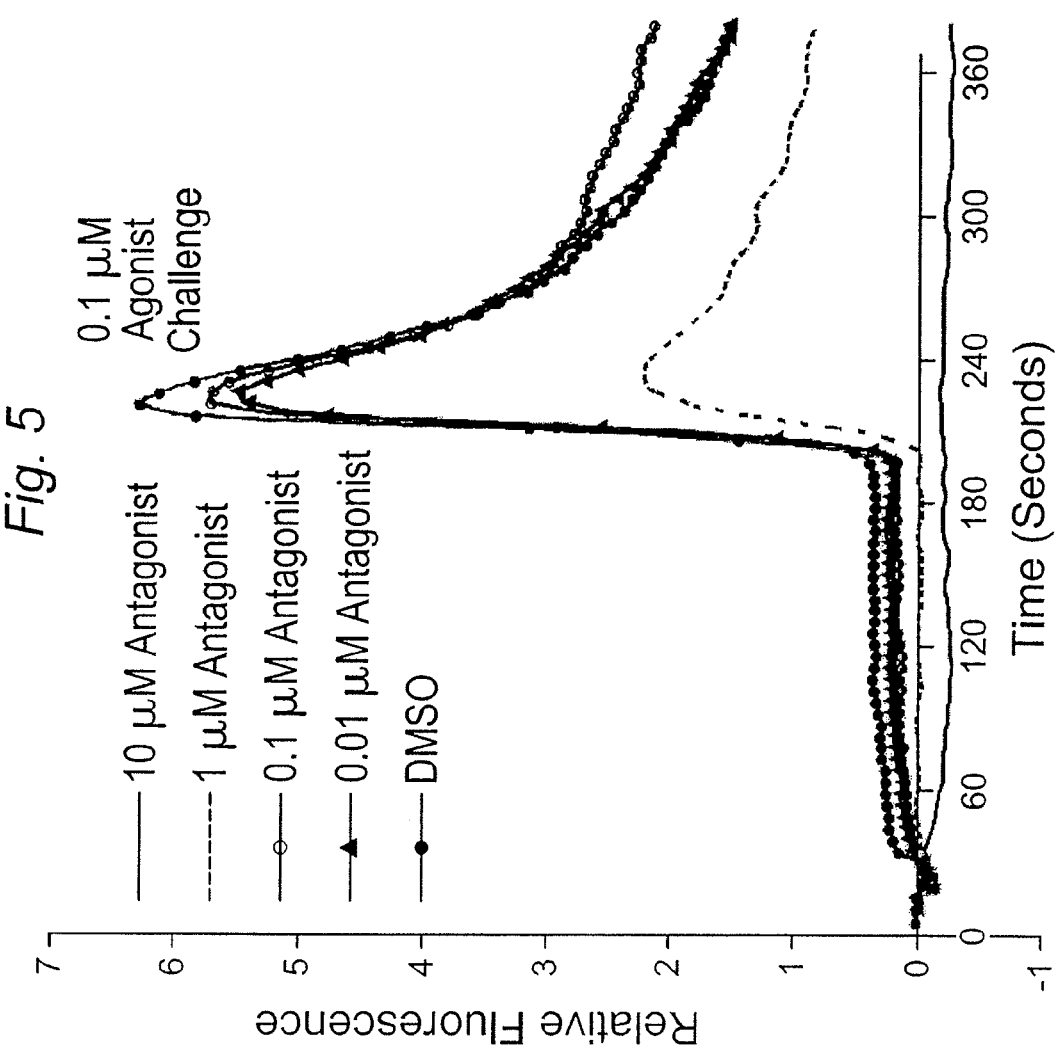

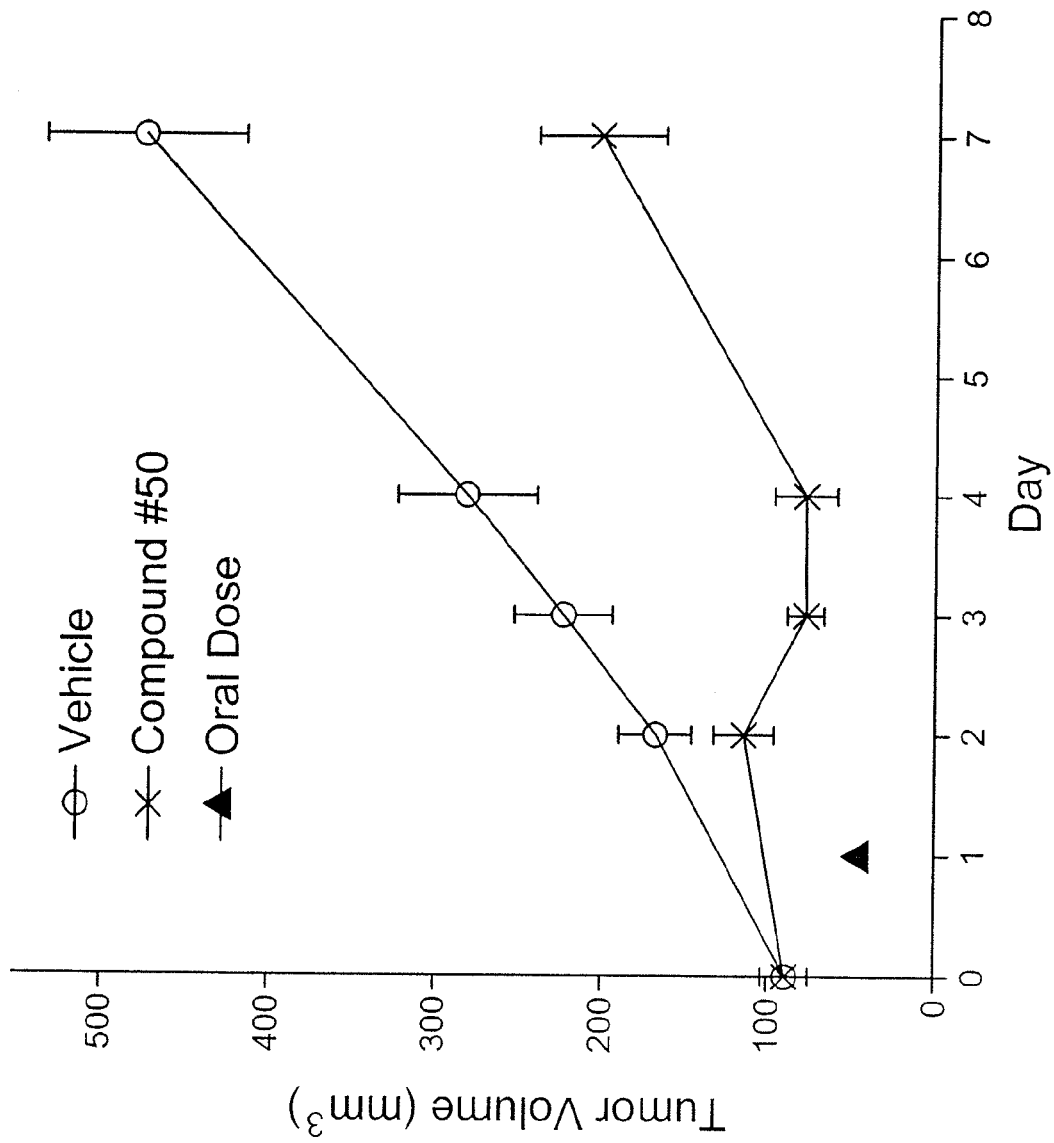

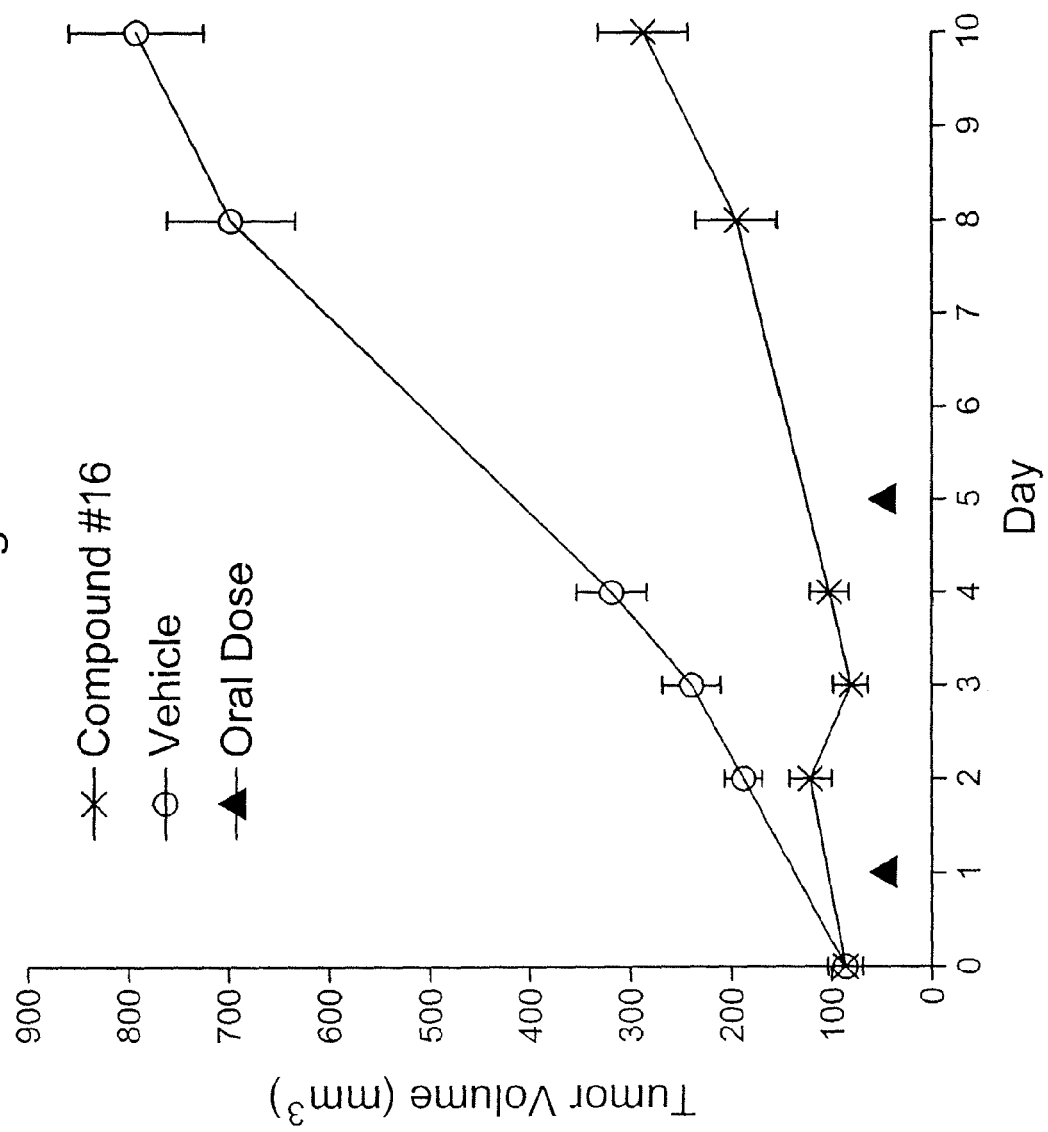

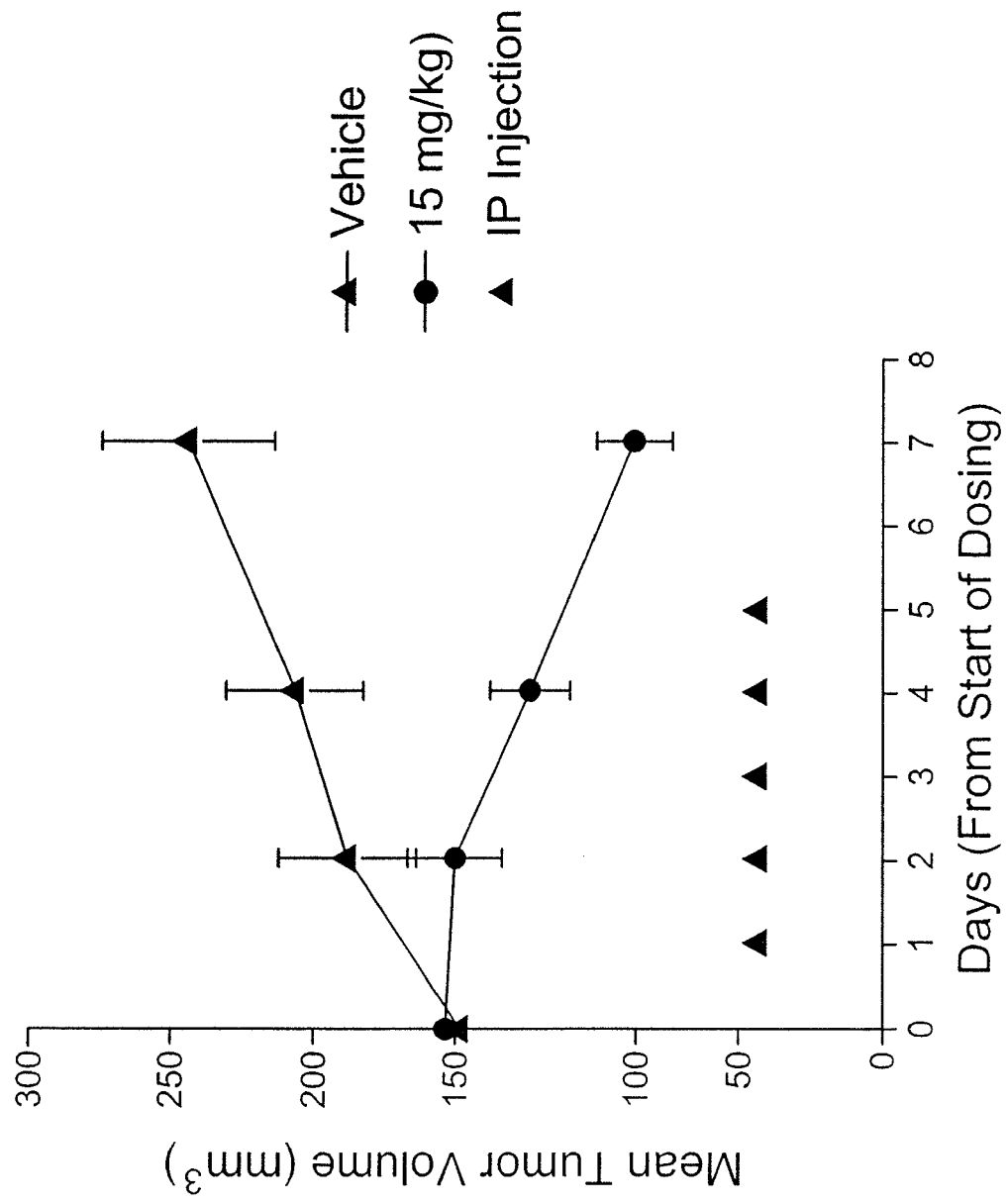

SMALL-MOLECULE MODULATORS OF TRP-P8 ACTIVITY

CROSS-REFERENCES TO RELATED APPLICATIONS

This application is a Continuation of U.S. Non-Provisional patent application Ser. No. 11/707,546 filed Feb. 15, 2007 which claims the benefit of priority under 35 U.S.C. §119(e) to U.S. Provisional Patent Application No. 60/773,435 filed on Feb. 15, 2006; the contents of each are incorporated herein by reference.

BACKGROUND OF THE INVENTION

The present invention relates generally to the fields of cell biology, biochemistry, and organic chemistry. More specifically, the present invention provides small-molecule modulators of Trp-p8 activity, which include Trp-p8 agonists and Trp-p8 antagonists, as well as compositions comprising small-molecule Trp-p8 modulators. Also provided are methods for identifying and characterizing novel small-molecule Trp-p8 modulators as well as methods for modulating Trp-p8-mediated cation influx and/or apoptosis in a cell and related methods for the treatment of diseases associated with Trp-p8 expression, activation, and/or signaling. Exemplary diseases suitably treated by the compositions and methods of the present invention include cancers, such as lung, breast, colon, and/or prostate cancers.

BACKGROUND OF THE INVENTION

Prostate carcinoma is the most common cancer diagnosed in men in the United States and has the second highest cancer death rate yielding only to lung adenocarcinoma. Parker et al., *CA Cancer J. Clin.* 46:5-27 (1996). Although it is possible to effectively treat organ-confined prostate cancer, there are very limited treatment options for metastatic disease. Thus, it is of great importance to find novel ways to diagnose early stage disease and to closely monitor both progression and treatment of the disease, as well as to develop new therapeutic approaches. To achieve this, it is important to understand the molecular mechanisms of prostate cancer development and to identify new biochemical markers for disease diagnosis and progression.

To date there are very few prostate-specific markers available. The best-known and well-characterized markers of proven prostate cancer diagnostic value are the proteins prostatic acid phosphatase (PAP), prostate specific antigen (PSA), and prostate-specific membrane antigen (PSMA). Each of these proteins has also become the target for novel immunotherapy approaches to the treatment of disease. Horoszewicz et al., *Anticancer Res.* 7:927-935 (1987); Barren et al., *Prostate* 30:65-68 (1997); Murphy et al., *Prostate* 33:281-285 (1997); Murphy et al., *Prostate* 26:164-168 (1995); Rochon et al., *Prostate* 25:219-223 (1995); Correale et al., *J. Immunol.* 161:3186-3194 (1998); and Murphy et al., *Prostate* 38:73-78 (1999).

It has been reported that a cation channel protein, variously designated Trp-p8 (transient receptor potential-p8), TRPM8, and CMR1 (cold and menthol receptor 1), is preferentially expressed in prostate. Cloning of the full-length human Trp-p8 cDNA revealed a transcript corresponding to an 1104 amino acid polypeptide sharing homology with the trp family of calcium channels. Clapham et al., *Nature Reviews* 2:387-396 (2001) and Clapham et al., IUPHAR Compendium, TRP Channels (2002). Trp-p8 shows particularly high homology with the human TRPC7 gene—a putative $Ca^{2+}$ channel protein of the trp family that is highly expressed in brain tissue. Nagamine et al., *Genomics* 54:124-131 (1998). Trp-p8 also shows significant homology to human melastatin, another Trp family-related protein expressed in melanocytes and believed to be a tumor suppressor gene. Duncan et al., *Cancer Res.* 58:1515-1520 (1998) and Hunter et al., *Genomics* 54:116-123 (1998). Perhaps of greatest interest is the observation that the Trp-p8 gene appears to be expressed in a large spectrum of nonprostatic, in addition to prostatic, neoplastic lesions. Tsavaler et al., *Cancer Res.* 61(9):3760-9 (2001).

The Trp superfamily comprises more than 20 related cation channel proteins that have been implicated in processes including sensory physiology to vasorelaxation and male fertility. Defects in Trp channels have been associated with changes in growth control and tumor suppression. While all Trp proteins are calcium channels, they vary significantly in their selectivity and mode of activation. Members of the Trp superfamily share significant sequence homology and predicted structural similarities, such as size of predicted transmembrane segments.

Trp-p8 is over-expressed in a range of cancers including prostate, breast, lung and colon, while within normal tissues, it is predominantly expressed in human prostate [Tsavaler et al., supra] and dorsal root ganglia (DRG), (Dendreon, unpublished observation). Fuessel et al. reported that Trp-p8 is a highly prostate-specific and prostate carcinoma-associated gene thus qualifying it as a potential target for specific therapies. *International J. of Oncology* 23:221-228 (2003). Among other species, Trp-p8 orthologues are reportedly expressed in a subset of DRG and trigeminal ganglia (TG) neurons in rat [McKemy et al., *Nature* 416(6876):52-8 (2002)] and mouse [Peier et al., *Cell* 108(5):705-15 (2002)] as well. Thus, Trp-p8 is a pantumor-expressed marker with significant potential use in disease diagnosis and monitoring of disease progression during treatment as well as a viable target for cancer therapy.

Association of Trp-p8 with prostate, lung, breast, and colon cancers and the important role various ion channels play in vital cell functions suggest that the Trp-p8 channel may have a significant function in cancer cell signaling and/or proliferation. Modulation of Trp-p8 activity, either by activating via an agonist or inhibiting via an antagonist, at a physiological temperature can be valuable as a therapeutic to manipulate the Trp-p8 expressing cells in a specific manner. See for example U.S. patent application Ser. No. 10/923,413.

Accordingly, there remains a need in the art for small-molecule modulators of Trp-p8 activity, compositions comprising one or more small-molecule Trp-p8 modulators, and methods for the identification and use of small-molecules for modulating the activity of Trp-p8 in a cell and for the treatment of disease associated with the aberrant expression of Trp-p8.

BRIEF SUMMARY OF THE INVENTION

The present invention fulfills these and other related needs by providing small molecule modulators of Trp-p8 activity, including Trp-p8 agonists and Trp-p8 antagonists, as well as compositions comprising such Trp-p8 modulators, and methods for identifying and using Trp-p8 modulators. Within certain embodiments, compounds of the present invention bind to and activate Trp-p8 and/or stimulate cation influx, including but not limited to calcium influx, in a cell wherein cation influx is correlative of Trp-p8 modulator induced toxicity. Thus, within these and other embodiments, Trp-p8 agonists of the present invention are effective in inhibiting growth of and/or inducing apoptosis and/or necrosis in a cell expressing Trp-p8. Within alternative embodiments are provided Trp-p8 antagonists that are effective in reducing the basal activity of Trp-p8 in a cell thereby reducing the viability of Trp-p8 expressing cells. Advantageously, therefore, agonists and antagonists of the present invention can be used to treat diseases including, but not limited to, cancers of the breast, lung, colon, and/or prostate, that are associated with Trp-p8 expression.

One or more Trp-p8 modulator can be formulated in compositions, including pharmaceutical compositions, comprising one or more pharmaceutically acceptable carrier or excipient and/or one or more additional therapeutic compound. Such compositions will find utility in methods for the treatment of one or more disease associated with Trp-p8 expression.

Thus, in one embodiment, the present invention provides small-molecule Trp-p8 modulators and derivatives thereof wherein the small-molecules include compounds of the following Formula I:

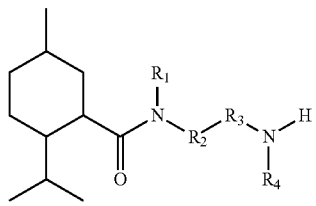

wherein
$R_1$ is selected from H, alkyl, heteroalkyl, arylalkyl, and aryl, or, $R_1$ and $R_2$ together with the nitrogen group may form a cyclic or heterocyclic group of up to 25 atoms;
$R_2$ is selected from aryl and arylalkyl;
$R_3$ is selected from alkyl, heteroalkyl, and arylalkyl;
$R_4$ is selected from H, alkyl, heteroalkyl, and arylalkyl; and
$R_3$ and $R_4$ together with the nitrogen group form an aliphatic amine.

Within related embodiments, the present invention provides small-molecule Trp-p8 modulators and derivatives thereof wherein the small-molecules include compounds of the following Formula I-A:

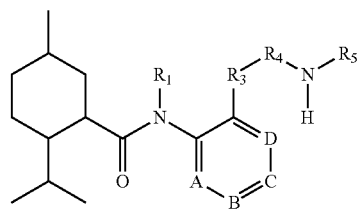

wherein A, B, C, and D are independently selected from $CR_2$ and N; wherein at least one of A, B, C, and D is $CR_2$; wherein $R_2$ is a member selected from H, alkyl, heteroalkyl, aryl, halogen, and arylalkyl, $R_6O$—, and $R_6S$—, wherein $R_6$ is alkyl; wherein when two adjacent of A, B, C, and D are $CR_2$, the two $R_2$'s may combine to form a single aryl, cycloalkyl, or heterocycloalkyl group; and
$R_1$ is selected from H, alkyl, heteroalkyl, aryl, and arylalkyl;
$R_3$ is selected from alkyl, heteroalkyl, aryl, arylalkyl, —$NR_7C(O)$—, —$C(O)NR_7$—, —O—, —S—, —S(O)—, —$S(O)_2$—, and —$NR_7$—, wherein $R_7$ is a member selected from H, alkyl, heteroalkyl, aryl, and arylalkyl;

$R_4$ is selected from —$C(O)R_8$—, alkyl, arylalkyl, and heteroalkyl, wherein $R_8$ is selected from alkyl and heteroalkyl;
$R_5$ is selected from H, alkyl, heteroalkyl, and arylalkyl; and
$R_4$ and $R_5$ together with the nitrogen group form an aliphatic amine.

Within certain exemplary compounds of Formula I-A, $R_1$ is H; $R_7$ is H; $R_8$ comprises 2, 3, or 4 carbons; $R_4$ is selected from propionyl, ethyl, butyryl, hydroxypropionyl, and 3-hydroxybutyryl; $R_5$ is selected from H and methyl; $R_6$ comprises 1, 2, 3, 4, 5, or 6 carbons; and/or $R_2$ is selected from methoxy, methylsulfanyl, phenyl, and H.

Exemplified herein are compounds of Formula I-A comprising a group selected from 2-(2-amino-propionylamino)-4-methoxy-phenyl, N-(2-Amino-ethyl)-2-amino-5-methylsulfanyl-phenyl, 1-(2-amino-ethoxy)-naphthalen-2-yl, 2-(2-amino-ethylamino)-4-methylsulfanyl-phenyl, N-(2-Amino-ethyl)-5-methoxy-benzamide, 2-(2-amino-butyrylamino)-4-methoxy-phenyl, 2-(2-amino-3-hydroxy-propionylamino)-4-methoxy-phenyl, 3-(2-amino-ethylamino)-naphthalen-2-yl, N-(2-Amino-ethyl)-2-amino-benzamide, 2-(2-amino-3-hydroxy-propionylamino)-4-methoxy-phenyl, 2-(2-amino-acetylamino)-phenyl, 2-(2-amino-3-hydroxy-butyrylamino)-4-methoxy-phenylamide, and 2-(2-amino-acetylamino)-4-methoxy-phenyl.

Within alternative related embodiments, the present invention provides small-molecule Trp-p8 modulators and derivatives thereof wherein the small-molecules include compounds of the following Formula I-B:

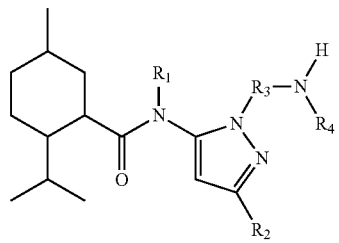

wherein
$R_1$ is selected from H, alkyl, heteroalkyl, aryl, and arylalkyl;
$R_2$ is selected from aryl, alkyl, heteroalkyl, and arylalkyl;
$R_3$ is selected from alkyl, heteroalkyl, and arylalkyl;
$R_4$ is selected from H, alkyl, heteroalkyl, and arylalkyl; and
$R_3$ and $R_4$ together with the nitrogen group form an aliphatic amine.

Within certain exemplary compounds of Formula I-B, $R_1$ is H; $R_3$ is selected from methylene, ethylene, propylene, and butylene; $R_4$ is selected from H and methyl; and/or $R_2$ is selected from phenyl, furan, methylpyrrole, methylbenzoate, aminophenyl, hydroxyphenyl, cyanophenyl, and methoxyphenyl.

Exemplified herein are compounds of Formula I-B comprising a group selected from 2-(2-amino-ethyl)-5-furan-2-yl-2H-pyrazol-3-yl, 2-(2-amino-propyl)-5-phenyl-2H-pyrazol-3-yl, 2-(2-amino-ethyl)-5-phenyl-2H-pyrazol-3-yl, 2-(2-amino-ethyl)-5-(1-methyl-1H-pyrrol-2-yl)-2H-pyrazol-3-yl, 2-(2-amino-propyl)-5-phenyl-2H-pyrazol-3-yl, 2-(2-amino-ethyl)-5-(4-amino-phenyl)-2H-pyrazol-3-yl, 2-(2-amino-ethyl)-5-(4-hydroxy-phenyl)-2H-pyrazol-3-yl, 2-(2-methylamino-ethyl)-5-phenyl-2H-pyrazol-3-yl, 2-(2-amino-propyl)-5-phenyl-2H-pyrazol-3-yl, 2-(2-amino-ethyl)-5-(3-cyano-phenyl)-2H-pyrazol-3-yl, 2-(2-amino-ethyl)-5-(3-methoxy-phenyl)-2H-pyrazol-3-yl, 4-{1-(2-Amino-ethyl)-

1H-pyrazol-3-yl}-benzoic acid methyl ester, 2-(2-amino-ethyl)-5-(3-amino-phenyl)-2H-pyrazol-3-yl, and 2-(2-amino-ethyl)-5-(3-hydroxy-phenyl)-2H-pyrazol-3-yl.

Within still further related embodiments, the present invention provides small-molecule Trp-p8 modulators and derivatives thereof wherein the small-molecules include compounds of the following Formula I-C:

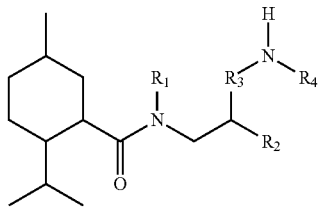

wherein
$R_1$ is selected from H, alkyl, heteroalkyl, aryl, and arylalkyl;
$R_2$ is selected from aryl, and arylalkyl;
$R_3$ is selected from alkyl, heteroalkyl, arylalkyl, —NHC(O)$R_5$—, —O$R_5$—, and —NH$R_5$—, wherein $R_5$ is alkyl or heteroalkyl;
$R_4$ is selected from H, alkyl, heteroalkyl, and arylalkyl; and
$R_3$ and $R_4$ together with the nitrogen group form an aliphatic amine.

Within certain exemplary compounds of Formula I-C, $R_1$ is H; $R_2$ is phenyl; $R_5$ is selected from, methylene, ethylene, propylene, and butylene; $R_3$ is selected from propionylamino, ethoxy, propoxy, and ethylamino; and/or $R_4$ is selected from H and methyl.

Exemplified herein are compounds of Formula I-C comprising a group selected from 2-(2-amino-propionylamino)-2-phenyl-ethyl, 2-(2-amino-ethoxy)-2-phenyl-ethyl, 2-(2-amino-ethoxy)-2-phenyl-ethyl, 2-(3-amino-propoxy)-2-phenyl-ethyl, 2-(2-dimethylamino-ethoxy)-2-phenyl-ethyl, and 2-(2-amino-ethylamino)-2-phenyl-ethyl.

Within still further related embodiments, the present invention provides small-molecule Trp-p8 modulators and derivatives thereof wherein the small-molecules include compounds of the following Formula I-D:

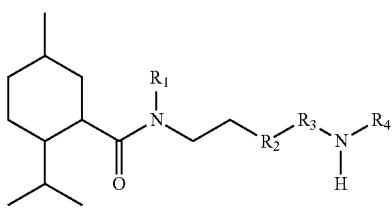

wherein
$R_1$ is selected from H, alkyl, heteroalkyl, aryl, and arylalkyl;
$R_2$ is selected from aryl, and arylalkyl;
$R_3$ is selected from alkyl, heteroalkyl, and arylalkyl;
$R_4$ is selected from H, alkyl, heteroalkyl, and arylalkyl; and
$R_3$ and $R_4$ together with the nitrogen group form an aliphatic amine.

Within certain exemplary compounds of Formula I-D, $R_1$ is H; $R_2$ is selected from phenyl and phenylamino; $R_3$ is selected from methylene, ethylene, propylene, butylene, methylamino, ethylamino, propylamino, butylamino, and acetyl; and/or $R_4$ is selected from H and methyl.

Exemplified herein are compounds of Formula I-D comprising a group selected from 2-[2-(2-amino-ethylamino)-phenyl]-ethyl, 2-(2-aminomethyl-phenyl)-ethyl, and 2-[(2-amino-acetyl)-phenyl-amino]-ethyl.

Within yet other related embodiments, the present invention provides small-molecule Trp-p8 modulators and derivatives thereof wherein the small-molecules include compounds of the following Formula I-E:

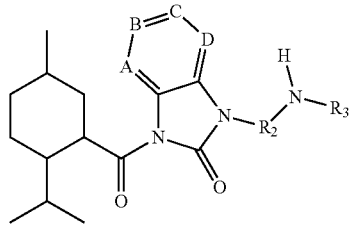

wherein A, B, C, and D are independently selected from $CR_1$ and N; wherein at least one of A, B, C, and D is $CR_1$; wherein $R_1$ is selected from H, alkyl, heteroalkyl, aryl, arylalkyl and halogen; wherein when two adjacent of A, B, C, and D are $CR_1$, the two $R_1$'s may combine to form a single aryl, cycloalkyl, or heterocycloalkyl group;
$R_2$ is selected from alkyl, heteroalkyl and arylalkyl;
$R_3$ is selected from H, alkyl, heteroalkyl, and arylalkyl; and
$R_2$ and $R_3$ together with the nitrogen group form an aliphatic amine.

Within certain exemplary compounds of Formula I-E,
(i) $R_1$ is H or —O$R^i$ and $R^i$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;
(ii) $R_1$ is —S$R^{ii}$. and wherein $R^{ii}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;
(iii) $R_1$ is —S(O)$R^{iii}$ and wherein $R^{iii}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;
iv) $R_1$ is —S(O)$_2$$R^{iv}$ and wherein $R^{iv}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;
(v) $R_1$ is —C(O)NR$^v$R$^{vi}$, wherein R$^v$ and R$^{vi}$ are independently selected from H, methyl, hydroxymethyl, ethyl, hydroxyethyl, propyl, hydroxypropyl, butyl, hydroxybutyl, diethylaminoethyl, phenyl, pyridinyl, methoxyethyl, hydroxyethoxyethyl, benzyl, methylphenyl, phenylethyl, hydroxyhydroxymethylphenylethyl, carbamoylmethyl, and hydroxymethyl hydroxyethyl;
(vi) $R_1$ is —C(O)NR$^v$R$^{vi}$, wherein R$^v$ and R$^{vi}$ together form morpholine, piperazine, piperazine ethyl ester;
(vii) $R_2$ is selected from methylene, ethylene, propylene, and butylene;
(viii) $R_2$ is ethylene and $R_3$ is H; and
(ix) $R_1$ is CF$_3$ or halogen.

Exemplified herein are compounds of Formula I-E comprising a group selected from 3-(2-amino-ethyl)-5-methoxy-1,3-dihydro-benzoimidazol-2-one, 3-(2-Amino-ethyl)-5-(3- hydroxy-propoxy)-1,3-dihydro-benzoimidazol-2-one, 3-(2-Amino-ethyl)-5-ethoxy-1,3-dihydro-benzoimidazol-2-one, 3-(2-Amino-ethyl)-5-methanesulfonyl-1,3-dihydro-benzoimidazol-2-one, 3-(2-Amino-ethyl)-5-(2-hydroxy-ethoxy)-1,3-dihydro-benzoimidazol-2-one, 3-(2-Amino-ethyl)-2-oxo-2,3-dihydro-1H-benzoimidazole-5-carboxylic acid amide, 3-(2-Amino-ethyl)-5-methylsulfanyl-1,3-dihydro-benzoimidazol-2-one, 3-(2-Amino-ethyl)-5-methanesulfinyl-1,3-dihydro-benzoimidazol-2-one, 3-(2-Amino-ethyl)-2-oxo-2,3-dihydro-1H-benzoimidazole-5-carboxylic acid (2-diethylamino-ethyl)-amide, 3-(2-Amino-propyl)-2,3-dihydro-benzoimidazol-2-one, [3-(2-Amino-ethyl)-2-oxo-2,3-dihydro-1H-benzoimidazol-5-yloxy]-acetonitrile, 3-(2-Amino-ethyl)-2-oxo-2,3-dihydro-1H-benzoimidazole-5-carboxylic acid ethylamide, 3-(2-Amino-ethyl)-2-oxo-2,3-dihydro-1H-benzoimidazole-5-carboxylic acid pyridin-3-ylamide, 3-(2-Amino-ethyl)-2-oxo-2,3-dihydro-1H-benzoimidazole-5-carboxylic acid (2-methoxy-ethyl)-amide, 1-(2-Amino-ethyl)-1,3-dihydro-benzoimidazol-2-one, 1-(2-Amino-ethyl)-1,3-dihydro-naphtho[2,3-d]imidazol-2-one, 3-(2-Amino-ethyl)-2-oxo-2,3-dihydro-1H-benzoimidazole-5-carboxylic acid (2-hydroxy-ethyl)-amide, 3-(2-Amino-ethyl)-5-propoxy-1,3-dihydro-benzoimidazol-2-one, 3-(2-Amino-ethyl)-1,3-dihydro-imidazo[4,5-c]pyridin-2-one, 3-(2-Amino-ethyl)-2-oxo-2,3-dihydro-1H-benzoimidazole-4-carboxylic acid (2-diethylamino-ethyl)-amide, 3-(2-Amino-ethyl)-2-oxo-2,3-dihydro-1H-benzoimidazole-5-carboxylic acid pyridin-4-ylamide, 3-(2-Amino-ethyl)-1,3-dihydro-imidazo[4,5-b]pyridin-2-one, 1-(3-Amino-propyl)-1,3-dihydro-benzoimidazol-2-one, 3-(2-Amino-ethyl)-2-oxo-2,3-dihydro-1H-benzoimidazole-5-carboxylic acid phenylamide, 3-(2-Amino-ethyl)-2-oxo-2,3-dihydro-1H-benzoimidazole-5-carboxylic acid [2-(2-hydroxy-ethoxy)-ethyl]-amide, 1-(2-Amino-ethyl)-5-trifluoromethyl-1,3-dihydro-benzoimidazol-2-one, 1-(2-Amino-ethyl)-1,3-dihydro-imidazo[4,5-c]pyridin-2-one, 3-(2-Amino-ethyl)-2-oxo-2,3-dihydro-1H-benzoimidazole-5-carboxylic acid benzylamide, 3-(2-Amino-ethyl)-5-(morpholine-4-carbonyl)-1,3-dihydro-benzoimidazol-2-one, 3-(2-Amino-ethyl)-5-(2-oxo-2-phenyl-ethoxy)-1,3-dihydro-benzoimidazol-2-one, 3-(2-methylamino-ethyl)-1,3-dihydro-benzoimidazol-2-one, 3-(2-Amino-ethyl)-5-butoxy-1,3-dihydro-benzoimidazol-2-one, 3-(2-Amino-ethyl)-2-oxo-2,3-dihydro-1H-benzoimidazole-5-carboxylic acid methylphenyl-amide, 4-[3-(2-Amino-ethyl)-2-oxo-2,3-dihydro-1H-benzoimidazole-5-carbonyl]-piperazine-1-carboxylic acid ethyl ester, 3-(2-Amino-ethyl)-2-oxo-2,3-dihydro-1H-benzoimidazole-5-carboxylic acid diethylamide, 3-(2-Amino-ethyl)-2-oxo-2,3-dihydro-1H-benzoimidazole-5-carboxylic acid phenethyl-amide, 3-(2-Amino-ethyl)-2-oxo-2,3-dihydro-1H-benzoimidazole-5-carboxylic acid (2-hydroxy-1-hydroxymethyl-2-phenyl-ethyl)-amide, 3-(2-Amino-ethyl)-2-oxo-2,3-dihydro-1H-benzoimidazole-5-carboxylic acid carbamoylmethyl-amide, 3-(2-Amino-ethyl)-2-oxo-2,3-dihydro-1H-benzoimidazole-5-carboxylic acid (2-hydroxy-1-hydroxymethyl-ethyl)-amide, N-{2-[2-oxo-2,3-dihydro-benzoimidazol-1-yl]-ethyl}-guanidine, 3-(2-Amino-ethyl)-5-benzyloxy-1,3-dihydro-benzoimidazol-2-one, and 1-(4-Amino-butyl)-1,3-dihydro-benzoimidazol-2-one. Within one such embodiment, is provided the compound 3-(2-Amino-ethyl)-1-(2-isopropyl-5-methyl-cyclohexanecarbonyl)-5-methoxy-1,3-dihydro-benzoimidazol-2-one.

Other aspects of the present invention provide compositions, including pharmaceutical compositions, comprising one or more small-molecule Trp-p8 modulators of Formula I, Formula I-A, Formula I-B, Formula I-C, Formula I-D, and Formula I-E in combination with a pharmaceutically acceptable excipient, carrier and/or diluent. Exemplified herein within the Examples are specific Trp-p8 agonists and antagonists of Formula I, Formula I-A, Formula I-B, Formula I-C, Formula I-D, and Formula I-E; methods for synthesizing exemplary Trp-p8 agonists and antagonists of Formula I, Formula I-A, Formula I-B, Formula I-C, Formula I-D, and Formula I-E; and EC50 data demonstrating the in vitro efficacy and specific activity of each of the disclosed Trp-p8 agonists and antagonists of Formula I, Formula I-A, Formula I-B, Formula I-C, Formula I-D, and Formula I-E.

Within still further aspects, compositions of the present invention comprise one or more compound of Formula I, Formula I-A, Formula I-B, Formula I-C, Formula I-D, and/or Formula I-E formulated together with one or more cancer therapeutic agent. Alternatively, compositions of the present invention comprise a compound of Formula I, Formula I-A, Formula I-B, Formula I-C, Formula I-D, and/or Formula I-E independently formulated with one or more cancer therapeutic agent. That is, one or more compound of Formula I, Formula I-A, Formula I-B, Formula I-C, Formula I-D, and/or Formula I-E and the cancer therapeutic agent are separately formulated.

Suitable cancer therapeutic agents include, but are not limited to, antimitotic agents including, but not limited to, paclitaxel, vincristine, and etoposide; alkylating agents including, but not limited to, mechlorethamine, cyclophosphamide, and carmustine; antimetabolites including, but not limited to, methotrexate, gemcitabine, lometrexol, 5-fluorouracil, and 6-mercaptopurine; cytotoxic antibiotics including, but not limited to, doxorubicin, daunorubicin, bleomycin, mitomycin C, and streptozocin; platinum agents including, but not limited to, cisplatin and carboplatin; hormonal agents including, but not limited to, anti-estrogens such as tamoxifen and diethylstilbestrol as well as anti-androgens such as flutamide; antiangiogenesis agents; and farnesyl transferase inhibitors.

In certain aspects, compounds of Formula I, Formula I-A, Formula I-B, Formula I-C, Formula I-D, and/or Formula I-E are administered in combination with cancer therapeutic agents that are themselves ineffective for modulating Trp-p8 activity in a cell expressing Trp-p8. Surprisingly, these types of combination therapies result in enhanced efficacy relative to the use of a single compound of Formula I, Formula I-A, Formula I-B, Formula I-C, Formula I-D, and/or Formula I-E alone.

In other aspects, compounds of Formula I, Formula I-A, Formula I-B, Formula I-C, Formula I-D, and/or Formula I-E are administered in combination with one or more additional Trp-p8 modulator(s) including, but not limited to, a compound of Formula I, Formula I-A, Formula I-B, Formula I-C, Formula I-D, and/or Formula I-E.

Within certain of these embodiments are provided small-molecule antagonists of the small-molecule Trp-p8 agonists presented herein. Thus, within certain embodiments are provided small-molecule Trp-p8 antagonists of Formula I, Formula I-A, Formula I-B, Formula I-C, Formula I-D, and/or Formula I-E, and derivatives thereof, of one or more Formula I, Formula I-A, Formula I-B, Formula I-C, Formula I-D, and Formula I-E Trp-p8 agonist.

Further embodiments of the present invention provide methods for decreasing cell viability and/or inhibiting cell growth, methods for stimulating cation influx, and methods for inducing apoptosis and/or necrosis in a cell expressing Trp-p8. Exemplary such methods comprise the step of contacting a cell with a compound of Formula I, Formula I-A, Formula I-B, Formula I-C, Formula I-D, and/or Formula I-E in a concentration and for a time required to decrease cell viability and/or inhibit cell growth, to raise intracellular calcium, and/or to induce apoptosis and/or necrosis of the cell.

In still further embodiments, the present invention provides methods for treating a disease in a mammal, most typically a human, by administering one or more compound and/or composition of the present invention. In certain aspects, the methods include the administration of a composition comprising a combination of a compound of Formula I, Formula I-A, Formula I-B, Formula I-C, Formula I-D, and/or Formula I-E with one or more cancer therapeutic agent delivered in a simultaneous manner, such as in a single formulation. In certain other aspects, the methods of the present invention include combination therapy wherein the compound of Formula I, Formula I-A, Formula I-B, Formula I-C, Formula I-D, and/or Formula I-E is administered first in one formulation, followed by the cancer therapeutic agent in a separate formulation. The methods also include a cancer therapeutic agent being delivered first in one formulation, followed by a compound of Formula I, Formula I-A, Formula I-B, Formula I-C, Formula I-D, and/or Formula I-E in a separate formulation.

Therapeutic methods of the present invention are particularly effective in the treatment of cancers associated with the expression of Trp-p8 including, but not limited to, certain colon, lung, breast, and prostate cancers.

The above-mentioned and additional features of the present invention and the manner of obtaining them will become apparent, and the invention will be best understood by reference to the following more detailed description, read in conjunction with the accompanying figures.

BRIEF DESCRIPTION OF THE FIGURES

FIGS. 1A-1B are graphs depicting an exemplary ATP viability assay suitable for testing and characterizing small-molecule Trp-p8 modulators of the present invention. In a preliminary assay (FIG. 1A), compounds were tested at 1 µM and specific killing of Trp-p8 expressing CHO cells (CHO/Trp-p8) measured at 37° C. In a follow up assay (FIG. 1B), compounds were tested at various concentrations, and killing of Trp-p8 expressing CHO cells (CHO/Trp-p8) was measured at 37° C. An $EC_{50}$ value was derived from a plot of cell viability as a function of concentration FIGS. 2A-2C are graphs depicting Trp-p8 modulator-induced increases in intracellular calcium as determined by a calcium flux assay performed at 37° C. FIG. 2A is a positive control demonstrating that CHO and CHO/Trp-p8 cells respond similarly to 2 µM Ionomycin at 37° C. in the calcium flux assay. FIG. 2B is a negative control demonstrating that parental CHO cells that do not express endogenous or exogenous Trp-p8 do not respond to Trp-p8 agonists at a concentration of 10 µM. FIG. 2C demonstrates that a Trp-p8 agonist induced a specific, concentration-dependent response in CHO/Trp-p8 cells at 37° C.

FIG. 3 are plots of flow cytometry data demonstrating that a Trp-p8 agonist is capable of specifically inducing apoptosis in Trp-p8 expressing CHO cells at 37° C., in a dose-dependent manner.

FIG. 4 is a graph depicting exemplary results from a primary screen for Trp-p8 antagonists using the ATP viability assay, described herein, with CHO/Trp-p8 cells at 37° C. CHO/Trp-p8 cells were exposed to compounds, at different concentrations, in 1% DMSO or 1% DMSO in combination with a toxic concentration of a Trp-p8 agonist. The viability of cells was measured after 24-26 hours at 37° C. using the ATP assay. Compounds that protected the cells from the toxic effect of the Trp-p8 agonist are classified as Trp-p8 antagonists (Compounds A-B). An inactive compound (Compound C) had no protective effect and is shown here for the purpose of illustration of the assay.

FIG. 5 is a graph depicting the screening and characterization of Trp-p8 antagonists by the calcium flux assay performed at 37° C. CHO/Trp-p8 cells were loaded with the calcium indicator dye, Fura-2, and the increase in intracellular calcium in response to compounds was determined by the increase in fluorescence. Fura-2 dye loaded CHO/Trp-p8 cells were exposed to 1% DMSO or an antagonist, at different concentrations, in 1% DMSO at 37° C. Three minutes later, an agonist was added to the cells. When cells were exposed to effective concentrations of the antagonist, their ability to respond to the agonist was significantly reduced or eliminated altogether.

FIGS. 6A-6B are graphs depicting results from an exemplary animal model suitable for testing and characterizing small-molecule Trp-p8 modulators of the present invention. Mice were injected subcutaneously with CHO/Trp-p8 cells, resulting in the formation of solid tumors. The length (longest dimension) and width (dimension perpendicular to and in the same plane as length) of each tumor was measured with Vernier calipers, and the tumor volume was approximated by a formula for the volume of an ellipsoid: $0.52*L*W^2$. When the average tumor volume reached approximately 100 mm$^3$, the mice were randomized into groups. In FIG. 6A, the mice were administered a single dose of either a study compound as an aqueous formulation, or vehicle alone, by oral gavage. In FIG. 6B, the mice were dosed repeatedly with either a study compound as an aqueous formulation, or vehicle alone, by oral gavage. Tumors were then subsequently measured on the indicated days. The data is presented as mean tumor volumes±standard error of the mean.

dimension perpendicular to and in the same plane as length) of each tumor was measured with Vernier calipers, and the tumor volume was approximated by a formula for the volume of an ellipsoid: 0.52*L*W². When the mean tumor volume reached approximately 100 mm³, the mice were randomized into groups, and administered a single dose of either a compound as an aqueous formulation, or vehicle alone, by oral gavage. Tumors were then subsequently measured on the indicated days. The data is presented as mean tumor volumes±standard error of the mean.

Figure 11:
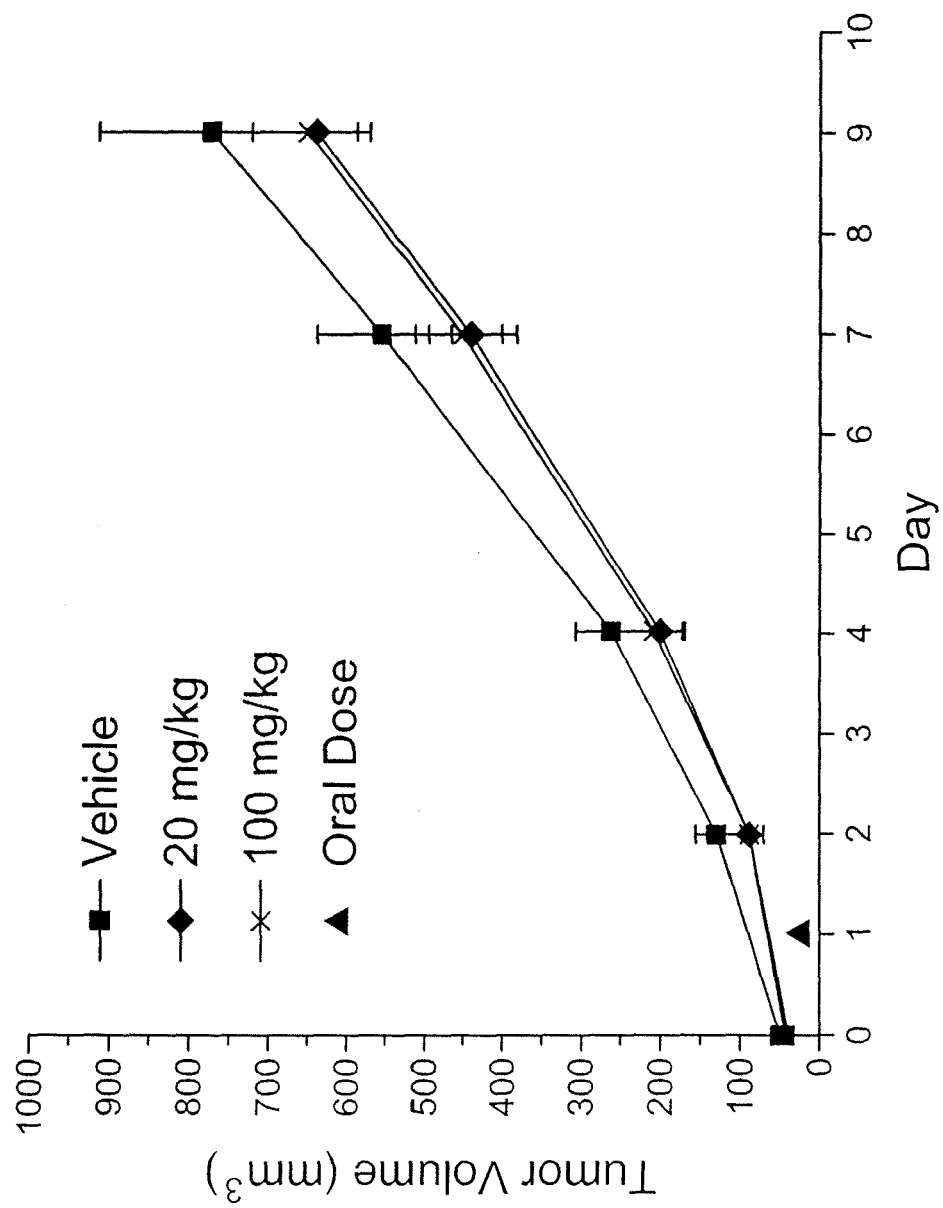

FIG. 11 is a graph depicting the lack of efficacy demonstrated by an exemplary compound in a murine tumor xenograft model lacking Trp-p8 expression. Mice were injected subcutaneously with CHO-K1 cells lacking Trp-p8, resulting in the formation of solid tumors. The length (L; longest dimension) and width (W; dimension perpendicular to and in the same plane as length) of each tumor was measured with Vernier calipers, and the tumor volume was approximated by a formula for the volume of an ellipsoid: 0.52*L*W². When the average tumor volume reached approximately 50 mm³, the mice were randomized into groups, and administered either a single dose of the compound as an aqueous formulation, or vehicle, by oral gavage. Tumors were then subsequently measured on the indicated days. The data is presented as mean tumor volumes±standard error of the mean.

FIG. 12 is a graph depicting the efficacy demonstrated by and exemplary compound in a murine tumor xenograft model expressing Trp-p8. The LuCaP tumor model was obtained from Robert L. Vassella, Ph.D., Professor of Urology in the University of Washington's School of Medicine. The length (L; longest dimension) and width (W; dimension perpendicular to and in the same plane as length) of each tumor was measured with Vernier calipers, and the tumor volume was approximated by a formula for the volume of an ellipsoid: 0.52*L*W². When the average tumor volume reached approximately 150 mm³, the mice were administered the compound, as an aqueous formulation, by intraperitoneal injection, once a day for 5 days. Tumors were then subsequently measured on the indicated days. The data is presented as mean tumor volumes±standard error of the mean.

SEQ ID NO: 1 is the nucleotide sequence of a human Trp-p8 cDNA (GenBank Accession No. AY090109).

SEQ ID NO: 2 is the amino acid sequence encoded by the nucleotide sequence of SEQ ID NO: 1 (GenBank Accession No. NP_076985).

DETAILED DESCRIPTION OF THE INVENTION

The present invention is based upon the discovery that certain small-molecule Trp-p8 modulators, including agonists of Trp-p8 activity, are capable of inhibiting the growth of and/or inducing apoptosis and/or necrosis in cells that express Trp-p8. Without wishing to be limited to any specific mode of action, it is believed that Trp-p8 agonist-mediated activation of the Trp-p8 receptor substantially increases cation influx, which is correlative of cellular toxicity. It is further believed that Trp-p8 antagonists can inhibit the basal level and/or native ligand-induced activity of endogenous Trp-p8 activation which, consequently, leads to reduced growth or death of cells expressing this cation channel protein.

Thus, the present invention provides small-molecule Trp-p8 modulators, including agonists and antagonists of Trp-p8 activity, as well as compositions, including pharmaceutical compositions, comprising one or more small-molecule Trp-p8 modulator in combination with one or more pharmaceutically acceptable carrier and/or excipient. The present invention also provides combination compositions comprising one or more Trp-p8 modulator and one or more additional therapeutic compound such as, for example, a cancer therapeutic agent. Trp-p8 modulators and compositions comprising Trp-p8 modulators will find utility in methods for activating Trp-p8-mediated cation influx in a cell, methods for inducing apoptosis and/or necrosis in a cell, as well as methods for the treatment of diseases associated with Trp-p8 expression including, but not limited to, cancers, such as breast, colon, lung, and prostate cancers.

DEFINITIONS

The term "Trp-p8 modulators" refers collectively to compounds which are small-molecule agonists and antagonists that bind to and either increase or decrease, respectively, the activity of Trp-p8 in a cell. Trp-p8 agonists include compounds of Formula I, Formula I-A, Formula I-B, Formula I-C, Formula I-D, and Formula I-E and chemical derivatives thereof. Trp-p8 antagonists of Formula I, Formula I-A, Formula I-B, Formula I-C, Formula I-D, and Formula I-E may be readily synthesized and characterized by a skilled artisan by employing the methodology expressly provided herein and/or as is readily available in the art.

The phrase "activate Trp-p8" means agonist-mediated activation of Trp-p8 expressed on the surface of a cell. For example, within certain embodiments, agonists of the present invention, when contacted with a cell and/or administered in vivo to a mammalian subject, activate Trp-p8 thereby facilitating the influx of cations, such as calcium ions, to such an intracellular level and/or for such a duration that is sufficient to cause toxicity to the cell as evidenced by a diminution in cell growth and/or an onset of necrotic and/or apoptotic cell death.

The term "aliphatic amine" means a substituted nitrogen atom wherein any substituents, other than H, are attached to the nitrogen by a saturated carbon atom.

The term "alkyl," by itself or as part of another substituent, means, unless otherwise stated, a straight or branched chain, or cyclic hydrocarbon group, or combination thereof, which may be fully saturated, mono or polyunsaturated and can include di and multivalent groups, having the number of carbon atoms designated (i.e. $C_1$-$C_{10}$ means one to ten carbons). Examples of saturated hydrocarbon groups include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "alkylene" by itself or as part of another substituent means a divalent group derived from an alkane, as exemplified by —$CH_2CH_2CH_2CH_2$—. Typically, an alkylene group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "cycloalkylene" by itself or as part of another substituent means a divalent group derived from a cycloalkane, as exemplified by cyclohexylene. Typically, a cycloalkylene group will have from 5-8 carbon atoms, with those groups having 6 carbon atoms being preferred in the present invention.

The term "alkenylene" by itself or as part of another substituent means a divalent group derived from an alkenyl, as exemplified by —CH=CHCH$_2$CH$_2$—. Typically, alkenylene groups will have from 2 to 24 carbon atoms, with those groups having 10 or fewer carbon atoms being preferred in the present invention.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$—)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$—, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Also included in the term "heteroalkyl" are those groups described in more detail below as "heterocycloalkyl." The term "heteroalkylene" by itself or as part of another substituent means a divalent group derived from heteroalkyl, as exemplified by —CH$_2$—CH$_2$—S—CH$_2$CH$_2$— and —CH$_2$—S—CH$_2$CH$_2$—NH—CH$_2$—. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

An "activated carbonyl" group is a carbonyl group whose electrophilicity is enhanced as a result of the groups attached to either side of the carbonyl. Examples of such activated carbonyl groups are (polyfluoroalkyl)ketones, (polyfluoroalkyl)aldehydes, alpha-keto esters, alpha-keto acids, alpha-keto amides, 1,2-diketones, 2-acylthiazoles, 2-acylimidazoles, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently.

The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those groups in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated group. Preferred substituents for each type of group are provided below.

Substituents for the alkyl and heteroalkyl groups (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such group. R', R" and R'" each independently refer to hydrogen, unsubstituted(C$_1$-C$_8$) alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR"—S(O)$_2$—R', —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl, (unsubstituted aryl)-(C$_1$-C$_4$)alkyl, and (unsubstituted aryl)oxy-(C$_1$-C$_4$)alkyl.

Two of the substituents on adjacent atoms of the aryl ring may optionally be replaced with a substituent of the formula -T-C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), and sulfur (S).

The term "pharmaceutically acceptable salts" is meant to include salts of the active compounds of Formula I, Formula I-A, Formula I-B, Formula I-C, Formula I-D, and Formula I-E that are prepared with relatively nontoxic acids or bases, depending on the particular substituents found on the compounds described herein. Examples of pharmaceutically acceptable base addition salts include, but are not limited to, sodium, potassium, calcium, ammonium, organic amino, magnesium salt, or other similar salt. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrophosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like.

Small-Molecule Modulators of Trp-p8 Activity

Small-molecule Trp-p8 modulators that are suitably employed in the compositions and methods of the present invention are exemplified herein by compounds of Formula I, Formula I-A, Formula I-B, Formula I-C, Formula I-D, and/or Formula I-E disclosed herein, and derivatives thereof.

Thus, in one embodiment, the present invention provides small-molecule Trp-p8 modulators and derivatives thereof wherein the small-molecules include compounds of the following Formula I:

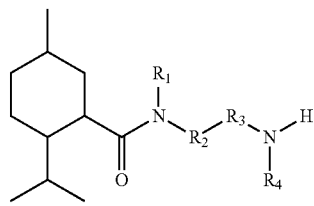

wherein
$R_1$ is selected from H, alkyl, heteroalkyl, arylalkyl, and aryl, or, $R_1$ and $R_2$ together with the nitrogen group may form a cyclic or heterocyclic group of up to 25 atoms;
$R_2$ is selected from aryl and arylalkyl;
$R_3$ is selected from alkyl, heteroalkyl, and arylalkyl;
$R_4$ is selected from H, alkyl, heteroalkyl, and arylalkyl; and
$R_3$ and $R_4$ together with the nitrogen group form an aliphatic amine.

Within related embodiments, the present invention provides small-molecule Trp-p8 modulators and derivatives thereof wherein the small-molecules include compounds of the following Formula I-A:

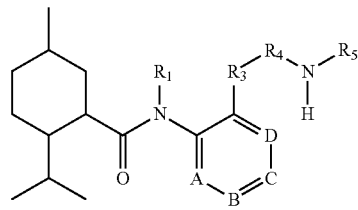

wherein A, B, C, and D are independently selected from CR$_2$ and N; wherein at least one of A, B, C, and D is CR$_2$; wherein $R_2$ is a member selected from H, alkyl, heteroalkyl, aryl, halogen, arylalkyl, R$_6$O—, and R$_6$S—, wherein R$_6$ is alkyl; wherein when two adjacent of A, B, C, and D are CR$_2$, the two R$_2$'s may combine to form a single aryl, cycloalkyl, or heterocycloalkyl group; and
$R_1$ is selected from H, alkyl, heteroalkyl, aryl, and arylalkyl;
$R_3$ is selected from alkyl, heteroalkyl, aryl, arylalkyl, —NR$_7$C(O)—, —C(O)NR$_7$—, —O—, —S—, —S(O)—, —S(O)$_2$—, and —NR$_7$—, wherein R$_7$ is a member selected from H, alkyl, heteroalkyl, aryl, and arylalkyl;
$R_4$ is selected from —C(O)R$_8$—, alkyl, arylalkyl, and heteroalkyl, wherein R$_8$ is selected from alkyl and heteroalkyl;
$R_5$ is selected from H, alkyl, heteroalkyl, and arylalkyl; and
$R_4$ and $R_5$ together with the nitrogen group form an aliphatic amine.

Within certain exemplary compounds of Formula I-A, $R_1$ is H; $R_7$ is H; $R_8$ comprises 2, 3, or 4 carbons; $R_4$ is selected from propionyl, ethyl, butyryl, hydroxypropionyl, and 3-hydroxybutyryl; $R_5$ is selected from H and methyl; $R_6$ comprises 1, 2, 3, 4, 5, or 6 carbons; and/or $R_2$ is selected from methoxy, methylsulfanyl, phenyl, and H.

Exemplified herein are compounds of Formula I-A comprising a group selected from 2-(2-amino-propionylamino)-4-methoxy-phenyl, N-(2-Amino-ethyl)-2-amino-5-methylsulfanyl-phenyl, 1-(2-amino-ethoxy)-naphthalen-2-yl, 2-(2-amino-ethylamino)-4-methylsulfanyl-phenyl, N-(2-Amino-ethyl)-5-methoxy-benzamide, 2-(2-amino-butyrylamino)-4-methoxy-phenyl, 2-(2-amino-3-hydroxy-propionylamino)-4-methoxy-phenyl, 3-(2-amino-ethylamino)-naphthalen-2- yl, N-(2-Amino-ethyl)-2-amino-benzamide, 2-(2-amino-3-hydroxy-propionylamino)-4-methoxy-phenyl, 2-(2-amino-acetylamino)-phenyl, 2-(2-amino-3-hydroxy-butyrylamino)-4-methoxy-phenylamide, and 2-(2-amino-acetylamino)-4-methoxy-phenyl.

Within alternative related embodiments, the present invention provides small-molecule Trp-p8 modulators and derivatives thereof wherein the small-molecules include compounds of the following Formula I-B:

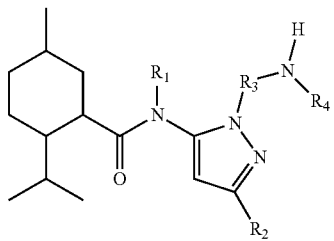

wherein $R_1$ is selected from H, alkyl, heteroalkyl, aryl, and arylalkyl;

$R_2$ is selected from aryl, alkyl, heteroalkyl, and arylalkyl;

$R_3$ is selected from alkyl, heteroalkyl, and arylalkyl;

$R_4$ is selected from H, alkyl, heteroalkyl, and arylalkyl; and $R_3$ and $R_4$ together with the nitrogen group form an aliphatic amine.

Within certain exemplary compounds of Formula I-B, $R_1$ is H; $R_3$ is selected from methylene, ethylene, propylene, and butylene; $R_4$ is selected from H and methyl; and/or $R_2$ is selected from phenyl, furan, methylpyrrole, methylbenzoate, aminophenyl, hydroxyphenyl, cyanophenyl, and methoxyphenyl.

Exemplified herein are compounds of Formula I-B comprising a group selected from 2-(2-amino-ethyl)-5-furan-2-yl-2H-pyrazol-3-yl, 2-(2-amino-propyl)-5-phenyl-2H-pyrazol-3-yl, 2-(2-amino-ethyl)-5-phenyl-2H-pyrazol-3-yl, 2-(2-amino-ethyl)-5-(1-methyl-1H-pyrrol-2-yl)-2H-pyrazol-3-yl, 2-(2-amino-propyl)-5-phenyl-2H-pyrazol-3-yl, 2-(2-amino-ethyl)-5-(4-amino-phenyl)-2H-pyrazol-3-yl, 2-(2-amino-ethyl)-5-(4-hydroxy-phenyl)-2H-pyrazol-3-yl, 2-(2-methylamino-ethyl)-5-phenyl-2H-pyrazol-3-yl, 2-(2-amino-propyl)-5-phenyl-2H-pyrazol-3-yl, 2-(2-amino-ethyl)-5-(3-cyano-phenyl)-2H-pyrazol-3-yl, 2-(2-amino-ethyl)-5-(3-methoxy-phenyl)-2H-pyrazol-3-yl, 4-{1-(2-Amino-ethyl)-1H-pyrazol-3-yl}-benzoic acid methyl ester, 2-(2-amino-ethyl)-5-(3-amino-phenyl)-2H-pyrazol-3-yl, and 2-(2-amino-ethyl)-5-(3-hydroxy-phenyl)-2H-pyrazol-3-yl.

Within still further related embodiments, the present invention provides small-molecule Trp-p8 modulators and derivatives thereof wherein the small-molecules include compounds of the following Formula I-C:

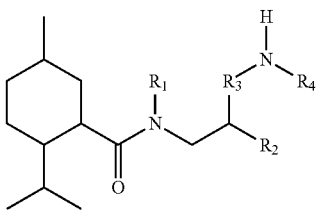

wherein $R_1$ is selected from H, alkyl, heteroalkyl, aryl, and arylalkyl;

$R_2$ is selected from aryl, and arylalkyl;

$R_3$ is selected from alkyl, heteroalkyl, arylalkyl, —NHC(O)$R_5$—, —O$R_5$—, and —NH$R_5$—, wherein $R_5$ is alkyl or heteroalkyl;

$R_4$ is selected from H, alkyl, heteroalkyl, and arylalkyl; and $R_3$ and $R_4$ together with the nitrogen group form an aliphatic amine.

Within certain exemplary compounds of Formula I-C, $R_1$ is H; $R_2$ is phenyl; $R_5$ is selected from, methylene, ethylene, propylene, and butylene; $R_3$ is selected from propionylamino, ethoxy, propoxy, and ethylamino; and/or $R_4$ is selected from H and methyl.

Exemplified herein are compounds of Formula I-C comprising a group selected from 2-(2-amino-propionylamino)-2-phenyl-ethyl, 2-(2-amino-ethoxy)-2-phenyl-ethyl, 2-(2-amino-ethoxy)-2-phenyl-ethyl, 2-(3-amino-propoxy)-2-phenyl-ethyl, 2-(2-dimethylamino-ethoxy)-2-phenyl-ethyl, and 2-(2-amino-ethylamino)-2-phenyl-ethyl.

Within still further related embodiments, the present invention provides small-molecule Trp-p8 modulators and derivatives thereof wherein the small-molecules include compounds of the following Formula I-D:

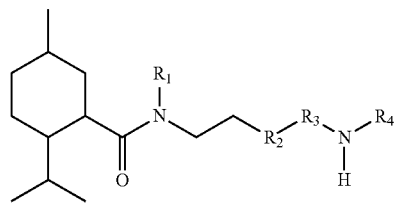

wherein $R_1$ is selected from H, alkyl, heteroalkyl, aryl, and arylalkyl;

$R_2$ is selected from aryl, and arylalkyl;

$R_3$ is selected from alkyl, heteroalkyl, and arylalkyl;

$R_4$ is selected from H, alkyl, heteroalkyl, and arylalkyl; and $R_3$ and $R_4$ together with the nitrogen group form an aliphatic amine.

Within certain exemplary compounds of Formula I-D, $R_1$ is H; $R_2$ is selected from phenyl and phenylamino; $R_3$ is selected from methylene, ethylene, propylene, butylene, methylamino, ethylamino, propylamino, butylamino, and acetyl; and/or $R_4$ is selected from H and methyl.

Exemplified herein are compounds of Formula I-D comprising a group selected from 2-[2-(2-amino-ethylamino)-phenyl]-ethyl, 2-(2-aminomethyl-phenyl)-ethyl, and 2-[(2-amino-acetyl)-phenyl-amino]-ethyl.

Within yet other related embodiments, the present invention provides small-molecule Trp-p8 modulators and derivatives thereof wherein the small-molecules include compounds of the following Formula I-E:

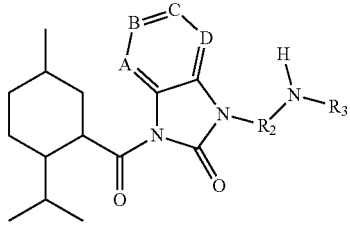

wherein A, B, C, and D are independently selected from $CR_1$ and N; wherein at least one of A, B, C, and D is $CR_1$; wherein $R_1$ is selected from H, alkyl, heteroalkyl, aryl, arylalkyl, and halogen; wherein when two adjacent of A, B, C, and D are $CR_1$, the two $R_1$s may combine to form a single aryl, cycloalkyl, or heterocycloalkyl group;

$R_2$ is selected from alkyl, heteroalkyl and arylalkyl;

$R_3$ is selected from H, alkyl, heteroalkyl, and arylalkyl; and $R_2$ and $R_3$ together with the nitrogen group form an aliphatic amine.

Within certain exemplary compounds of Formula I-E, (i) $R_1$ is H or $-OR^i$ and $R^i$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;

(ii) $R_1$ is $-SR^{ii}$ and wherein $R^{ii}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;

(iii) $R_1$ is $-S(O)R^{iii}$ and wherein $R^{iii}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;

(iv) $R_1$ is $-S(O)_2R^{iv}$ and wherein $R^{iv}$ is selected from methyl, hydroxymethyl, ethyl, hydroxyethyl, propyl, hydroxypropyl, butyl, hydroxybutyl, acetonitrile, phenyl, phenylmethoxy, phenylethoxy, phenylpropoxy, phenylbutoxy, and benzyl;

v) $R_1$ is $-C(O)NR^vR^{vi}$, wherein $R^v$ and $R^{vi}$ are independently selected from H, methyl, hydroxymethyl, ethyl, hydroxyethyl, propyl, hydroxypropyl, butyl, hydroxybutyl, diethylaminoethyl, phenyl, pyridinyl, methoxyethyl, hydroxyethoxyethyl, benzyl, methylphenyl, phenylethyl, hydroxyhydroxymethylphenylethyl, carbamoylmethyl, and hydroxymethyl hydroxyethyl;

(vi) $R_1$ is $-C(O)NR^vR^{vi}$, wherein $R^v$ and $R^{vi}$ together form morpholine, piperazine, piperazine ethyl ester;

(vii) $R_2$ is selected from methylene, ethylene, propylene, and butylene;

(viii) $R_2$ is ethylene and $R_3$ is H (ix) $R_1$ is $CF_3$ or halogen.

Exemplified herein are compounds of Formula I-E comprising a group selected from 3-(2-amino-ethyl)-5-methoxy-1,3-dihydro-benzoimidazol-2-one, 3-(2-Amino-ethyl)-5-(3-hydroxy-propoxy)-1,3-dihydro-benzoimidazol-2-one, 3-(2-Amino-ethyl)-5-ethoxy-1,3-dihydro-benzoimidazol-2-one, 3-(2-Amino-ethyl)-5-methanesulfonyl-1,3-dihydro-benzoimidazol-2-one, 3-(2-Amino-ethyl)-5-(2-hydroxy-ethoxy)-1,3-dihydro-benzoimidazol-2-one, 3-(2-Amino-ethyl)-2-oxo-2,3-dihydro-1H-benzoimidazole-5-carboxylic acid amide, 3-(2-Amino-ethyl)-5-methylsulfanyl-1,3-dihydro-benzoimidazol-2-one, 3-(2-Amino-ethyl)-5-methanesulfinyl-1,3-dihydro-benzoimidazol-2-one, 3-(2-Amino-ethyl)-2-oxo-2,3-dihydro-1H-benzoimidazole-5-carboxylic acid (2-diethylamino-ethyl)-amide, 3-(2-Amino-propyl)-2,3-dihydro-benzoimidazol-2-one, [3-(2-Amino-ethyl)-2-oxo-2,3-dihydro-1H-benzoimidazol-5-yloxy]-acetonitrile, 3-(2-Amino-ethyl)-2-oxo-2,3-dihydro-1H-benzoimidazole-5-carboxylic acid ethylamide, 3-(2-Amino-ethyl)-2-oxo-2,3-dihydro-1H-benzoimidazole-5-carboxylic acid pyridin-3-ylamide, 3-(2-Amino-ethyl)-2-oxo-2,3-dihydro-1H-benzoimidazole-5-carboxylic acid (2-methoxy-ethyl)-amide, 1-(2-Amino-ethyl)-1,3-dihydro-benzoimidazol-2-one, 1-(2-Amino-ethyl)-1,3-dihydro-naphtho[2,3-d]imidazol-2-one, 3-(2-Amino-ethyl)-2-oxo-2,3-dihydro-1H-benzoimidazole-5-carboxylic acid (2-hydroxy-ethyl)-amide, 3-(2-Amino-ethyl)-5-propoxy-1,3-dihydro-benzoimidazol-2-one, 3-(2-Amino-ethyl)-1,3-dihydro-imidazo[4,5-c]pyridin-2-one, 3-(2-Amino-ethyl)-2-oxo-2,3-dihydro-1H-benzoimidazole-4-carboxylic acid (2-diethylamino-ethyl)-amide, 3-(2-Amino-ethyl)-2-oxo-2,3-dihydro-1H-benzoimidazole-5-carboxylic acid pyridin-4-ylamide, 3-(2-Amino-ethyl)-1,3-dihydro-imidazo[4,5-b]pyridin-2-one, 1-(3-Amino-propyl)-1,3-dihydro-benzoimidazol-2-one, 3-(2-Amino-ethyl)-2-oxo-2,3-dihydro-1H-benzoimidazole-5-carboxylic acid phenylamide, 3-(2-Amino-ethyl)-2-oxo-2,3-dihydro-1H-benzoimidazole-5-carboxylic acid [2-(2-hydroxy-ethoxy)-ethyl]-amide, 1-(2-Amino-ethyl)-5-trifluoromethyl-1,3-dihydro-benzoimidazol-2-one, 1-(2-Amino-ethyl)-1,3-dihydro-imidazo[4,5-c]pyridin-2-one, 3-(2-Amino-ethyl)-2-oxo-2,3-dihydro-1H-benzoimidazole-5-carboxylic acid benzylamide, 3-(2-Amino-ethyl)-5-(morpholine-4-carbonyl)-1,3-dihydro-benzoimidazol-2-one, 3-(2-Amino-ethyl)-5-(2-oxo-2-phenyl-ethoxy)-1,3-dihydro-benzoimidazol-2-one, 3-(2-methylamino-ethyl)-1,3-dihydro-benzoimidazol-2-one, 3-(2-Amino-ethyl)-5-butoxy-1,3-dihydro-benzoimidazol-2-one, 3-(2-Amino-ethyl)-2-oxo-2,3-dihydro-1H-benzoimidazole-5-carboxylic acid methylphenyl-amide, 4-[3-(2-Amino-ethyl)-2-oxo-2,3-dihydro-1H-benzoimidazole-5-carbonyl]-piperazine-1-carboxylic acid ethyl ester, 3-(2-Amino-ethyl)-2-oxo-2,3-dihydro-1H-benzoimidazole-5-carboxylic acid diethylamide, 3-(2-Amino-ethyl)-2-oxo-2,3-dihydro-1H-benzoimidazole-5-carboxylic acid phenethyl-amide, 3-(2-Amino-ethyl)-2-oxo-2,3-dihydro-1H-benzoimidazole-5-carboxylic acid (2-hydroxy-1-hydroxymethyl-2-phenyl-ethyl)-amide, 3-(2-Amino-ethyl)-2-oxo-2,3-dihydro-1H-benzoimidazole-5-carboxylic acid carbamoylmethyl-amide, 3-(2-Amino-ethyl)-2-oxo-2,3-dihydro-1H-benzoimidazole-5-carboxylic acid (2-hydroxy-1-hydroxymethyl-ethyl)-amide, N-{2-[2-oxo-2,3-dihydro-benzoimidazol-1-yl]-ethyl}-guanidine, 3-(2-Amino-ethyl)-5-benzyloxy-1,3-dihydro-benzoimidazol-2-one, and 1-(4-Amino-butyl)-1,3-dihydro-benzoimidazol-2-one. Within one such embodiment, is provided the compound 3-(2-Amino-ethyl)-1-(2-isopropyl-5-methyl-cyclohexanecarbonyl)-5-methoxy-1,3-dihydro-benzoimidazol-2-one.

Synthesis of Small-Molecule Trp-p8 Modulators

As noted above, compounds of the present invention include compounds of Formula I, Formula I-A, Formula I-B, Formula I-C, Formula I-D, and Formula I-E. Within certain aspects, compounds can be made using commercially available starting materials by employing synthetic methodology readily available in the art. Compounds of Formula I, Formula I-A, Formula I-B, Formula I-C, Formula I-D, and Formula I-E may be isolated using typical isolation and purification techniques known in the art, including, for example, chromatographic and recrystallization methods.

Those of skill in the art will readily recognize that compounds suitably included in the compositions and methods of the present invention can exist in a number of cis and trans isomers, E/Z forms, diastereomers, as well as optical isomers.

Thus, compounds used in the compositions and methods of the present invention include all such combinations and variations.

In compounds of Formula I, Formula I-A, Formula I-B, Formula I-C, Formula I-D, and Formula I-E, carbon atoms to which four non-identical substituents are bonded are asymmetric. Accordingly, compounds of Formula I, Formula I-A, Formula I-B, Formula I-C, Formula I-D, and Formula I-E may exist as enantiomers, diastereomers or a mixture thereof. The enantiomers and diastereomers may be separated by chromatographic or crystallization methods, or by other methods known in the art. The asymmetric carbon atom may be in one of two configurations, R or S, both of which are within the scope of the present invention. The presence of small amounts of the opposing enantiomer or diastereomer in the final purified product does not affect the therapeutic application of such compounds.

Compounds of Formula I, Formula I-A, Formula I-B, Formula I-C, Formula I-D, and Formula I-E may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art, including those described herein above, may be used to effect the conversion to the salt.

The present invention also relates to pharmaceutically acceptable isomers, hydrates, and solvates of compounds of Formula I, Formula I-A, Formula I-B, Formula I-C, Formula I-D, and Formula I-E. Compounds of these formulae may also exist in various isomeric and tautomeric forms including pharmaceutically acceptable salts, hydrates and solvates of such isomers and tautomers.

This invention also encompasses prodrug derivatives of the compounds of Formula I, Formula I-A, Formula I-B, Formula I-C, Formula I-D, and Formula I-E. The term "prodrug" refers to a derivative of a parent drug molecule that requires biotransformation, either spontaneous or enzymatic, within the organism to release the parent drug. Prodrugs are variations or derivatives of the compounds of Formula I, Formula I-A, Formula I-B, Formula I-C, Formula I-D, and Formula I-E of the present invention that have groups cleavable under metabolic conditions. Prodrugs become the compounds of the invention which are pharmaceutically active in vivo when they undergo solvolysis under physiological conditions or undergo enzymatic degradation. An exemplary prodrug technology that may be suitably employed with the compounds of the present invention is the protease activated cancer therapy (PACT) technology described in detail within U.S. patent application Ser. No. 10/156,214 and PCT Application Publication No. WO 02/095007, both of which are incorporated herein by reference.

Synthesis of compounds of Formula I, Formula I-A, Formula I-B, Formula I-C, Formula I-D, and Formula I-E may be achieved by reacting an acid chloride, obtained by reacting p-menthane-3-carboxylic acid with thionyl chloride, with the appropriate amine. As noted below, typically, the reaction is carried out in solution at room temperature in the presence of a hydrogen chloride receptor (e.g., sodium hydroxide).

The basic p-menthane structure is a chair-shaped molecule that can exist in cis or trans form. Substitution of the carboxyl or amide group into the 3-position gives rise to four configurational or geometric isomers depending upon whether the substitution is axially or equatorially into the cis or trans isomer, the four isomers are related as menthol is to neomenthol, isomenthol, and neoisomenthol.

In exemplary embodiments, compounds of Formula I, Formula I-A, Formula I-B, Formula I-C, Formula I-D, and Formula I-E are synthesized with a particular stereochemistry wherein the relative stereochemistry about the menthane ring is that of Menthol and/or wherein the absolute stereochemistry about the menthane ring is that of (−)-Menthol.

Synthetic methods for the preparation of exemplary Formula I, Formula I-A, Formula I-B, Formula I-C, Formula I-D, and Formula I-E small-molecule Trp-p8 modulators of the present invention are presented herein in Examples 1-9.

Compositions Comprising Small-Molecule Trp-p8 Modulators

As discussed above, the present invention is directed to small-molecule Trp-p8 modulators, including Trp-p8 agonists and Trp-p8 antagonists that bind to and alter the activity of Trp-p8. Within certain embodiments, Trp-p8 modulators are agonists that are, in certain instances, capable of stimulating cation influx in, and toxicity of, a cell expressing the Trp-p8 channel protein. Within alternative embodiments, Trp-p8 modulators are antagonists of Trp-p8 activity that are capable of reducing the activity of Trp-p8 expressed in a cell. Thus, Trp-p8 modulators of the present invention will find utility in compositions, including pharmaceutical compositions, which are useful in the treatment of diseases associated with Trp-p8 expression. Suitable compositions, according to the present invention, comprise one or more Trp-p8 agonist of Formula I, Formula I-A, Formula I-B, Formula I-C, Formula I-D, and Formula I-E and/or one or more Trp-p8 antagonist of Formula I, Formula I-A, Formula I-B, Formula I-C, Formula I-D, and Formula I-E, as described above, in combination with one or more pharmaceutically acceptable carrier or excipient.

In one embodiment, the present invention provides small-molecule Trp-p8 modulators in combination with a pharmaceutically acceptable excipient such as sterile saline or other medium, water, gelatin, oil, etc., to form pharmaceutically acceptable compositions. The compositions and/or agonists may be administered alone or in combination with any convenient carrier, diluent, etc. and such administration may be provided in single or multiple dosages. Useful carriers include, but are not limited to, solid, semi-solid, or liquid medium including water and non-toxic organic solvents.

Pharmaceutical compositions of the present invention may be prepared by mixing one or more Trp-p8 agonist of Formula I, Formula I-A, Formula I-B, Formula I-C, Formula I-D, and/or Formula I-E with a pharmaceutically acceptable carrier or agent. Alternatively, pharmaceutical compositions may be prepared by mixing one or more Trp-p8 antagonist of Formula I, Formula I-A, Formula I-B, Formula I-C, Formula I-D, and/or Formula I-E with a pharmaceutically acceptable carrier or agent. In addition, pharmaceutical compositions may further include excipients, stabilizers, diluents and the like and may be provided in sustained release or timed release formulations. Acceptable carriers, agents, excipients, stabilizers, diluents and the like for therapeutic use are well known in the pharmaceutical field, and are described, for example, in "Remington's Pharmaceutical Sciences," (Mack Publishing Co., ed. A. R. Gennaro, 1985), incorporated herein by reference. Such materials are nontoxic to the recipients at the dosages and concentrations employed and include buffers such as phosphate, citrate, acetate, and other organic acid salts, antioxidants such as ascorbic acid, low molecular weight peptides such as polyarginine, proteins, such as serum albumin, gelatin, or immunoglobulin, hydrophilic polymers such as serum albumin, gelatin, or immunoglobulin, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Within still further aspects, the compositions of the present invention comprise a compound of Formula I, Formula I-A, Formula I-B, Formula I-C, Formula I-D, and/or Formula I-E formulated together with one or more cancer therapeutic agent. Alternatively, the compositions of the present invention comprise a compound of Formula I, Formula I-A, Formula I-B, Formula I-C, Formula I-D, and/or Formula I-E independently formulated with one or more cancer therapeutic agent. That is, the compound of Formula I, Formula I-A, Formula I-B, Formula I-C, Formula I-D, and/or Formula I-E and the cancer therapeutic agent are separately formulated.

Suitable cancer therapeutic agents include, but are not limited to, antimitotic agents including, but not limited to, paclitaxel, vincristine, and etoposide; alkylating agents including, but not limited to, mechlorethamine, cyclophosphamide, and carmustine; antimetabolites including, but not limited to, methotrexate, gemcitabine, lometrexol, 5-fluorouracil, and 6-mercaptopurine; cytotoxic antibiotics including, but not limited to, doxorubicin, daunorubicin, bleomycin, mitomycin C, and streptozocin; platinum agents including, but not limited to, cisplatin and carboplatin; hormonal agents including, but not limited to, anti-estrogens such as tamoxifen and diethylstilbestrol as well as anti-androgens such as flutamide; antiangiogenesis agents; and farnesyl transferase inhibitors.

In certain aspects, compounds of Formula I, Formula I-A, Formula I-B, Formula I-C, Formula I-D, and/or Formula I-E are administered in combination with a cancer therapeutic agent that is ineffective in stimulating Trp-p8-mediated cation influx.

In other aspects, compounds of Formula I, Formula I-A, Formula I-B, Formula I-C, Formula I-D, and/or Formula I-E are administered in combination with one or more additional Trp-p8 modulator including, but not limited to a compound of Formula I, Formula I-A, Formula I-B, Formula I-C, Formula I-D, and/or Formula I-E.

Depending upon the particular treatment regimen contemplated, pharmaceutical compositions of the present invention may be administered parenterally, topically, orally, or locally. In certain aspects, the pharmaceutical compositions are administered parenterally, e.g., intravenously, subcutaneously, intradermally, or intramuscularly. In one embodiment, the present invention provides compositions for parenteral administration that comprise a compound of the present invention, dissolved or suspended in a carrier such as an aqueous carrier.

For solid formulations, compounds may be admixed with conventional nontoxic solid carriers such as, for example, pharmaceutical grades of mannitol, lactose, starch, magnesium stearate, sodium saccharin, talcum, cellulose, glucose, sucrose, magnesium carbonate, and the like.

For aerosol administration, compounds of the present invention may be supplied in finely divided form along with a nontoxic surfactant and propellant. Exemplary such agents are the esters or partial esters of fatty acids containing from 6 to 22 carbon atoms, such as caproic, actanoic, lauric, palmitic, stearic, linoleic, olesteric, and oleic acids.

Compositions of the present invention may be administered by injection, i.e. intravenously, intramuscularly, intracutaneously, subcutaneously, introaduodenally, or intraperitoneally. Alternatively, compositions may be administered by inhalation, such as intranasally, and may be administered transdermally, such as through a patch or the like.

It will be understood that the actual preferred formulation of compositions, including pharmaceutical compositions, will vary according to the mode of administration as well as the particular disease being treated. The optimal formulations and modes of administration will be routinely determined on a disease by disease and patient by patient basis by those of skill in the art.

Methods for Identifying and Characterizing the In Vitro and In Vivo Efficacy of Small-Molecule Modulators of Trp-p8

As discussed above, the present invention is directed to small-molecule Trp-p8 modulators, including agonists and antagonists of Trp-p8 activity. Disclosed herein are Trp-p8 modulators exemplified by the compounds of Formula I, Formula I-A, Formula I-B, Formula I-C, Formula I-D, and/or Formula I-E described herein above. The present invention further contemplates that additional Trp-p8 modulators may also be suitably employed in the compositions and methods of the present invention.

Additional or alternative Trp-p8 agonists and antagonists may be identified by the methodology disclosed in the accompanying Examples. For instance, Trp-p8 agonists having efficacy in the treatment of disease(s) associated with Trp-p8 expression include small molecules that result in one or more of the following: (1) inhibit the growth or decrease the viability of a cell expressing Trp-p8; (2) stimulate calcium and/or other cation influx in a cell expressing Trp-p8; (3) induction of apoptosis and/or necrosis in a cell expressing Trp-p8; and/or (4) efficacy in one or more animal model systems of human disease. Trp-p8 antagonists having efficacy in the treatment of disease(s) associated with Trp-p8 expression include small molecules that result in one or more of the following: (1) protect Trp-p8 expressing cells from toxic effect of agonists in vitro model system (2) inhibit growth of and/or kill cancer cell line with endogenous Trp-p8 expression (3) are efficacious in one or more animal model systems of human disease.

Thus, within certain embodiments, the present invention provides methods for identifying Trp-p8 agonists comprising the step of contacting a Trp-p8 expressing cell with a candidate Trp-p8 agonist for a time and in an amount sufficient to inhibit the growth and/or decrease the viability of a Trp-p8 expressing cell, wherein the inhibited growth and/or reduced viability indicate that the candidate Trp-p8 agonist is capable of activating Trp-p8 expressed by the cell.

Other embodiments provide methods for identifying Trp-p8 agonists, comprising the step of contacting a Trp-p8 expressing cell with a candidate Trp-p8 agonist for a time and in an amount sufficient to induce influx of calcium and/or other cations into the cell, wherein increased cation influx is correlative of increased cellular toxicity.

Still further embodiments provide methods for identifying Trp-p8 agonists comprising the step of administering a candidate Trp-p8 agonist to an animal having one or more neoplastic cell that expresses Trp-p8 for a time and in an amount sufficient to inhibit the growth of and/or induce apoptosis and/or necrosis in the cell thereby increasing the survival of the animal, wherein any one or more of inhibition of cell growth, induction of apoptosis, induction of necrosis, and/or increased survival of the animal indicate efficacy of the Trp-p8 agonist.

The present invention provides methods for the identification of Trp-p8 antagonists in addition to the Trp-p8 antagonists disclosed herein. Such method include (1) in vitro assay systems for detecting the protection of Trp-p8 expressing cells from toxicity induced by Trp-p8 agonists; (2) in vitro and in vivo assay systems of detecting the inhibition of growth of a cancer cell and/or cancer cell line endogenously expressing Trp-p8; (3) in vivo animal model systems whereby one or more candidate Trp-p8 antagonist is administered to an animal having one or more neoplastic cell that expresses Trp-p8 for a time and in an amount sufficient to inhibit the growth of and/or induce apoptosis and/or necrosis in the cell thereby increasing the survival of the animal.

Methods for Use of Trp-p8 Modulators

Small-molecule Trp-p8 modulators of the present invention may be suitably employed in methods for modifying (i.e. activating or reducing) Trp-p8-mediated calcium influx in a cell and therapeutic methods for the treatment of one or more diseases associated with expression of Trp-p8. For example, and as noted above, it has been observed that abnormal Trp-p8 expression is associated with a neoplastic phenotype in a variety of cancerous tissues including breast, colon, lung, and prostate tissues. Tsavaler et al., *Cancer Research*, supra.

Thus, within certain embodiments are provided methods for activating Trp-p8-mediated calcium influx in a cell, such methods comprising the step of contacting the Trp-p8 expressing cell with an amount of a Trp-p8 agonist for a time sufficient to inhibit growth of the cell and/or to induce necrosis and/or apoptosis in the cell. Exemplary methods for activating Trp-p8 are provided within the Examples presented herein.

Other embodiments of the present invention provide therapeutic methods for the treatment of diseases associated with expression of Trp-p8, such methods comprising the step of administering to a mammal, typically a human, a therapeutically effective amount of a composition comprising a Trp-p8 agonist for a time sufficient to inhibit growth of the cell and/or to induce necrosis and/or apoptosis in the cell. As used herein, the phrase "therapeutically effective amount" refers to the amount of a compound that, when administered to a mammal for treating a disease, is sufficient to effect such treatment for the disease. The "therapeutically effective amount" will vary depending upon the compound, the disease, and its severity and the age, weight, etc., of the mammal to be treated.

As used herein, the terms "treat", "treating", and "treatment" include: (1) preventing the disease, i.e. causing the clinical symptoms of the disease not to develop in a mammal that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms.

While the frequency and dosage of treatment regimens will vary depending upon such factors as the disease and patient treated, compositions comprising one or more compound of Formula I, Formula I-A, Formula I-B, Formula I-C, Formula I-D, and/or Formula I-E are typically administered in the range of about 0.001 mg compound/kg body mass to about 1000 mg/kg. Typically, treatment is initiated with smaller dosages that are less than the optimum dose of the compound. Thereafter, the dosage may be increased until optimal effectiveness is achieved.

In most instances, administration of a composition(s) of the present invention is achieved by any method that ensures systemic exposure to the compound of Formula I, Formula I-A, Formula I-B, Formula I-C, Formula I-D, and/or Formula I-E. Thus, compositions may be administered orally, parenterally, intraduodenally, and intranasally. Typically, such compositions comprise one or more such compound in combination with one or more pharmaceutically acceptable carrier or diluent, as described in further detail herein above.

Other embodiments of the present invention provide combination therapies wherein one or more compound of Formula I, Formula I-A, Formula I-B, Formula I-C, Formula I-D, and/or Formula I-E is administered in conjunction with one or more cancer therapeutic agent, as described in further detail herein above, such as an antimitotic agent, an alkylating agent, an antimetabolite, a cytotoxic antibiotic, a platinum agent, a hormonal agent, and/or an antiandrogen. Still further embodiments of the present invention provide combination therapies wherein two or more compounds of Formula I, Formula I-A, Formula I-B, Formula I-C, Formula I-D, and/or Formula I-E are administered either simultaneously or sequentially to achieve the desired therapeutic outcome.

Thus, as used herein, the term "combination" means that at least two compounds can be delivered in a simultaneous manner, in combination therapy wherein the first compound is administered first, followed by the second compound, as well as wherein the second compound is delivered first, followed by the first compound. The desired result can be either a subjective relief of a symptom(s) or an objectively identifiable improvement in the recipient of the dosages.

The following examples are offered by way of illustration and not by way of limitation.

EXAMPLES

Example 1

Synthesis of Menthane-3-Carboxamide Compounds

This example discloses methodology for the synthesis of Menthane-3-carboxamide compounds.

Menthane-3-Carboxylic Acid

Water (300 ml) was placed in a 2-L Erlenmeyer flask with a large stir bar. Sulfuric acid (500 ml) was added carefully with stirring. The solution was allowed to cool to 75° C., and N-ethyl-p-menthane-3-carboxamide (62.5 g) was added. The temperature was maintained at 75° C. with a hot plate, and sodium nitrite (31 g) was added carefully. Two more 31 gram portions of $NaNO_2$ were added at 1-hour intervals, and the mixture was stirred overnight at 75° C.

The mixture was cooled to room temperature, diluted with ~1 L of ice water, and extracted with ~500 ml of ether. The ether layer was separated, washed with water, and extracted with 2×350 ml of 1M NaOH. The aqueous layer was made acidic with concentrated HCl and extracted with ether. The ether layer was dried with $MgSO_4$ and evaporated to give menthane-3-carboxylic acid (33.2 g, 61%) as a crystalline solid, =−50.3 deg (c=1, $CHCl_3$, 25° C.).

Menthane-3-Carbonyl Chloride

Menthane-3-carboxylic acid (54.35 g) was refluxed with 80 ml of thionyl chloride for 3 hours. The $SOCl_2$ was removed by distillation, and the acid chloride was distilled at 114-115° C. (8 Torr). (Lit. b.p. 84-85° C. at 3.5 Torr). Yield: 50 g (84%).

General Procedure for Preparation of Menthane-3-Carboxamides

To a stirred solution of 0.2 mmol of the amine in 1 ml of acetonitrile or NMP and 0.4 mmol of DIPEA was added 0.022 ml of menthane-3-carbonyl chloride. The reaction mixture was shaken for 3 hours. For less reactive amines, the mixture was heated (60° C.) and shaken for 24 hours. The product was purified from the crude reaction mixture by HPLC (40-95% gradient over 10 minutes using 0.05% TFA in $CH_3CN$ and 0.05% TFA in $H_2O$) and evaporated to dryness.

Example 2

Synthesis of Dihydrobenzoimidazol Compounds of Formula I-E

This example discloses methodology for the synthesis of dihydrobenzoimidazol Trp-p8 modulators of Formula I-E.

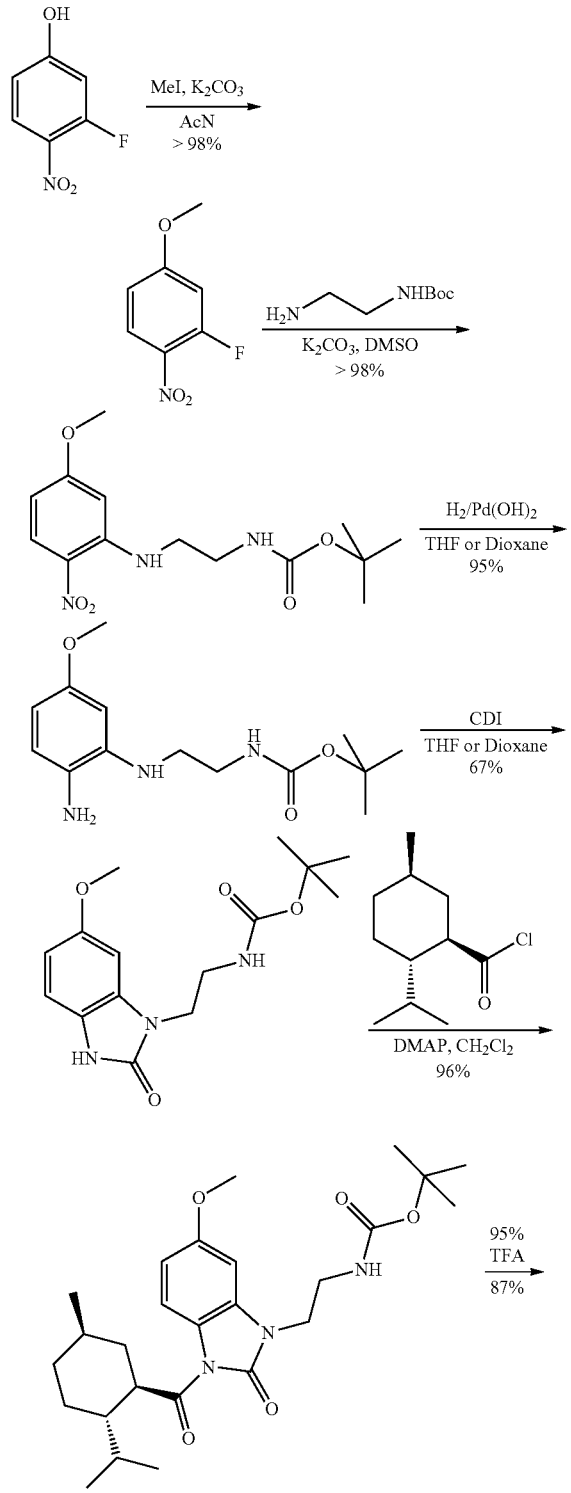

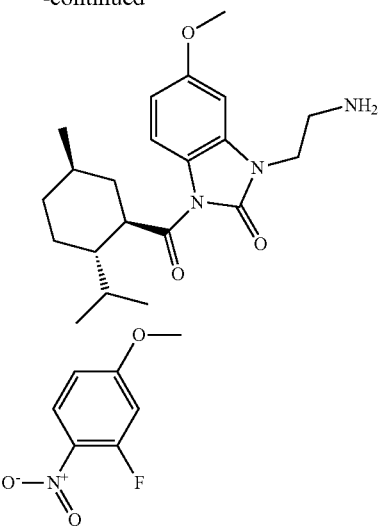

4-Methoxy-2-fluoro-1-nitrobenzene

A 2 L round bottom flask equipped with a stir bar and reflux condenser was charged with acetonitrile (1 L), $K_2CO_3$ (263 g, 1.9 mol) and 4-hydroxy-2-fluoro-1-nitrobenzene (100 g, 0.64 mol). Methyl iodide (271 g, 1.9 mol) was added to the reaction mixture and heated at reflux temperatures with vigorous stirring for 5 h. The acetonitrile was removed and ethyl acetate (1 L) and $H_2O$ (700 mL) were added. The heterogeneous mixture was transferred to a reparatory funnel where the aqueous phase was separated and re-extracted with ethyl acetate (2×200 mL). The organic phases were combined and washed with $H_2O$ (2×500 mL), brine (500 mL), dried over $MgSO_4$, filtered and concentrated under reduced pressure to give the desired product as a slightly yellow solid (107 g, 98%).

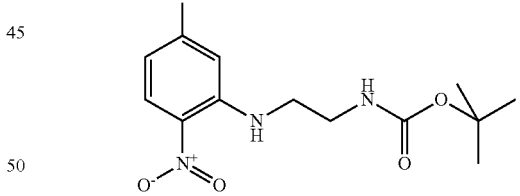

[2-(5-Methoxy-2-nitrophenylamino)-ethyl]-carbamic acid tert-butyl ester

A 2 L flask equipped with a stir bar was charged with DMSO (800 mL), $K_2CO_3$ (161 g, 1.6 mol) and 4-methoxy-2-fluoro-1-nitrobenzene (100 g, 0.58 mol). Mono-N-Boc-1,2-diaminoethane (94 g, 0.55 mol) was added to the reaction mixture and stirred for 12 h at 60° C. The reaction mixture was triturated with ice cold water (1.2 L) and the resulting yellow precipitate was collected by vacuum filtration. The precipitate was washed several times with water (5×1 L) and dried on a high vacuum for 48 h to give the desired product as a bright yellow solid (178 g, 98%.)

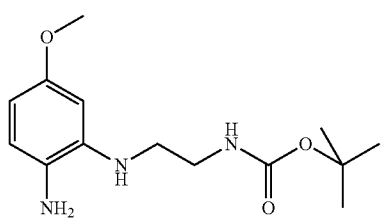

[2-(5-Methoxy-2-Amino-phenylamino)-ethyl]-carbamic acid tert-butyl ester

A 2 L round bottom flask equipped with a stir bar was charged with a suspension of 20% Pd(OH)$_2$ (5 g) and 1,4-dioxane (800 mL). [2-(5-Methoxy-2-nitrophenylamino)-ethyl]-carbamic acid tert-butyl ester (100 g, 0.32 mol) was added to the suspension. The reaction mixture was hydrogenated (balloon) for 48 h (until the starting material had been consumed) followed by the addition of K$_2$CO$_3$ (100 g) was added to the mixture and stirred for an additional 12 h to remove traces of water. The suspension was filtered to remove the Pd(OH)$_2$ and K$_2$CO$_3$. The filtrate was used in the next step without further purification (yield not determined).

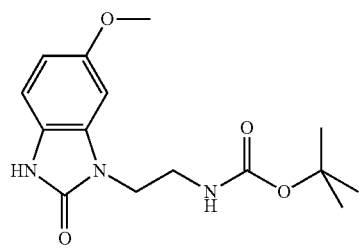 [SMILES: COc1ccc2[nH]c(=O)n(CCNC(=O)OC(C)(C)C)c2c1]

[2-(6-Methoxy-2-Oxo-2,3-dihydrobenzoimidazol-1-yl)-ethyl]-carbamic acid tert-butyl ester The above solution was treated with an excess of carbonyl diimidazole (104 g, 0.64 mol) and heated at 90° C. for 4 h. The 1,4-dioxane was removed and the residue was triturated with water (1.5 L). The resulting precipitate was collected by vacuum filtration and washed several times with water (5×500 mL). The crude product was dried at 70° C. on the high vacuum for 12 h and used without further purification (66 g, 67% yield for 2 steps).

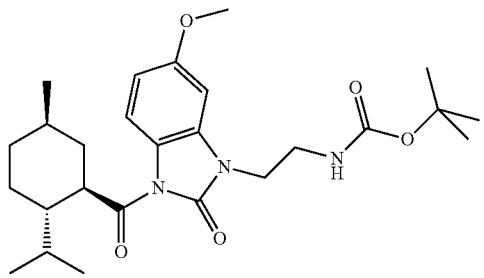 [SMILES: COc1ccc2c(c1)n(CCNC(=O)OC(C)(C)C)c(=O)n2C(=O)[C@@H]1C[C@H](C)CC[C@H]1C(C)C]

{2-[3-(2-Isopropyl-5-methylcyclohexanecarbonyl)-6-methoxy-2-oxo-2,3-dihydrobenzoimidazol-1-yl]-ethyl}-carbamic acid tert-butyl ester A 2 L flask equipped with a stir bar was charged with [2-(2-oxo-2,3-dihydrobenzoimidazol-1-yl)-ethyl]-carbamic acid tert-butyl ester (40 g, 0.20 mol), DMAP (48 g, 0.39 mol) and CH$_2$Cl$_2$ (500 mL). Menthoyl chloride (40 g, 0.20 mol) was added drop wise over a 15 minute period and stirred at an ambient temperature for 4 h. The reaction mixture was quenched with 1N HCl and stirred for an additional 20 min. The heterogeneous mixture was transferred to a separation funnel where the aqueous phase was separated and re-extracted with CH$_2$Cl$_2$ (2×200 mL). The organic phases were combined and washed with 1N HCl (2×300 mL), H$_2$O (300 mL), saturated NaHCO$_3$ (aq) (2×300 mL), brine (300 mL), dried over MgSO$_4$, filtered and concentrated under reduced pressure. The crude product was dissolved in a minimal amount of CH$_2$Cl$_2$ and eluted through a plug of silica gel (10% hexane/ethyl acetate for elution) to furnish the desired product as a colorless solid (93 g, 96%).

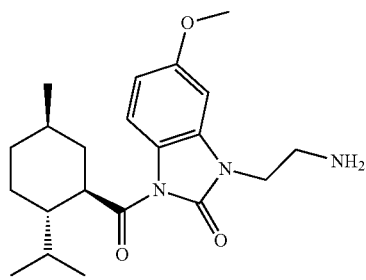 [SMILES: COc1ccc2c(c1)n(CCN)c(=O)n2C(=O)[C@@H]1C[C@H](C)CC[C@H]1C(C)C]

TFA salt of 3-(2-Aminoethyl)-1-(2-isopropyl-5-methylcyclohexanecarbonyl)-5-methoxy-1,3-dihydrobenzoimidazol-2-one (Compound #36)

A 500 mL round bottom flask was charged with {2-[3-(2-Isopropyl-5-methylcyclohexanecarbonyl)-2-oxo-2,3-dihydrobenzoimidazol-1-yl]-ethyl}-carbamic acid tert-butyl ester (90 g, 0.19 mol) and 95% TFA/H$_2$O (200 mL). The reaction was stirred for 2 h. and the TFA was removed under reduced pressure to give the crude product as a thick oil (which solidifies to form fragile foam upon standing under vacuum). The crude product was dissolved in 30% acetonitrile/H$_2$O and purified by preparative HPLC (Ultro 120 (10 um) C18Q) using a 40-60% acetonitrile/H$_2$O (with 0.1% TFA) gradient. The pure fractions were combined, concentrated and lyophilized to give a light fluffy colorless solid (79 g, 94%). MS (ESI) m/z 374 (M$^+$+1).

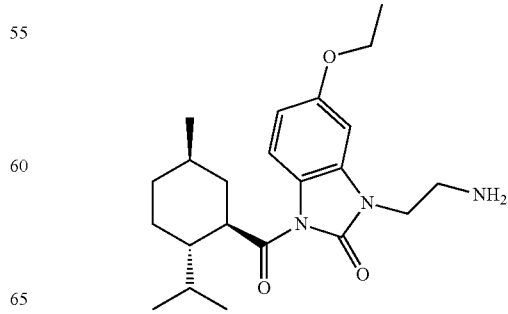

TFA salt of 3-(2-Aminoethyl)-5-ethoxy-1-(2-isopropyl-5-methylcyclohexanecarbonyl)-1,3-dihydro-benzoimidazol-2-one (Compound #38)

In a procedure similar to the synthesis of Compound #36, Compound #38 was prepared from 4-ethoxy-1-2-fluoro-1-nitrobenzene (prepared from ethyl bromide and 4-hydroxy-2-fluoro-1-nitrobenzene. MS (ESI) m/z 387 (M$^+$+1).

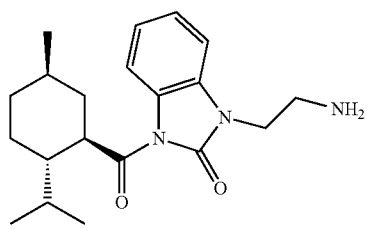 [SMILES: CC(C)[C@@H]1CC[C@@H](C)C[C@H]1C(=O)n1c(=O)n(CCN)c2ccccc21]

TFA salt of 1-(2-Aminoethyl)-3-(2-isopropyl-5-methylcyclohexanecarbonyl)-1,3-dihydro-benzoimidazol-2-one (Compound #50)

In a procedure similar to the synthesis of Compound #36, Compound #50 was prepared from 2-fluoro-1-nitrobenzene. MS (ESI) m/z 344 (M$^+$+1).

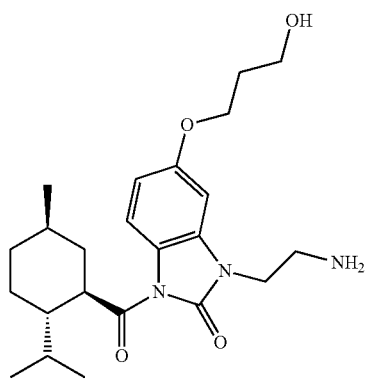 [SMILES: CC(C)[C@@H]1CC[C@@H](C)C[C@H]1C(=O)n1c(=O)n(CCN)c2cc(OCCCO)ccc21]

TFA salt of 3-(2-aminoethyl)-5-(3-hydroxypropoxy)-1-(2-isopropyl-5-methylcyclohexanecarbonyl)-1,3-dihydro-benzoimidazol-2-one (Compound #37)

In a procedure similar to the synthesis of Compound #36, Compound #37 was prepared from 4-(2-tert-butoxypropoxy)-2-fluoro-1-nitrobenzene (prepared from 1-bromo-3-tert-butoxy propane and 4-hydroxy-2-fluoro-1-nitrobenzene). MS (ESI) m/z 418 (M$^+$+1).

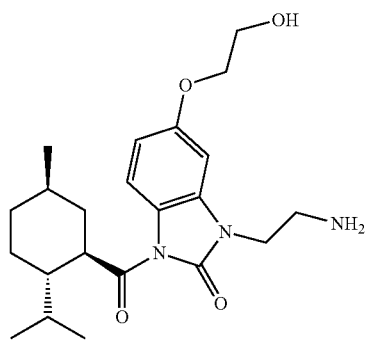 [SMILES: CC(C)[C@@H]1CC[C@@H](C)C[C@H]1C(=O)n1c(=O)n(CCN)c2cc(OCCO)ccc21]

TFA salt of 3-(2-aminoethyl)-5-(2-hydroxyethoxy)-1-(2-isopropyl-5-methylcyclohexanecarbonyl)-1,3-dihydro-benzoimidazol-2-one (Compound #40)

In a procedure similar to the synthesis of Compound #36, Compound #40 was prepared from 4-(2-tert-butoxyethoxy)-2-fluoro-1-nitrobenzene (prepared from 1-bromo-3-tert-butoxy ethane and 4-hydroxy-2-fluoro-1-nitrobenzene). MS (ESI) m/z 404 (M$^+$+1).

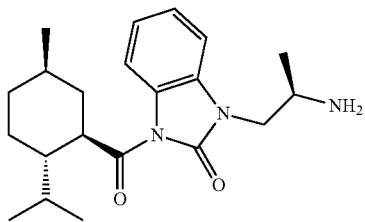 [SMILES: CC(C)[C@@H]1CC[C@@H](C)C[C@H]1C(=O)n1c(=O)n(C[C@@H](C)N)c2ccccc21]

TFA salt of 1-(2-Amino-2-(R)-methylethyl)-3-(2-isopropyl-5-methylcyclohexanecarbonyl)-1,3-dihydro-benzoimidazol-2-one (Compound #45)

In a procedure similar to the synthesis of Compound #36, Compound #45 was prepared from 2-fluoro-1-nitrobenzene and (2-amino-1-(R)-ethyl)carbamic acid tert-butyl ester. MS (ESI) m/z 358 (M$^+$+1).

Example 3

Synthesis of Additional Dihydrobenzoimidazole Compounds of Formula I-E

This example discloses methodology for the synthesis of dihydrobenzoimidazole Trp-p8 modulators of Formula I-E.

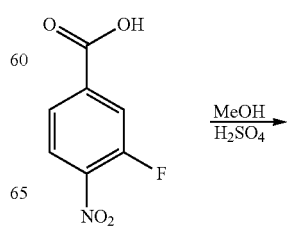

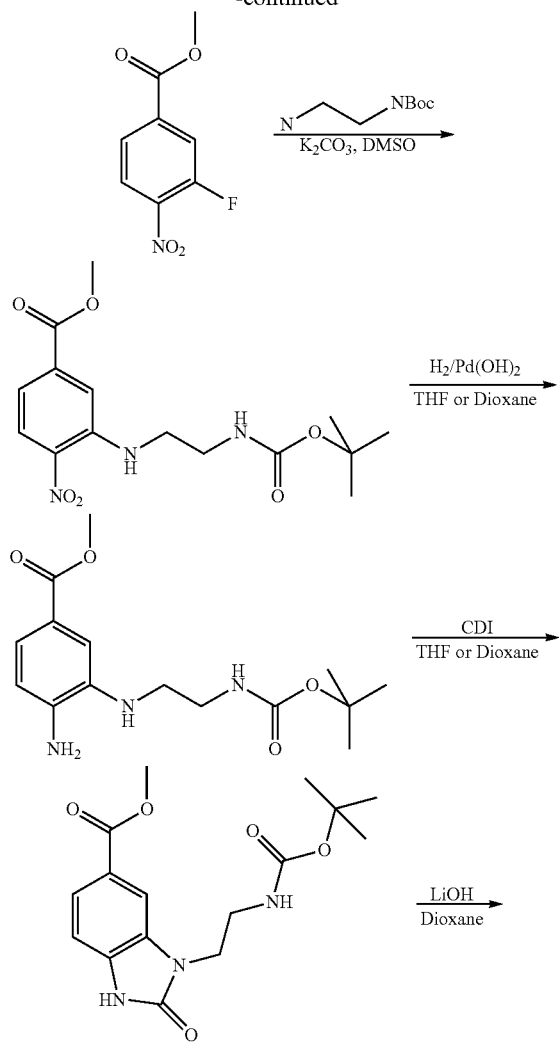

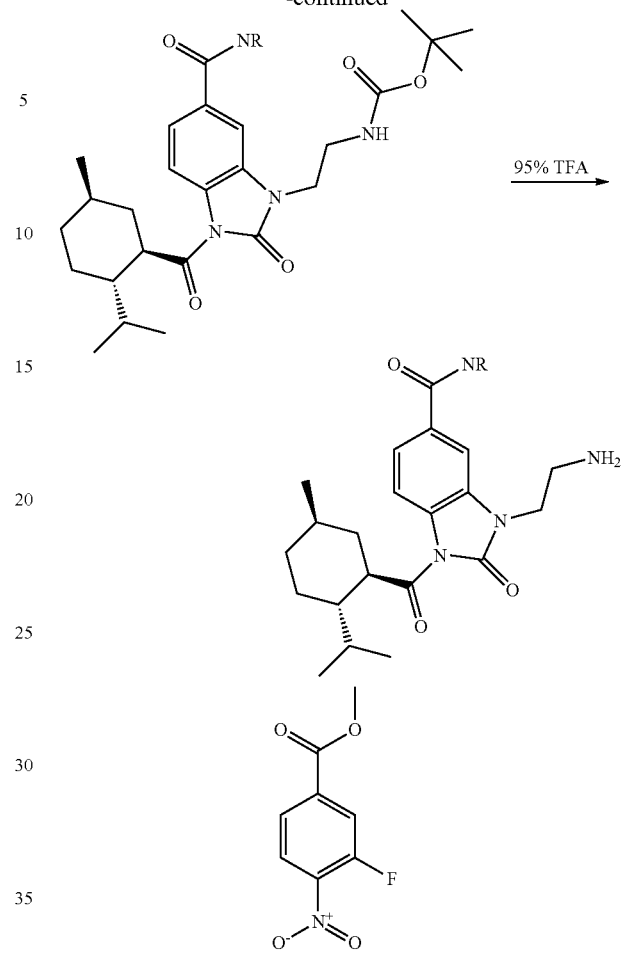

3-Fluoro-4-Nitrobenzoic Acid Methyl Ester

A 1 L round bottom flask equipped with a stir bar and reflux condenser was charged $H_2SO_4$ (4 mL), methanol (400 mL) and 3-fluoro-4-nitrobenzoic acid (10 g). The reaction mixture was heated at reflux temperatures with vigorous stirring for 18 h. The methanol was removed and the crude residue was triturated with hexane and concentrated to give a colorless solid (9.79 g) that was used without further purification.

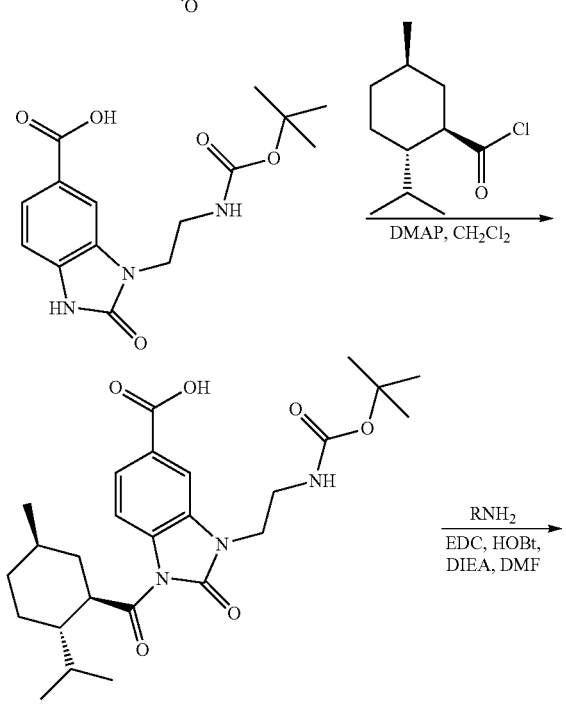

3-(2-tent-Butyoxycarbonylaminoethylamino)-4-nitrobenzoic acid methyl ester

A 2 L flask equipped with a stir bar was charged with 1,4-dioxane (300 mL), DMF (40 mL), $K_2CO_3$ (10 g) and 3-fluoro-4-nitrobenzoic acid (9.7 g). Mono-N-Boc-1,2-diaminoethane (8.6 g) was added to the reaction mixture and stirred for 12 h at 60° C. The reaction mixture was concentrated and the residue was dissolved in CH₂Cl₂ (400 mL) and H₂O (500 mL). The heterogeneous mixture was transferred to a separatory funnel where the aqueous phase was separated and re-extracted with CH₂Cl₂ (2×100 mL). The organic phases were combined and washed with H₂O (5×100 mL), dried over Na₂SO₄, filtered and concentrated under reduced pressure to provide the title compound as an orange solid (14 g, 84%).

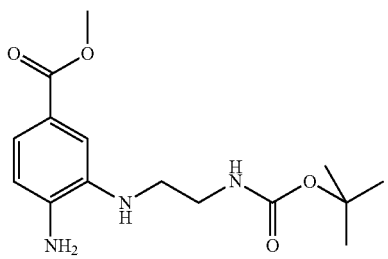 [SMILES: COC(=O)c1ccc(N)c(NCCNC(=O)OC(C)(C)C)c1]

4-Amino-3-(2-tert-butoxycarbonylamino-ethylamino)-benzoic acid methyl ester

A 2 L round bottom flask equipped with a stir bar was charged with a suspension of 20% Pd(OH)₂ and 1,4-dioxane (400 mL). 4-Amino-3-(2-tert-butoxycarbonylamino-ethylamino)-benzoic acid methyl ester (14 g) was added to the suspension. The reaction mixture was hydrogenated (balloon) for 48 h (until the starting material had been consumed) followed by the addition of K₂CO₃ (100 g) was added to the mixture and stirred for an additional 12 h to remove traces of water. The suspension was filtered to remove the Pd(OH)₂ and K₂CO₃. The filtrate was used in the next step without further purification.

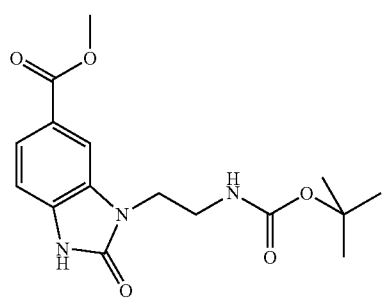 [SMILES: COC(=O)c1ccc2[nH]c(=O)n(CCNC(=O)OC(C)(C)C)c2c1]

3-(2-tert-Butoxycarbonylaminoethyl)-2-oxo-2,3-dihydro-1H-benzoimidazole-5-carboxylic acid methyl ester The above solution was treated with an excess of carbonyl diimidazole (26.8 g, 4 eq.) and heated at 90° C. for 4 h. The 1,4-dioxane was removed and the residue was triturated with water (1.5 L). The resulting precipitate was collected by vacuum filtration and washed several times with water (5×500 mL). The crude product was dissolved in a minimal amount of CH₂Cl₂ and purified by flash chromatography on silica gel (10% methanol/CH₂Cl₂ for elution) to furnish the desired product as an off white solid (11.8 g, 85%).

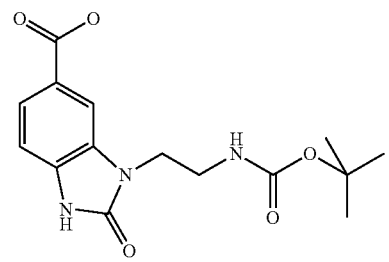 [SMILES: CC(C)(C)OC(=O)NCCn1c(=O)[nH]c2ccc(C(=O)O)cc21]

3-(2-tert-Butoxycarbonylaminoethyl)-2-oxo-2,3-dihydro-1H-benzoimidzole-5-carboxylic acid A 2 L flask equipped with a stir bar was charged with 1,4-dioxane (70 mL), 3-(2-tert-butoxycarbonylaminoethyl)-2-oxo-2,3-dihydro-1H-benzoimidazole-5-carboxylic acid methyl ester (10.4 g) and LiOH (3.7 g) dissolved in H₂O (300 mL). The reaction solution was stirred for 6 h at 65° C. The mixture was concentrated and the crude residue was dissolved in H₂O. The solution was neutralized with conc. HCl (aq.) and the resulting precipitate was collected by vacuum filtration. The solid was washed several times with H₂O and dried on the high vacuum overnight to provide the desired product as a white solid (8.66 g, 87%).

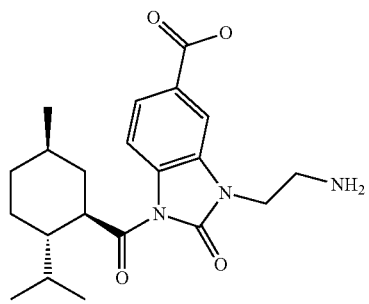 [SMILES: CC(C)[C@@H]1CC[C@@H](C)C[C@H]1C(=O)n1c(=O)n(CCN)c2cc(C(=O)O)ccc21]

TFA salt of 3-(2-Amino-ethyl)-1-(2-isopropyl-5-methylcyclohexanecarbonyl)-2-oxo-2,3-dihydro-1H-benzoimidazol-5-carboxylic acid In a 100 mL reaction vessel equipped with stir bar was charged with THF (20 mL), DMAP (1.8 g) and 3-(2-tert-Butoxycarbonylaminoethyl)-2-oxo-2,3-dihydro-1H-benzoimidzole-5-carboxylic acid (4 g). The reaction mixture was cooled to 0° C. and treated with menthoyl chloride (2.9 g). The reaction mixture was allowed to warm to ambient temperature and concentrated. 1N HCl (aq) (50 mL) and CH₂Cl₂ (50 mL) was added. The heterogeneous mixture was transferred to a reparatory funnel where the aqueous phase was separated and re-extracted with ethyl acetate (2×100 mL). The organic phases were combined and washed with 1N HCl (2×50 mL), H₂O (50 mL), brine (100 mL), dried over MgSO₄, filtered and concentrated under reduced pressure. The residue was purified by flash chromatography on silica gel (4:1 CH₂Cl₂/THF for elution) provided the title compounds as colorless solid (3.2 g, 52%).

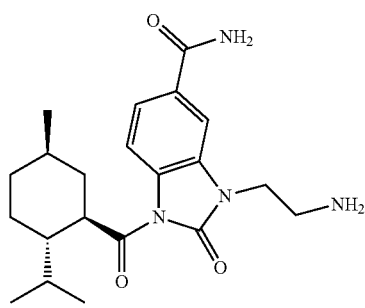 [SMILES: CC(C)[C@@H]1CC[C@@H](C)C[C@H]1C(=O)n1c(=O)n(CCN)c2cc(C(N)=O)ccc21]

TFA salt of 3-(2-Amino-ethyl)-1-(2-isoprophyl-5-methyl-cyclohexanecarbonyl)-2-oxo-2,3-dihydro-1H-benoimidazole-5-carboxylic acid amide (Compound #41)

In a 10 mL reaction vessel equipped with stir bar was charged with DMF (5 mL), 3-(2-amino-ethyl)-1-(2-isopropyl-5-methylcyclohexanecarbonyl)-2-oxo-2,3-dihydro-1H-benzoimidazol-5-carboxylic acid (1.5 g, 3.9 mmol), EDC (824 mg, 4.3 mmol), HOBt (581 mg, 4.3 mmol), DIEA (1.11 g, 8.6 mmol) and $NH_4Cl$ (230 mg, 4.3 mmol). The reaction mixture was heated via microwave at 60° C. for 10 min and poured into a mixture of ethyl acetate (50 mL) and 1N HCl (50 mL). The heterogeneous mixture was transferred to a separatory funnel where the aqueous phase was separated and re-extracted with ethyl acetate (2×50 mL). The organic phases were combined and washed with 1N HCl (100 mL), $H_2O$ (2×100 mL), sat. $NaHCO_3$ (3×100 mL), brine (100 mL), dried over $MgSO_4$, filtered and concentrated under reduced pressure. The residue was dissolved in 95% $TFA/H_2O$ and stirred for 2 h and concentrated. The crude product was dissolved in 30% acetonitrile/$H_2O$ and purified by preparative HPLC (Ultro 120 (10 um) C18Q) using a 10-60% acetonitrile/$H_2O$ (with 0.1% TFA) gradient. The pure fractions were combined, concentrated and lyophilized to give a light fluffy colorless solid (910 mg, 61%). MS (ESI) m/z 387 ($M^++1$).

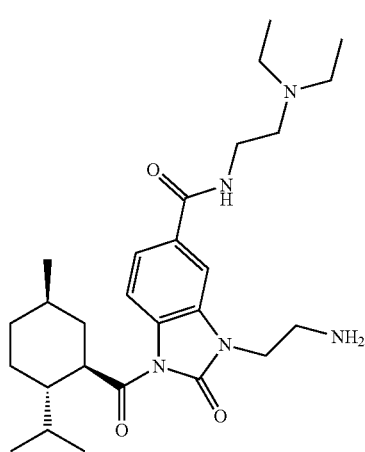 [SMILES: CCN(CC)CCNC(=O)c1ccc2c(c1)n(CCN)c(=O)n2C(=O)[C@@H]1C[C@H](C)CC[C@H]1C(C)C]

TFA salt of 3-(2-Amino-ethyl)-1-(2-isopropyl-5-methylcyclohexanecarbonyl)-2-oxo-2,3-dihydro-1H-benzoimidazole-5-carboxylic acid (2-diethylamino-ethyl)amide (Compound #44)

In a procedure similar to the synthesis of Compound #41, Compound #44 was prepared from $N^1,N^1$-Diethylethan-1,2-diamine. MS (ESI) m/z 486 ($M^++1$).

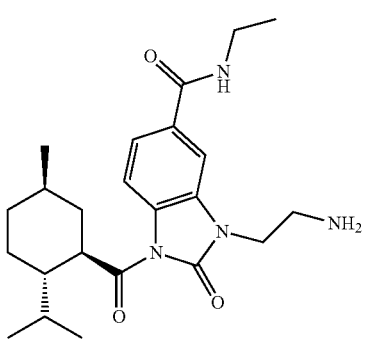 [SMILES: CCNC(=O)c1ccc2c(c1)n(CCN)c(=O)n2C(=O)[C@@H]1C[C@H](C)CC[C@H]1C(C)C]

TFA salt of 3-(2-Amino-ethyl)-1-(2-isopropyl-5-methylcyclohexanecarbonyl)-2-oxo-2,3-dihydro-1H-benzoimidazole-5-carboxylic acid ethyl amide (Compound #47)

In a procedure similar to the synthesis of Compound #41, Compound #47 was prepared from ethyl amine. MS (ESI) m/z 415 ($M^++1$).

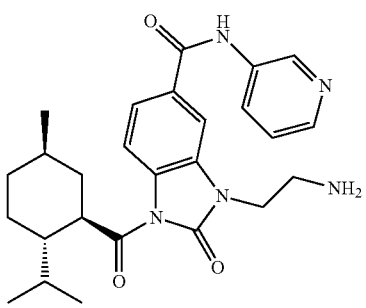 [SMILES: CC(C)[C@@H]1CC[C@@H](C)C[C@H]1C(=O)n1c(=O)n(CCN)c2cc(C(=O)Nc3cccnc3)ccc21]

TFA salt of 3-(2-Amino-ethyl)-1-(2-isopropyl-5-methylcyclohexanecarbonyl)-2-oxo-2,3-dihydro-1H-benzoimidazole-5-carboxylic acid pyridine-3-yl amide (Compound #48)

In a procedure similar to the synthesis of Compound #41 Compound #48 was prepared from pyridine-3-ylamine. MS (ESI) m/z 464 ($M^++1$).

Example 4

Synthesis of Additional Dihydrobenzoimidazole Compounds of Formula I-E

This example discloses methodology for the synthesis of dihydrobenzoimidazole Trp-p8 modulators of Formula I-E.

[2-(5-Methyl-sulfanyl-2-nitro-phenylamino)-ethyl]-carbamic acid tert-butyl ester In a 1 liter round bottom flask equipped with a stir bar was charged with DMSO (200 mL), $K_2CO_3$ (13 g, 0.10 mol) and 2,4-difluoro-1-nitrobenzene (5 g, 0.03 mol). The reaction mixture was treated with Mono-N-Boc-1,2-diaminoethane (5

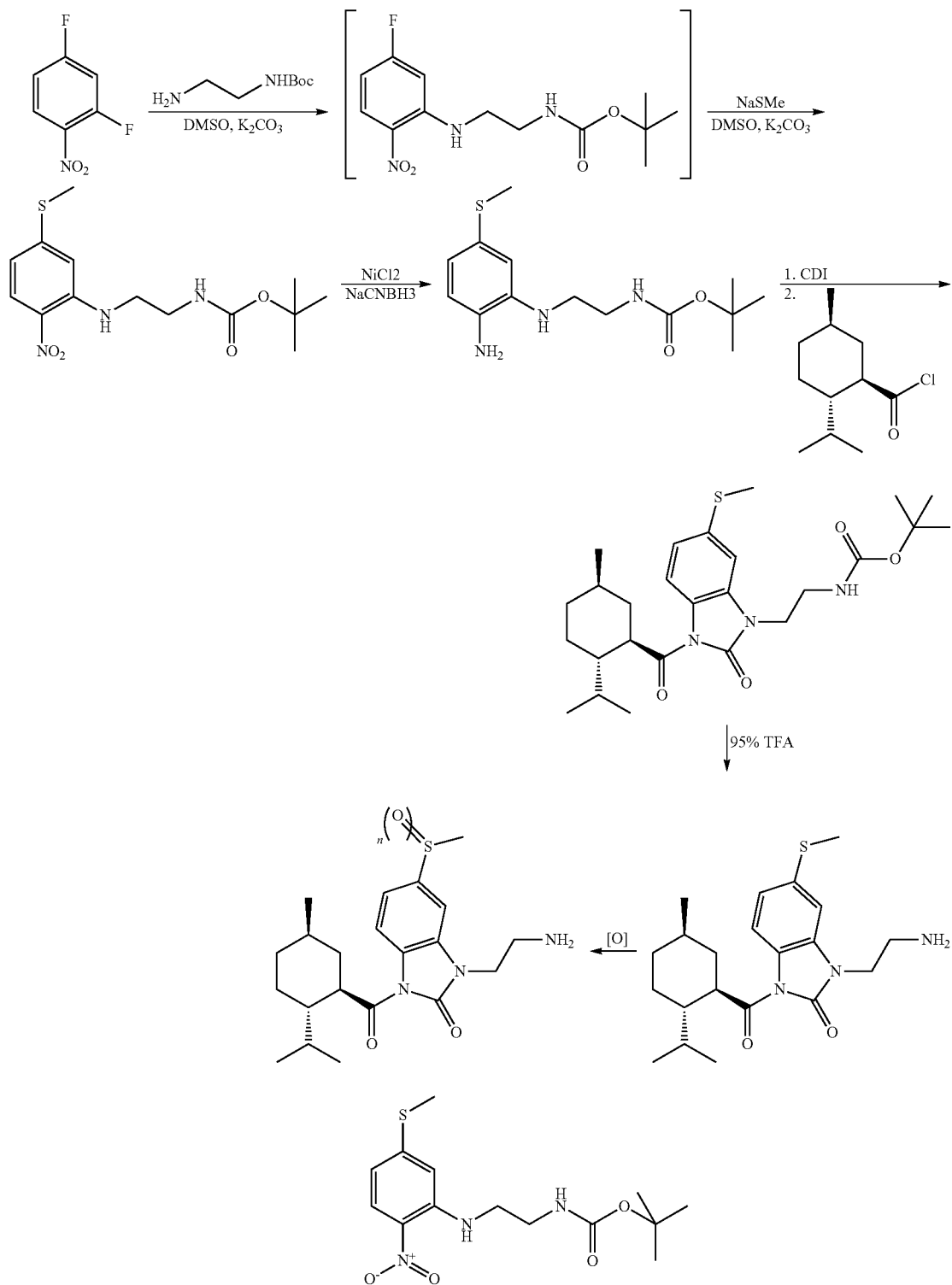

g, 0.32 mol) and stirred at ambient temperature for 18 h. Sodium thiomethoxide (2.24 g, 0.03 mol) was added to the reaction mixture and stirred for 12 h at 60° C. The reaction mixture was cooled to 0° C. and triturated with water (800 mL) and the yellow precipitate that formed was collected by vacuum filtration. The precipitate was washed several times with water (5×500 mL) and dried on a high vacuum for 48 h to give the desired product as a bright yellow solid (8.7 g, 71%).

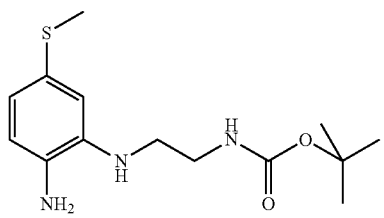

[2-(2-amino-5-Methyl-sulfanyl-phenylamino)-ethyl]-carbamic acid tert-butyl ester In a 500 mL round bottom flask equipped with a stir bar was charged with MeOH (200 mL), [2-(5-methyl-sulfanyl-2-nitro-phenylamino)-ethyl]-carbamic acid tert-butyl ester (5 g, 0.02 mol) and NiCl$_2$ (19 g, 0.05 mol) and cooled to 0° C. NaBH$_4$ (1.7 g, 0.05 mol) was added (in four equal portions) to the reaction mixture over a 1 h period. Once the addition was complete the reaction mixture was stirred for an additional 2 h. Brine (100 mL) and ethyl acetate (200 mL) were added to the reaction mixture. The heterogeneous mixture was transferred to a separatory funnel where the aqueous phase was separated and re-extracted with ethyl acetate (2×100 mL). The organic phases were combined and washed with H$_2$O (3×100 mL), brine (100 mL), dried over MgSO$_4$, filtered and concentrated under reduced pressure to give a black residue. The crude product was dissolved in 100 mL of CH$_2$Cl$_2$ and separated into two 100 mL round (50 mL in each) and both were concentrated under reduced pressure and used without further purification.

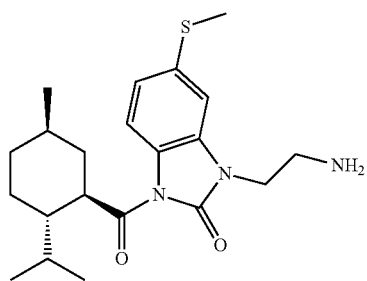 [SMILES: CSc1ccc2c(c1)n(CCN)c(=O)n2C(=O)[C@@H]1C[C@H](C)CC[C@H]1C(C)C]

3-(2-Amino-ethyl)-1-(2-isopropyl-5-methyl-cyclohexanecarbonyl)-5-methylsulfanyl-1,3-dihydro-benzoimidazol-2-one (Compound #42)

In a procedure similar to the synthesis of Compound #36, Compound #42 was prepared from the crude [2-(2-amino-5-Methyl-sulfanyl-phenylamino)-ethyl]-carbamic acid tert-butyl ester. MS (ESI) m/z 390.1 (M$^+$+1).

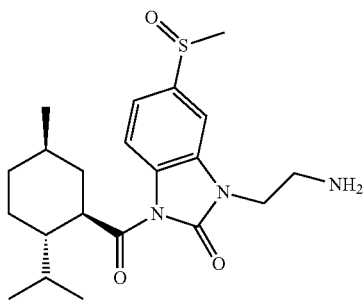 [SMILES: CC(C)[C@@H]1CC[C@@H](C)C[C@H]1C(=O)n1c(=O)n(CCN)c2cc(S(C)=O)ccc21]

3-2-Amino-ethyl)-1-(2-isopropyl-5-methyl-cyclohexanecarbonyl)-5-methylsulfinyl-1,3-dihydro-benzoimidazol-2-one (Compound #43)

A 10 mL reaction flask was charged with 3-(2-Amino-ethyl)-1-(2-isopropyl-5-methyl-cyclohexanecarbonyl)-5-methylsulfanyl-1,3-dihydro-benzoimidazol-2-one (Compound #42, 300 mg) and 1% TFA/DMSO (1 mL). Oxygen was bubbled through the reaction mixture for 20 min and sealed. The reaction mixture was stirred for 18 h and crude product was purified by preparative HPLC (Ultro 120 (10 um) C18Q) using a 40-60% acetonitrile/H$_2$O (with 0.1% TFA) gradient. The pure fractions were combined, concentrated and lyophilized to give a light fluffy colorless solid (296 mg 94%). MS (ESI) m/z 406 (M$^+$+1).

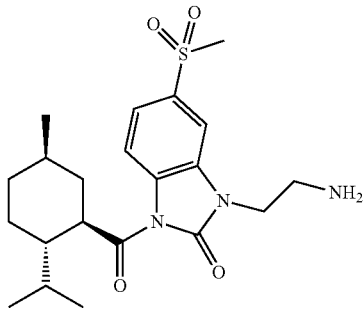 [SMILES: CC(C)[C@@H]1CC[C@@H](C)C[C@H]1C(=O)n1c(=O)n(CCN)c2cc(S(C)(=O)=O)ccc21]

3-2-Amino-ethyl)-1-(2-isopropyl-5-methyl-cyclohexanecarbonyl)-5-methylsulfonyl-1,3-dihydro-benzoimidazol-2-one (Compound #39)

A 10 mL reaction vessel equipped with a stir bar was charged with 3-(2-amino-ethyl)-1-(2-isopropyl-5-methyl-cyclohexanecarbonyl)-5-methylsulfanyl-1,3-dihydro-benzoimidazol-2-one (Compound #42), Oxone (1 g) and 20% aqueous methanol (5 mL). The reaction mixture is titrated with sat. NaHCO$_3$ (aq) to a pH of ~5. Reaction mixture is stirred for 1 h. The reaction mixture is filtered and concentrated. The crude product was dissolved in 30% acetonitrile/H$_2$O and purified by preparative HPLC (Ultro 120 (10 um) C18Q) using a 15-50% acetonitrile/H$_2$O (with 0.1% TFA) gradient. The pure fractions were combined, concentrated and lyophilized to give a fluffy colorless solid (79 g, 94%). MS (ESI) m/z 422 (M$^+$+1).

Example 5

Synthesis of Compounds of Formula I-B

This example discloses methodology for the synthesis of dihydrobenzoimidazole Trp-p8 modulators of Formula I-A

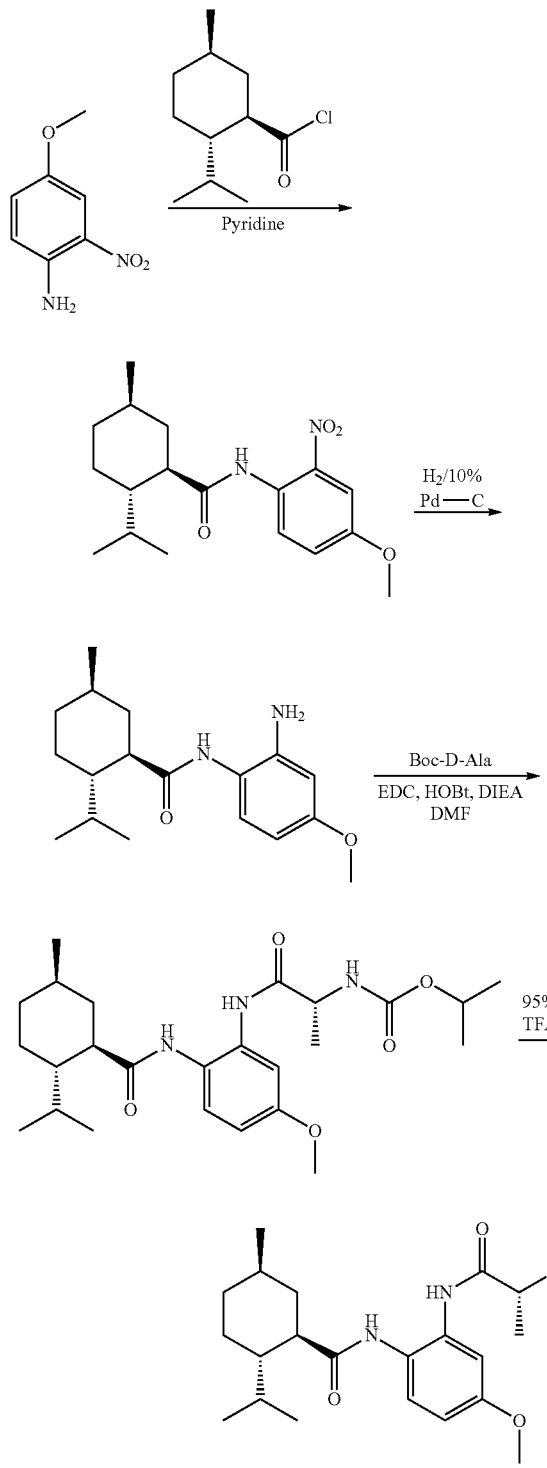

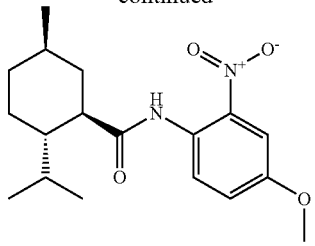

2-Isopropyl-5-methyl-cyclohexanecarboxylic acid (4-methoxy-2-nitrophenyl)-amide 4-Methoxy-2-nitroaniline (5 g, 0.018 mol) was dissolved in pyridine (50) and treated with menthoyl chloride (3.57 g, 0.018 mol). The reaction mixture was heated to 50° C. and stirred vigorously for 6 h. The reaction mixture was cooled to room temperature and poured into a mixture of $CH_2Cl_2$ (100 mL) and 1N HCl (100 mL)). The heterogeneous mixture was transferred to a reparatory funnel where the aqueous phase was separated and re-extracted with $CH_2Cl_2$ (2×100 mL). The organic phases were combined and washed with 1N HCl (8×100 mL), $H_2O$ (1×100 mL), 1N NaOH (2×100 mL), brine (100 mL), dried over $MgSO_4$, filtered and concentrated under reduced pressure. The residue was purified by flash chromatography on silica gel (20 to 50% ethyl acetate/hexane for elution) provided the title compounds as colorless solid (4.9 g, 83%).

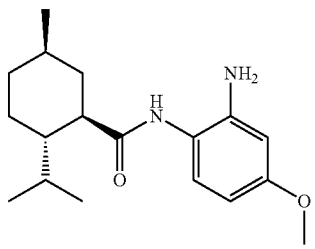 [SMILES: COc1ccc(NC(=O)[C@@H]2C[C@H](C)CC[C@H]2C(C)C)c(N)c1]

2-Isopropyl-5-methyl-cyclohexanecarboxylic (2-amino-4-methoxyphenyl)-amide

2-Isopropyl-5-methyl-cyclohexanecarboxylic acid (4-methoxy-2-nitrophenyl)-amide (4.9 g) was dissolved in a suspension of 10% Pd—C (5 g) and THF (150 mL). The reaction mixture was hydrogenated over 20% $Pd(OH)_2$ for 48 h with a balloon. The reaction mixture was filtered and concentrated to give the desired compound in sufficient purity to use in the next reaction without further purification.

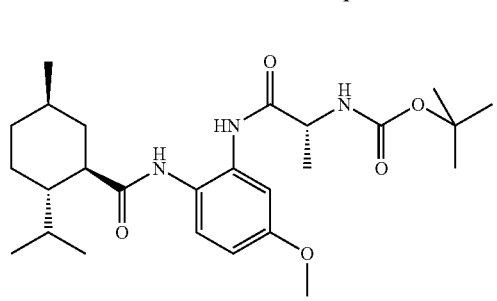

(1-{2-[2-Isopropyl-5-methyl-cyclohexanecarbonyl)-amino]-5-methoxy-phenylcarbamoyl}-ethyl)carbamic acid tert-butyl ester 2-Isopropyl-5-methyl-cyclohexanecarboxylic (2-amino-4-methoxyphenyl)-amide (5 g, 0.016 mol), EDC (4.2 g, 0.022 mol), HOBt (2.97 g, 0.022 mol) and DIEA (8.53 g, 0.066 mol) were dissolved in DMF (50 mL) and stirred at 45° C. for 6 h. The reaction mixture was cooled to room temperature and poured into a mixture of ethyl acetate and 1N HCl (100 mL). The heterogeneous mixture was transferred to a reparatory funnel and the phases where separated. The aqueous phase re-extracted with ethyl acetate ( ) and the organic phases where combined, washed with 1N HCl (5×100 mL), H$_2$O (100 mL), saturated 1N NaOH (2×100 mL), brine (100 mL), dried (MgSO$_4$), filtered and concentrated to give a slightly yellow solid (7.5 g). A portion of the crude product (1.5 g) was purified by flash chromatography with silica gel (SiO$_2$, 30% ethyl acetate/hexane for elution) to give the desired product as a colorless solid (1.6 g).

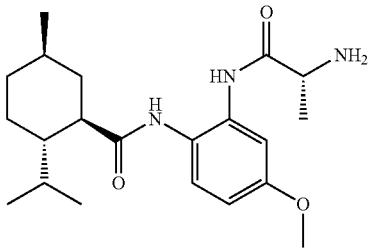 [SMILES: COc1ccc(NC(=O)[C@@H]2C[C@H](C)CC[C@H]2C(C)C)c(NC(=O)[C@@H](C)N)c1]

TFA salt of 2-Isopropyl-5-methyl-cyclohexanecarboxylic acid-[2-(2-aminopropionylamino)-4-methoxylphenyl]amide (Compound #1)

(1-{2-[2-Isopropyl-5-methyl-cyclohexanecarbonyl)-amino]-5-methoxy-phenylcarbamoyl}-ethyl)carbamic acid tert-butyl ester (1 g) was dissolved in 95% TFA/H$_2$O and stirred for 1 h. The reaction mixture was concentrated and the crude product was dissolved in 30% acetonitrile/H$_2$O and purified by preparative HPLC (Ultro 120 (10 um) C18Q) using a 40-60% acetonitrile/H$_2$O (with 0.1% TFA) gradient. The pure fractions were combined, concentrated and lyophilized to give a light fluffy colorless solid (880 mg) MS (ESI) m/z 376 (M$^+$+1).

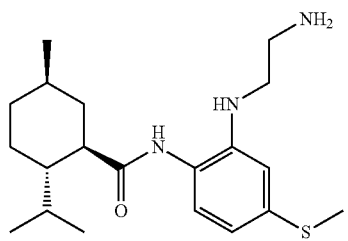 [SMILES: CSc1ccc(NC(=O)[C@@H]2C[C@H](C)CC[C@H]2C(C)C)c(NCCN)c1]

TFA salt of 2-Isopropyl-5-methyl-cyclohexanecarboxylic acid [2-(2-amino-ethylamino)-4-methylsulfanyl-phenyl]amide (Compound #4)

A 100 mL round bottom flask equipped with a stir bar containing crude [2-(2-amino-5-methyl-sulfanyl-phenylamino)-ethyl]-carbamic acid tert-butyl ester was charged with THF (50 g) and DMAP (1.8 g, 0.02 mol). The reaction mixture was cooled to 0° C. and menthoyl chloride (1.5 g, 0.008 mol) was added drop wise over a 5 min period. The reaction mixture was allowed to warm to ambient temperature and stirred for an additional 30 min. The crude product was dissolved in a minimal amount of CH$_2$Cl$_2$ and purified by flash chromatography on silica gel (10% hexane/ethyl acetate for elution) which resulted in a slightly yellow solid (1.76 g, 61%). The purified material was dissolved in 20 mL of 95% TFA/H$_2$O and stirred for 1 h and concentrated. The crude product was dissolved in 30% acetonitrile/H$_2$O and purified by preparative HPLC (Ultro 120 (10 um) C18Q) using a 40-60% acetonitrile/H$_2$O (with 0.1% TFA) gradient. The pure fractions were combined, concentrated and lyophilized to give a light fluffy colorless solid (1.41 g). MS (ESI) m/z 364 (M$^+$+1)

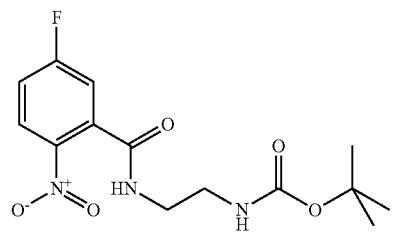 [SMILES: CC(C)(C)OC(=O)NCCNC(=O)c1cc(F)ccc1[N+](=O)[O-]]

[2-(4-Fluoro-2-nitro-benzoylamino)-ethyl]-carbamic acid tert-butyl ester

In a 100 mL round bottom flask equipped with a stir bar was charged with acetonitrile (40 mL), EDC (1.12 g, 5.9 mmol), HOBt (0.796 g, 5.9 mmol), DIEA (3.76 mL, 21.6 mmol) and Mono-N-Boc-1,2-diaminoethane (0.865 g, 5.4 mmol). The reaction mixture was stirred for ~18 h and concentrated. The residue was dissolved in a mixture of ethyl acetate (50 mL) and 1N HCl (50 mL). The heterogeneous mixture was transferred to a separatory funnel where the aqueous phase was separated and re-extracted with ethyl acetate (2×100 mL). The organic phases were combined and washed with 1N HCl (2×50 mL), H$_2$O (1×50 mL), sat NaHCO$_3$ (3×50 mL), brine (100 mL), dried over MgSO$_4$, filtered and concentrated under reduced pressure. The residue was purified by flash chromatography on silica gel (30% to 50% ethyl acetate/hexane for elution) provided the title compounds as slightly purple solid (1.12 g, 63%).

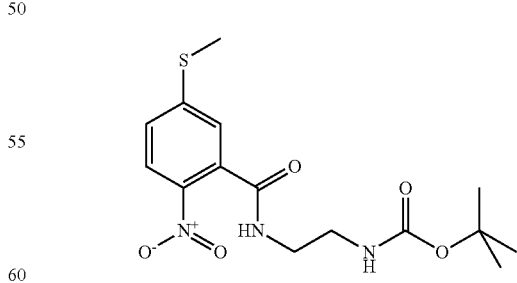

[2-(5-Methyl-sulfanyl-2-nitro-phenylamino)-ethyl]-carbamic acid tert-butyl ester In a 10 reaction vessel equipped with a stir bar was charged with DMF (5 mL), NaSMe (0.162 g, 2.3 mmol) and [2-(4- fluoro-2-nitro-benzoylamino)-ethyl]-carbamic acid tert-butyl ester (0.757 g, 2.3 mmol). The reaction mixture stirred at ambient temperature for 2 h and poured into a mixture of ethyl acetate (20 mL) and H₂O (25 mL). The heterogeneous mixture was transferred to a separatory funnel where the aqueous phase was separated and re-extracted with ethyl acetate (2×10 mL). The organic phases were combined and washed with 1N HCl (2×10 mL), H₂O (1×10 mL), sat NaHCO₃ (2×10 mL), brine (10 mL), dried over MgSO₄, filtered and concentrated under reduced pressure. The residue was purified by flash chromatography on silica gel (30% to 50% ethyl acetate/hexane for elution) provided the title compounds as slightly yellow solid (500 mg, 61%).

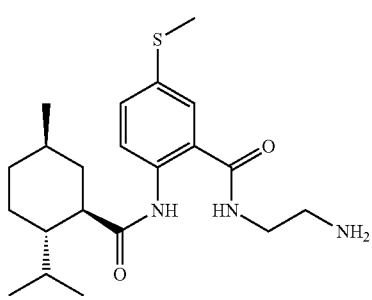 [SMILES: CSc1ccc(NC(=O)[C@@H]2C[C@H](C)CC[C@H]2C(C)C)c(C(=O)NCCN)c1]

N-(2-Amino-ethyl-2-[(2-isopropyl1-5-methyl-cyclohexanecarbonyl)-amino-4-methylsulfanyl-benzamide (Compound #2)

In a procedure similar to the synthesis of Compound #42, Compound #2 was prepared from the [2-(5-Methyl-sulfanyl-2-nitro-phenylamino)-ethyl]-carbamic acid tert-butyl ester. MS (ESI) m/z 392 (M⁺+1).

Example 6

Synthesis of Compounds of Formula I-B

This example discloses methodology for the synthesis of dihydrobenzoimidazole Trp-p8 modulators of Formula I-B.

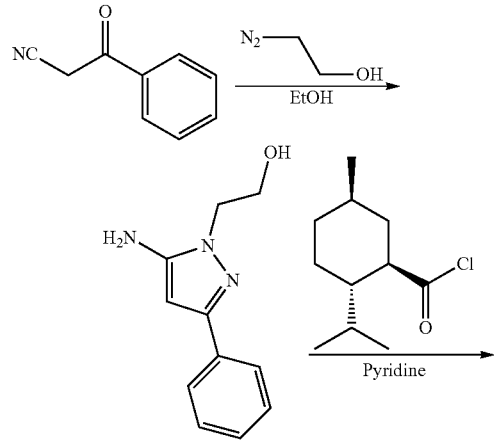

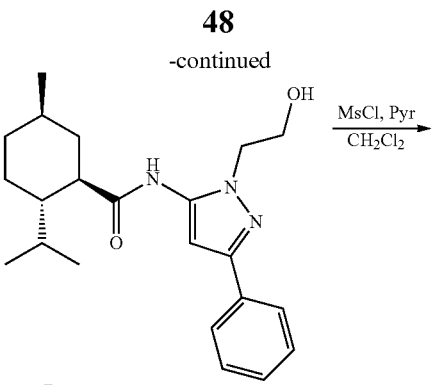

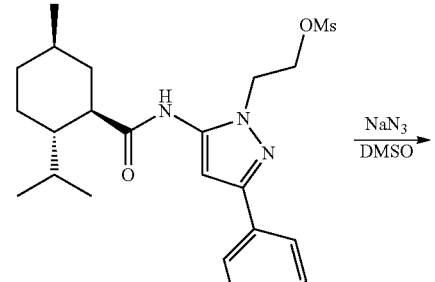

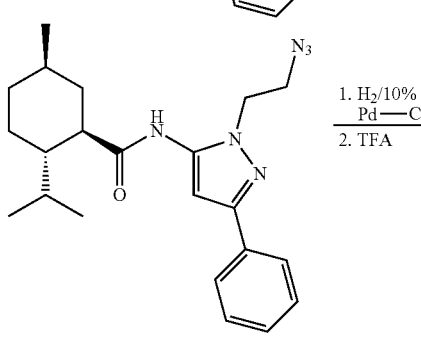

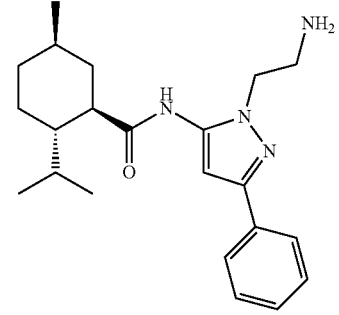

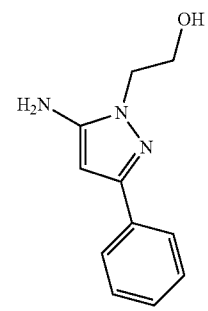

2-(5-Amino-3-phenyl-pyrazol-1-yl)-ethanol

Benzoylacetonitrile (25 g, 0.17 mol) was suspended in a mixture of 125 mL reagent grade anhydrous alcohol and 20 mL glacial acetic acid. 2-Hydroxyethylhydrazine (14.4 g, 1.1 equiv) dissolved in 35 mL alcohol was added all at once. The mixture was heated at reflux for 4 h, cooled, water was added to make 500 mL total volume and the solution was chilled in a refrigerator overnight. Crystals were filtered cold on a Buchner funnel, washed with cold water and dried on high vacuum to give the desired product (27.2 g, 79%).

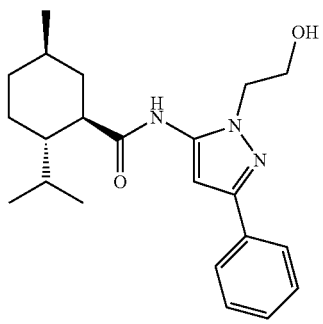 [SMILES: CC(C)[C@@H]1CC[C@@H](C)C[C@H]1C(=O)Nc1cc(-c2ccccc2)nn1CCO]

2-Isopropyl-5-methyl-cyclohexanecarboxylic acid [2-(2-hydroxy-ethyl)-5-phenyl-2H-pyrzol-3-]-amide The 2-(5-amino-3-phenyl-pyrazol-1-yl)-ethanol (87.3 g, 0.43 mol) was suspended in a mixture of dichloromethane (500 mL) and pyridine (40 mL) and chilled in an ice bath. Menthoyl chloride (100 g, 1.15 equiv) was dissolved in dichloromethane (200 mL) and added drop wise from an addition funnel protected by a $CaCl_2$ drying tube. After the 45 min required for complete addition, the ice bath was removed and stirring continued for 3 h. 1M HCl (aq, 200 mL)) was added was added and the phases were separated. The organic phases was re-extracted with 1M HCl (aq, 100 mL). 1M HCl was again added and the dichloromethane was removed under reduced pressure resulting in profuse precipitation. The precipitate was collect by vacuum filtration and the solid was washed with water several times. The solid residue was triturated with 400 mL 1:1 ether/hexanes (rapid stirring for 2 h). The solid was filtered on a Buchner funnel and washed with hexanes. After air drying overnight, further drying was effected on high vacuum for 24 h to give a colorless solid (144.4 g).

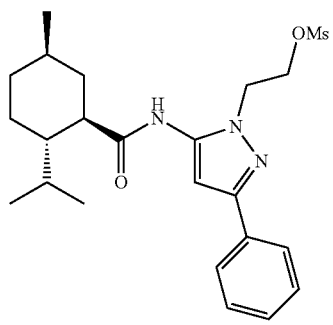 [SMILES: CC(C)[C@@H]1CC[C@@H](C)C[C@H]1C(=O)Nc1cc(-c2ccccc2)nn1CCOS(C)(=O)=O]

Methanesulfonic acid-2-{5-[2-isopropyl-5-methyl-cyclohexanecarboyl)-amino]-3-phenyl-pyrzol-1-yl}ethyl ester 2-Isopropyl-5-methyl-cyclohexanecarboxylic acid [2-(2-hydroxy-ethyl)-5-phenyl-2H-pyrzol-3-]-amide (140 g, 0.38 mol) was suspended in $CH_2Cl_2$ (500 mL) and pyridine (47 mL, 1.5 equiv) was added followed by methanesulfonyl chloride (44 mL, 1.5 equiv) at ice bath temperature. The solution was allowed to warm to room temperature and was stirred for an additional 12 h. Water (500 mL) was added and the mixture was stirred for 0.5 h. Dichloromethane was removed by evaporation leaving a precipitate of 1t. yellow granular chunks. Decantation was followed by treatment with an additional 500 mL water and decantation again. A final 500 mL quantity of water was used to transfer the solid to a Buchner funnel where it was suction dried (yield not determined).

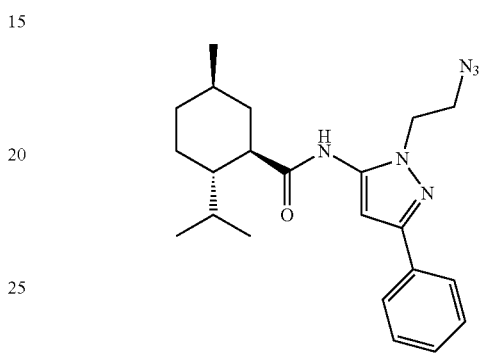

2-Isopropyl-5-methyl-cyclohexane carboxylic acid-[2-azido-ethyl)-5-phenyl-2H-pyrzol-3-yl]-amide The crude mesylate (0.38 mol) was dissolved in DMSO (500 mL) with sodium azide (37 g, 1.5 equiv). The mixture was heated to 70° C. for 6 h. Upon cooling, water (1 L) and ethyl acetate (500 mL) were added and the mixture was shaken in a reparatory funnel. The layers were separated and the organic layer was washed sequentially with 200 mL quantities of water, saturated $NaHCO_3$, and brine. The organic layer was dried with $Na_2SO_4$, decanted, and the solvent removed on the rotovap. Yield was not determined because the product was not quite free of solvent before moving to the next step.

2-Isopropyl-5-methyl-cyclohexane carboxylic acid-[2-amino-ethyl)-5-phenyl-2H-pyrzol-3-yl]-amide Crude azido compound was dissolved in 500 mL reagent grade absolute alcohol and treated with 5 g activated carbon. This was stirred for several hours and filtered through Celite. Approximately 300 mL solvent was removed on the rotovap and replaced with fresh solvent. 10% Pd—C (4.8 g, ~50%-wt. $H_2O$) was added, and a steady stream of hydrogen was maintained over the reaction mixture with rapid stirring for 24 h. Hydrogen was disconnected and conc. HCl (32 mL) was added slowly. After filtration through Celite, the filtrate was concentrated on the rotovap resulting in profuse precipitation. Still wet, diisopropyl ether was added to the residue and the suspension was stirred rapidly for 0.5 h. The solid was filtered into a Buchner funnel and washed with diethyl ether. Air dried white powder was produced.

Yield: 108.6 g (71% over three steps).

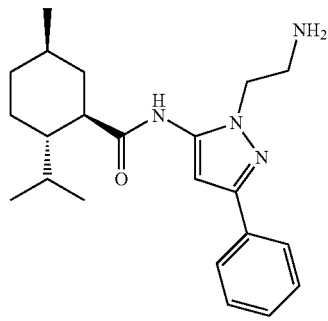 [SMILES: CC(C)[C@@H]1CC[C@@H](C)C[C@H]1C(=O)Nc1cc(-c2ccccc2)nn1CCN]

TFA salt of 2-Isopropyl-5-methyl-cyclohexane carboxylic acid-[2-amino-ethyl)-5-phenyl-2H-pyrzol-3-yl]-amide (Compound #16)

Conversion to the trifluoroacetate salt: the solid was neutralized and partitioned in a separatory funnel by shaking with 500 mL ether and 150 mL 2 N NaOH When the solid was completely dissolved, the layers were separated and the organic phase was dried with $Na_2CO_3$. Decantation and mixing with 23 mL trifluoroacetic acid was followed by evaporation of solvent and drying on high vacuum. The foam was crushed and triturated with 300 mL hexanes (rapid stirring for 3 h) which, upon filtration, produced a white powder containing much less ether. Solvent was finally removed completely by heating in a round bottom flask at 80° C. for 6 h.

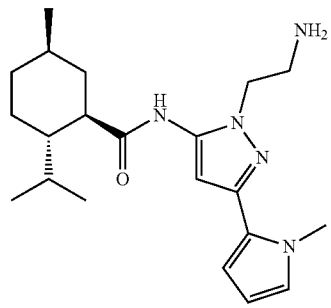

TFA salt of 2-Isopropyl-5-methyl-cyclohexane carboxylic acid-[2-(2-amino-ethyl)-5-(1-methyl-1H-pyrrol-2-yl)-2H-pyrazol-3-yl]-amide (Compound #17)

In a procedure similar to the synthesis of Compound #16, Compound #17 was prepared from 1-methyl-1H-pyrrole-2-carbaldehyde and 2-hydroxyethylhydrazine. This material was purified by preparative HPLC (Ultro 120 (10 um) C18Q) using a 40-60% acetonitrile/$H_2O$ (with 0.1% TFA) gradient. MS (ESI) m/z 372 ($M^+$+1).

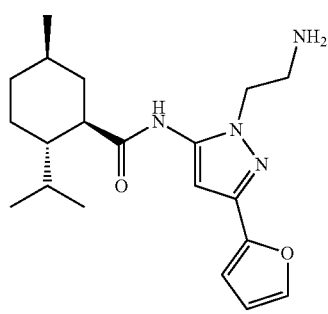 [SMILES: CC(C)[C@@H]1CC[C@@H](C)C[C@H]1C(=O)Nc1cc(-c2ccco2)nn1CCN]

TFA salt of 2-Isopropyl-5-methyl-cyclohexane carboxylic acid-[2-(2-amino-ethyl)-5-furan-2-yl-2H-pyrzol-3-yl]-amide (Compound #14)

In a procedure similar to the synthesis of Compound #16, Compound #14 was prepared from 2-furoylacetonitrile and 2-hydroxyethylhydrazine. This material was purified by preparative HPLC (Ultro 120 (10 um) C18Q) using a 40-60% acetonitrile/$H_2O$ (with 0.1% TFA) gradient. MS (ESI) m/z 344 ($M^+$+1).

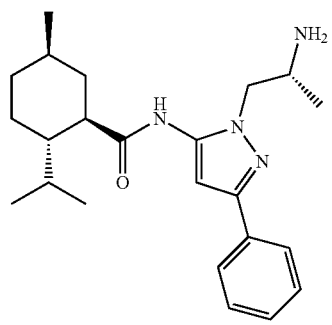

TFA salt of 2-Isopropyl-5-methyl-cyclohexane carboxylic acid-[2-(2-amino-ethyl)-5-(1-methyl-1H-pyrrol-2-yl)-2H-pyrazol-3-yl]-amide (Compound #15)

In a procedure similar to the synthesis of Compound #16, Compound #15 was prepared from 2-benzoylacetonitrile and (2-diazenyl-ethyl)-carbamic acid tert-butyl ester. This material was purified by preparative HPLC (Ultro 120 (10 um) C18Q) using a 40-60% acetonitrile/$H_2O$ (with 0.1% TFA) gradient. MS (ESI) m/z 383 ($M^+$+1).

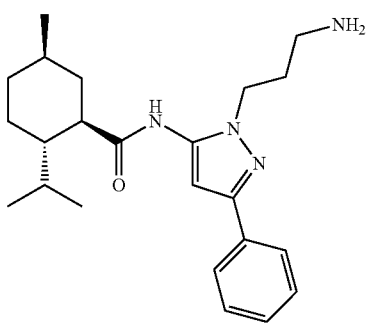 [SMILES: CC(C)[C@@H]1CC[C@@H](C)C[C@H]1C(=O)Nc1cc(-c2ccccc2)nn1CCCN]

TFA salt of 2-Isopropyl-5-methyl-cyclohexane carboxylic acid-[2-(2-amino-ethyl)-5-(1-methyl-1H-pyrrol-2-yl)-2H-pyrazol-3-yl]-amide (Compound #18)

In a procedure similar to the synthesis of Compound #16, Compound #18 was prepared from 2-benzoylacetonitrile and (3-diazenyl-propyl)-carbamic acid tert-butyl ester. This material was purified by preparative HPLC (Ultro 120 (10 um) C18Q) using a 40-60% acetonitrile/H$_2$O (with 0.1% TFA) gradient. MS (ESI) m/z 383 (M$^+$+1).

Example 7

Synthesis of Compounds of Formula I-C

This example discloses methodology for the synthesis of dihydrobenzoimidazole Trp-n8 modulators of Formula I-C

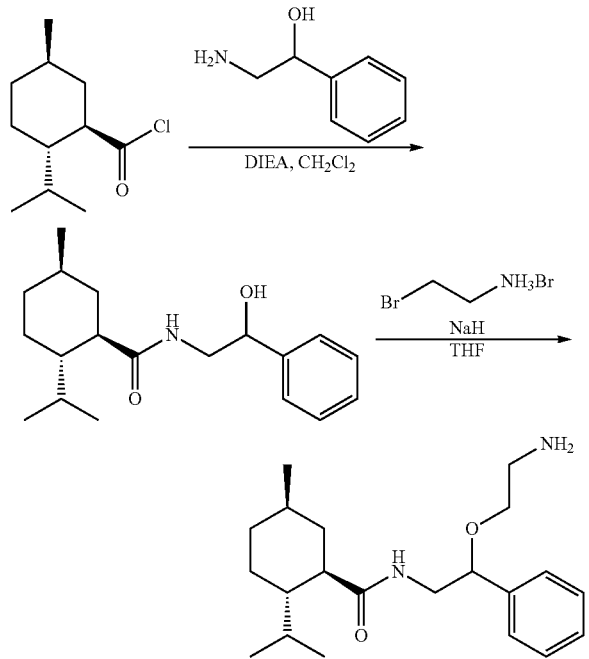

Scheme 6.

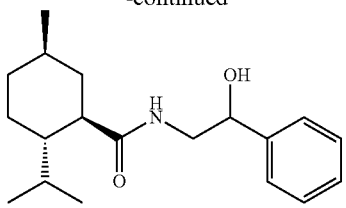

2-Isopropyl-5-methyl-cyclohexanecarboxylic acid (2-hydroxy-2-phenyl-ethyl)-amide A 500 mL round bottom flask equipped with stir bar was charged with CH$_2$Cl$_2$ (200 mL), DIEA (28 g, 0.219 mol), and 2-Amino-1-phenyl-ethanol (10 g, 0.073 mol) and cooled to 0° C. Menthoyl chloride (14.8 g, 0.073 mol) was added drop wise over a 15 min period. Once the addition was complete the reaction was allowed to warm to ambient temperature and stirred 2 h. CH$_2$Cl$_2$ (100 mL) and 1N HCl (100 mL) was added to the reaction mixture and stirred for an additional 20 min. The heterogeneous mixture was transferred to a separatory funnel where the aqueous phase was separated and re-extracted with CH$_2$Cl$_2$ (2×100 mL). The organic phases were combined and washed with 1N HCl (8×100 mL), H$_2$O (1×100 mL), 1N NaOH (2×100 mL), brine (100 mL), dried over MgSO$_4$, filtered and concentrated under reduced pressure. The residue was eluted through a plug of silica gel (50% ethyl acetate/hexane for elution) provided the title compounds as colorless solid (18.8 g, 85%).

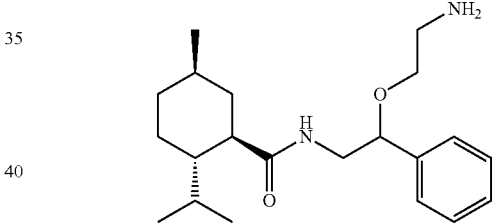

TFA salt of 2-Isopropyl-5-methyl-cyclohexanecarboxylic [2-(2-amino-4-ethoxy)-2-phenyl-ethyl]-amide (Compound #30)

A 500 mL round bottom flask equipped with stir bar was charged with anhydrous THF (200 mL) and 2-isopropyl-5-methyl-cyclohexanecarboxylic acid (2-hydroxy-2-phenyl-ethyl)-amide (10 g, 0.03 mol). NaH (0.87 g, 0.04 mol) was added in one portion and stirred for 10 min (until H$_2$ stopped being produced). 1-Bromoethyl-2-amine hydrogen bromide (6.74 g, 0.033 mol) and NaH (0.87 g, 0.036 mol) were added to the reaction mixture and stirred for 2 h. An additional equivalent of NaH (0.87 g, 0.036 mol) was added and stirred an additional 2 h. The excess NaH was quenched by pouring the reaction mixture onto ice. Ethyl acetate (200 mL) and H$_2$O were added and stirred for 20 min. The heterogeneous mixture was transferred to a separatory funnel where the aqueous phase was separated and re-extracted with ethyl acetate (2×100 mL). The organic phases were combined and washed with H$_2$O (1×100 mL), brine (100 mL), dried over MgSO$_4$, filtered and concentrated under reduced pressure. The crude product was dissolved in 30% acetonitrile/H$_2$O and purified by preparative HPLC (Ultro 120 (10 um) C18Q)

using a 30-60% acetonitrile/H₂O (with 0.1% TFA) gradient. The pure fractions were combined, concentrated and lyophilized to give a light fluffy colorless solid (9.4 g, 62%). MS (ESI) m/z 347 (M$^+$+1).

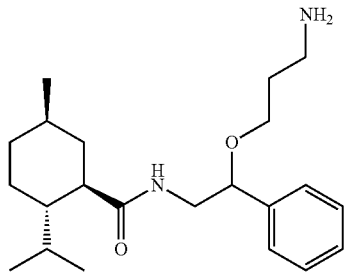 [SMILES: CC(C)[C@@H]1CC[C@@H](C)C[C@H]1C(=O)NCC(OCCCN)c1ccccc1]

TFA salt of 2-Isopropyl-5-methyl-cyclohexanecarboxylic [2-(3-amino-4-propoxy)-2-phenyl-ethyl]-amide (Compound #31)

In a procedure similar to the synthesis of Compound #30, Compound #31 was prepared from 2-isopropyl-5-methyl-cyclohexanecarboxylic acid (2-hydroxy-2-phenyl-ethyl)-amide and 1-Bromopropyl-3-amine hydrogen bromide. This material was purified by preparative HPLC (Ultro 120 (10 um) C18Q) using a 40-60% acetonitrile/H₂O (with 0.1% TFA) gradient. MS (ESI) m/z 361 (M$^+$+1).

Example 8

Synthesis of Additional Dihydrobenzoimidazole Compounds of Formula I-D

This example discloses methodology for the synthesis of dihydrobenzoimidazole Trp-p8 modulators of Formula I-D Scheme 7.

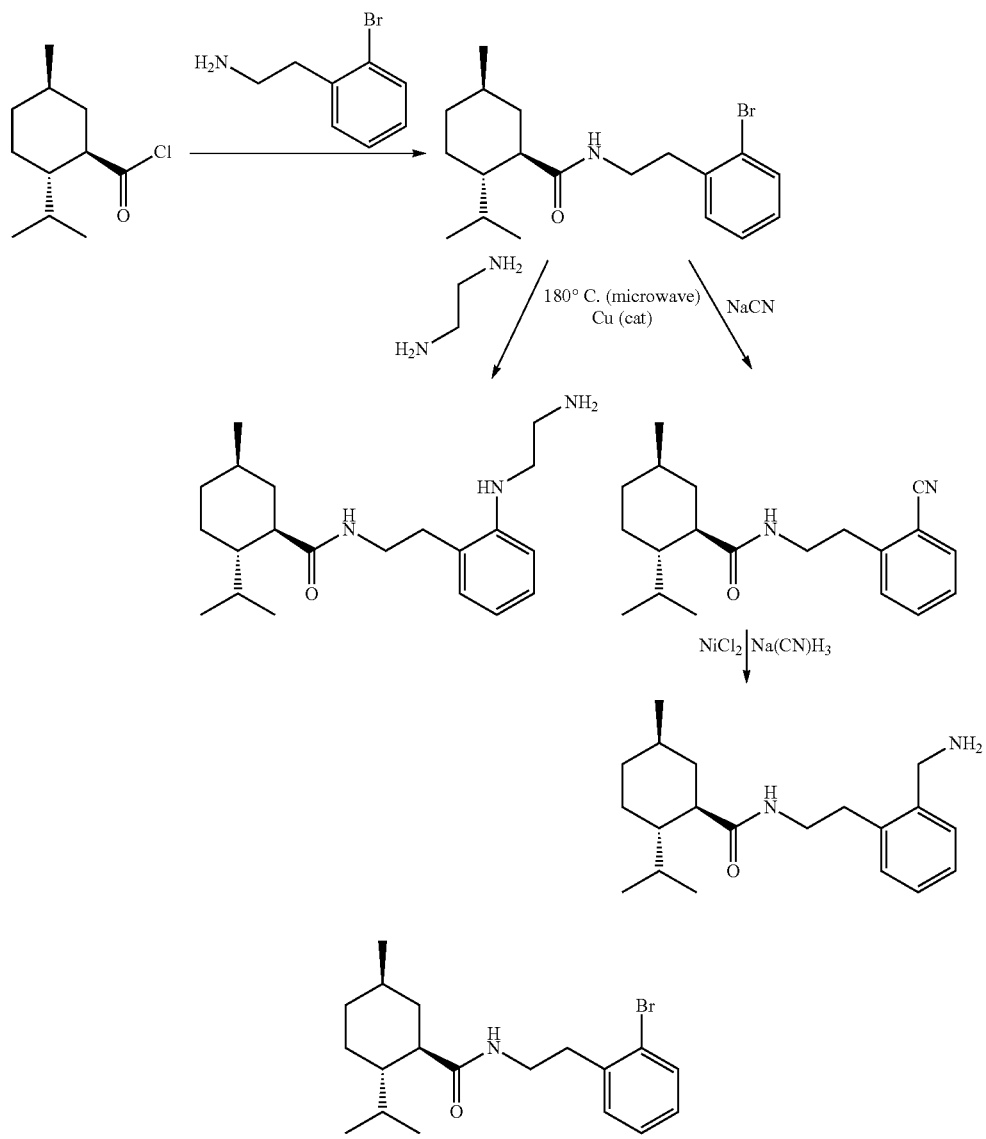

2-Isopropyl-5-methyl-cyclohexanecarboylic acid [2-(2-bromo-phenyl)-ethyl]-amide A 100 mL round bottom flask equipped with a stir bar was charged with CH$_2$Cl$_2$ (30 mL), 2-bromo-phenethylamine (1.0 g, 5.00 mmol) and triethylamine (684 µl, 5.05 mmol). The reaction solution was treated with menthoyl chloride (1.02 g, 5.05 mmol) in one portion and stirred at ambient temperature for 30 minutes. The reaction was diluted with CH$_2$Cl$_2$ (50 mL) and washed with water (3×100 mL). Organic layer was dried over anhydrous sodium sulfate and concentrated under reduced pressure to give a thick oil (1.8 g). Product was used for next step without purification.

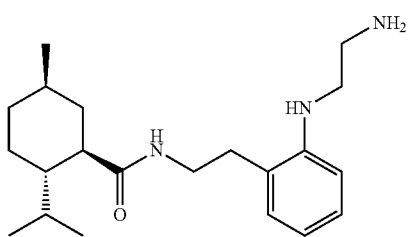 [SMILES: CC(C)[C@@H]1CC[C@@H](C)C[C@H]1C(=O)NCCc1ccccc1NCCN]

TFA salt of 2-Isopropyl-5-methyl-cyclohexanecarboylic acid {2-[2-(2-amino-ethylamino)-phenyl]-ethyl}-amide (Compound #33)

A 25 mL microwave reaction vessel equipped with a stir bar was charged with neat diaminoethane (10 mL), 2-isopropyl-5-methyl-cyclohexanecarboylic acid [2-(2-bromo-phenyl)-ethyl]-amide (1.5 g, 4.1 mmol) and Cu powder (390 mg, 6.147 mmol, 1.5 eq.). The reaction vessel was subjected to microwave at 180° C. for 40 minutes. The reaction mixture was transferred to a round bottom flask and concentrated. The residue was dissolved in DMSO (1 mL) and purified by preparative HPLC (Ultro 120 (10 um) C18Q) using a 10-40% acetonitrile/H$_2$O (with 0.1% TFA) gradient. The pure fractions were combined, concentrated and lyophilized to give a colorless solid (1 g, 52%) (MS (ESI) m/z 346 (M$^+$+1).

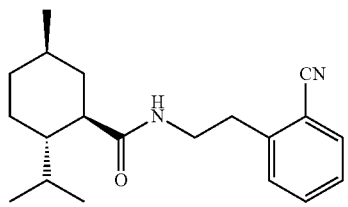 [SMILES: CC(C)[C@@H]1CC[C@@H](C)C[C@H]1C(=O)NCCc1ccccc1C#N]

2-Isopropyl-5-methyl-cyclohexanecarboxylic acid [2-(2-cyano-phenyl)-ethyl]-amide A 20 mL microwave reaction vessel equipped with a stir bar was charged with 2-isopropyl-5-methyl-cyclohexanecarboylic acid [2-(2-bromo-phenyl)-ethyl]-amide (1.54 g, 4.2 mmol), CuCN (0.60 g, 6.4 mmol) and NMP (10 mL). The reaction vessel was subjected to microwave at 180° C. for 40 minutes. The reaction mixture was transferred to a round bottom flask and concentrated. The residue to purified by flash chromatography on silica gel (10% ethyl acetate/hexane for elution) to give a colorless solid (1.25 g, 81%).

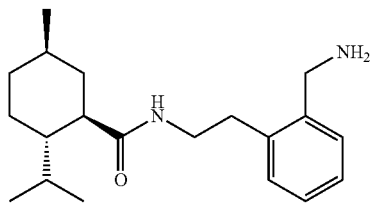 [SMILES: CC(C)[C@@H]1CC[C@@H](C)C[C@H]1C(=O)NCCc1ccccc1CN]

2-Isopropyl-5-methyl-cyclohexanecarboxylic acid [2-2-aminomethyl-phenyl)-ethyl]-amide (Compound #34)

A 100 mL round bottom flask equipped with a stir bar was charged with 2-isopropyl-5-methyl-cyclohexanecarboxylic acid [2-(2-cyano-phenyl)-ethyl]-amide (1.25 g, 4.0 mmol) and methanol (50 mL). NiCl$_2$ (1.14 g, 8.8 mmoles) and NaBH$_4$ (0.64 g, 16.8 mmol). NaBH$_4$ was added in small portion over a 30 min. period and stirred for 1 h. NaBH$_4$ (0.20 g) was added and reaction mixture and stirred an additional 20 minutes. The reaction mixture was passed through a cake of celite and concentrated under reduced pressure. The black residue was dissolved in a minimal amount of acetonitrile and passed through a C18 silica gel cartridge and purified by preparative HPLC (Ultro 120 (10 um) C18Q) using a 10-40% acetonitrile/H$_2$O (with 0.1% TFA) gradient. The pure fractions were combined, concentrated and lyophilized to give a colorless solid (1.1 g). MS (ESI) m/z 317 (M$^+$+1).

Example 9

Synthesis of Additional Compounds of Formula I-C

This example discloses methodology for the synthesis of Trp-p8 modulators of Formula I-C Scheme 7.

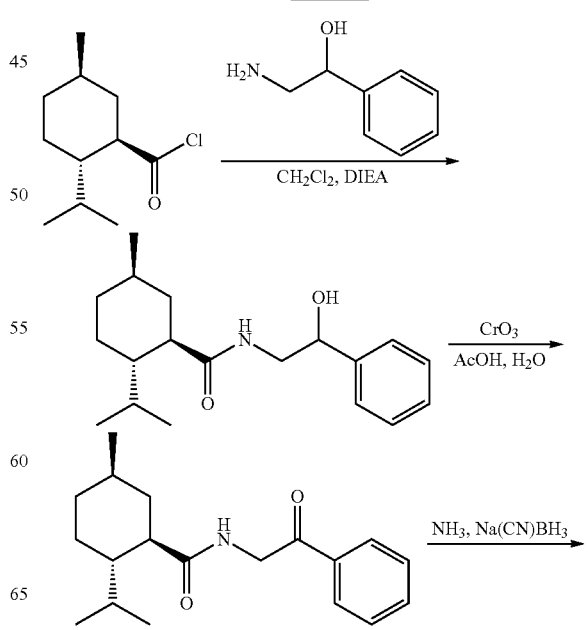

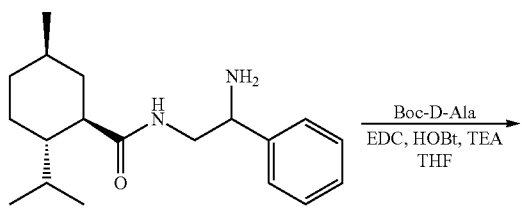

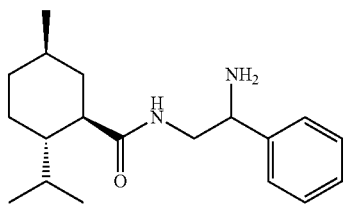

2-Isopropyl-5-methyl-cyclohexanecarboxylic acid (2-amino-2-phenyl-ethyl)-amide A 25 mL microwave reaction vessel equipped with a stir bar was charged with 2-isopropyl-5-methyl-cyclohexanecarboxylic acid (2-oxo-2-phenyl-ethyl)-amide (80 mg) and ammonia (1.5 mL, 7 M in methanol). A drop of acetic acid and NaCNBH$_3$ (20 mg) were added to the reaction mixture and subjected to microwave at 80° C. for 80 min. The residue was taken up in ethyl acetate (30 mL) and saturated NaHCO$_3$ (aq.) (30 mL). The heterogeneous mixture was transferred to a reparatory funnel where the aqueous phase was separated and re-extracted with ethyl acetate (2×10 mL). The organic phases were combined and washed with sat NaHCO$_3$ (3×10 mL), H$_2$O (10 mL), brine (10 mL), dried over Na$_2$SO$_4$, filtered and concentrated under reduced pressure to give a solid (75 mg).

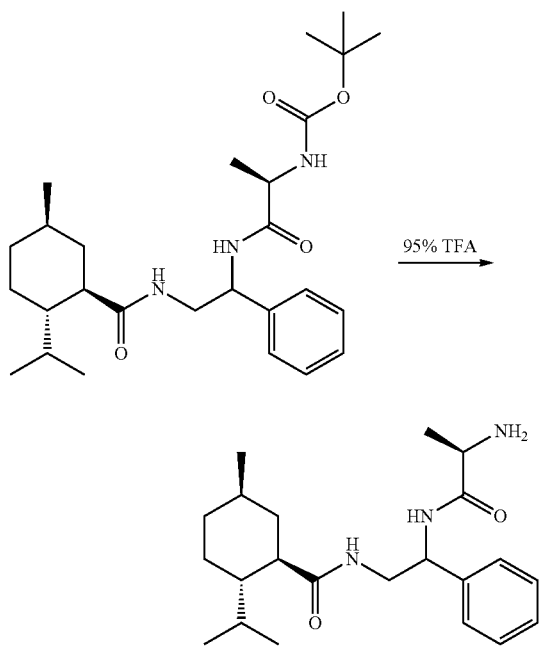

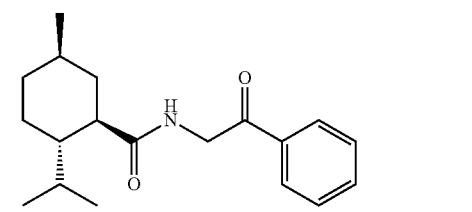 [SMILES: CC(C)[C@@H]1CC[C@@H](C)C[C@H]1C(=O)NCC(=O)c1ccccc1]

2-Isopropyl-5-methyl-cyclohexanecarboxylic acid (2-oxo-2-phenyl-ethyl)-amide A 20 mL round bottom flask equipped with a stir bar was charge with 2-Isopropyl-5-methyl-cyclohexanecarboxylic acid (2-hydroxy-2-phenyl-ethyl)-amide (100 mg, 0.33 mmol) and acetic acid (1 mL). A solution of CrO$_3$ (36 mg, 0.363 mmoles, 1.1 eq) in acetic acid (500 µl) and water (100 µl) was slowly added to the reaction mixture. The reaction mixture was stirred at ambient temperature for 15 min and diluted with ethyl acetate (30 mL) and saturated NaHCO$_3$ (aq.) (30 mL). The heterogeneous mixture was transferred to a reparatory funnel where the aqueous phase was separated and re-extracted with ethyl acetate (2×10 mL). The organic phases were combined and washed with sat NaHCO$_3$ (3×10 mL), H$_2$O (10 mL), brine (10 mL), dried over Na$_2$SO$_4$, filtered and concentrated under reduced pressure. The residue was purified by flash chromatography on silica gel (30% to 50% ethyl acetate/hexane for elution) provided the title compounds as white solid (92 mg, 93%).

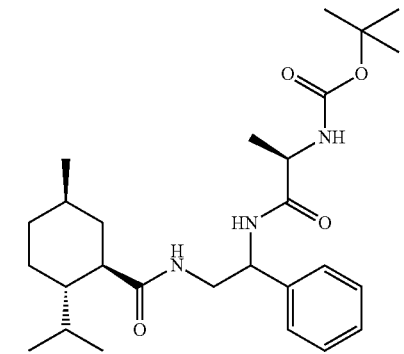 [SMILES: CC(C)[C@@H]1CC[C@@H](C)C[C@H]1C(=O)NCC(NC(=O)[C@@H](C)NC(=O)OC(C)(C)C)c1ccccc1]

(1-{2-[(2-Isopropyl-5-methyl-cyclohexanecarbonyl)-amino]-1-phenyl-ethylcarbamoyl}-ethyl)-carbamic acid tert-butyl ester A 15 mL reaction vessel equipped with a stir bar was charged with THF (15 mL), Boc-(R)-alanine (52 mg, 0.273 mmoles), HOBt (37.87 mg, 0.273 mmoles), EDCI (53 mg, 0.273 mmoles) and TEA (37 µl, 0.273 mmoles). The reaction mixture was stirred for 15 min. whereupon 2-isopropyl-5-methyl-cyclohexanecarboxylic acid (2-amino-2-phenyl-ethyl)-amide (75 mg, 0.248 mmol) was added and stirred for an additional 3 h. Ethyl acetate (10 mL) and H$_2$O (10 mL) were added to the reaction mixture. The heterogeneous mixture was transferred to a separatory funnel where the aqueous phase was separated and re-extracted with ethyl acetate (2×10 mL). The organic phases were combined and washed with 1N HCl (2×10 mL), H$_2$O (1×10 mL), sat NaHCO$_3$ (3×10 mL), brine (10 mL), dried over MgSO$_4$, filtered and concentrated under reduced pressure. The residue was purified by flash chromatography on silica gel (20% ethyl acetate/hexane for elution) provided the title compounds as colorless solid (30 mg).

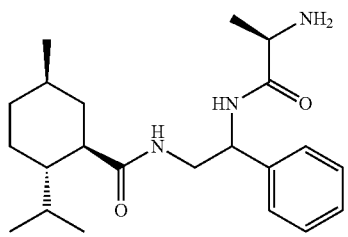 [SMILES: CC(C)[C@@H]1CC[C@@H](C)C[C@H]1C(=O)NCC(NC(=O)[C@@H](C)N)c1ccccc1]

TFA salt of 2-Isopropyl-5-methyl-cyclohexancarboxylic acid [2-(2-amino-propionylamino)-2-phenyl-ethyl]-amide (Compound #28)

A 5 mL round bottom flask equipped with a stir bar was charged with 10% TFA/CH$_2$Cl$_2$ and (1-{2-[(2-isopropyl-5-methyl-cyclohexanecarbonyl)-amino]-1-phenyl-ethylcarbamoyl}-ethyl)-carbamic acid tert-butyl ester (30 mg) and stirred for 1 h. The TFA was removed under reduced pressure and the residue was dissolved in 30% acetonitrile/H$_2$O (with 0.1% TFA) and purified by preparative HPLC (Ultro 120 (10 um) C18Q) using a 10-40% acetonitrile/H$_2$O (with 0.1% TFA) gradient. The pure fractions were combined, concentrated and lyophilized to give a colorless solid (17.7 mg) (MS (ESI) m/z 374 (M$^+$+1).

Example 10

Expression of Trp-p8 in CHO Cells

Human Trp-p8 transfected CHO cells (referred to herein as CHO/Trp-p8) were generated for use in experiments of the present invention. Expression of Trp-p8 polypeptide in this transfectant and the absence of any endogenous expression in the non-transfected CHO was confirmed by western blot and immunofluorescence using a Trp-p8 specific antibody (GS2.20) as well as the calcium flux assay with Icilin (1-[2-hydroxyphenyl]-4-[3-nitrophenyl]-1,2,3,6-tetrahydropyrimidine-2-one) and menthol (2-isopropyl-5-methyl-cyclohexanol). Non-transfected CHO cells were used to establish the specificity of the effects of the compounds observed with CHO/Trp-p8.

Example 11

Trp-p8-mediated Decrease in Cell Viability following Exposure of CHO/Trp-p8 Cells with Candidate Trp-p8 Agonist Compounds at 37° C.

This Example discloses an ATP viability assay suitable for screening for effective Trp-p8 agonists. The ATP viability assay described herein employs CHO cells expressing an exogenous Trp-p8 cDNA. This example further establishes that Trp-p8 agonists of the present invention are effective in decreasing the viability of Trp-p8 expressing cells.

The concentration of intracellular ATP declines very rapidly when metabolically active cells undergo necrosis and/or apoptosis. The ATP concentration and consequently the relative cell viability can be measured by established methods using commercially available reagents. In the agonist screening methodology disclosed herein, a compound that specifically decreases the viability of CHO/Trp-p8 cells is referred to as an agonist.

As a primary screen for efficacy and specificity for agonists, both the non-transfected CHO and CHO/Trp-p8 cells were exposed to 1 or 10 μM of test compounds in 1% dimethylsulfoxide (DMSO) or 1% DMSO (control) in a 96-well black walled, black-bottomed, cell-culture treated plate. DMSO was the solvent for all of the compounds tested. After 24-26 hours at 37° C., the cells were lysed and ATP concentration determined via a chemiluminescence assay using a commercially available reagent kit—Cell Titer-Glo (Promega; Madison, Wis.). Relative viability (%), expressed as the ATP level in cells treated with compounds expressed as a percentage of ATP levels in cells treated with the DMSO alone, was a measure of the agonist activity of the candidate compound—the lower the % viability, the more potent the Trp-p8 agonist. EC$_{50}$ values were determined for the most active candidate Trp-p8 agonists at 37° C. by measuring viability at 8-10 agonist concentrations. (EC$_{50}$ is defined herein as the agonist concentration at which there is a 50% reduction in relative cell viability).

Exemplary Trp-p8 Agonists of Formula I, Formula I-A, Formula I-B, Formula I-C, Formula I-D, and Formula I-E, that were efficacious in the ATP viability assay are presented herein in Tables 1-5. EC50 data is designated as follows: A=<0.020 uM; B=0.021-0.050 uM; C=0.051-0.10 uM.

In Tables 1-5, the structures provided are of the form:

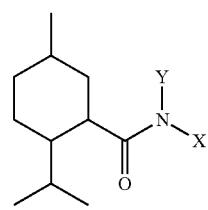

Wherein chemical names are provided for X and/or Y. Where names are provided for "X/Y", the names are inclusive of the nitrogen group.

Figure 1A:
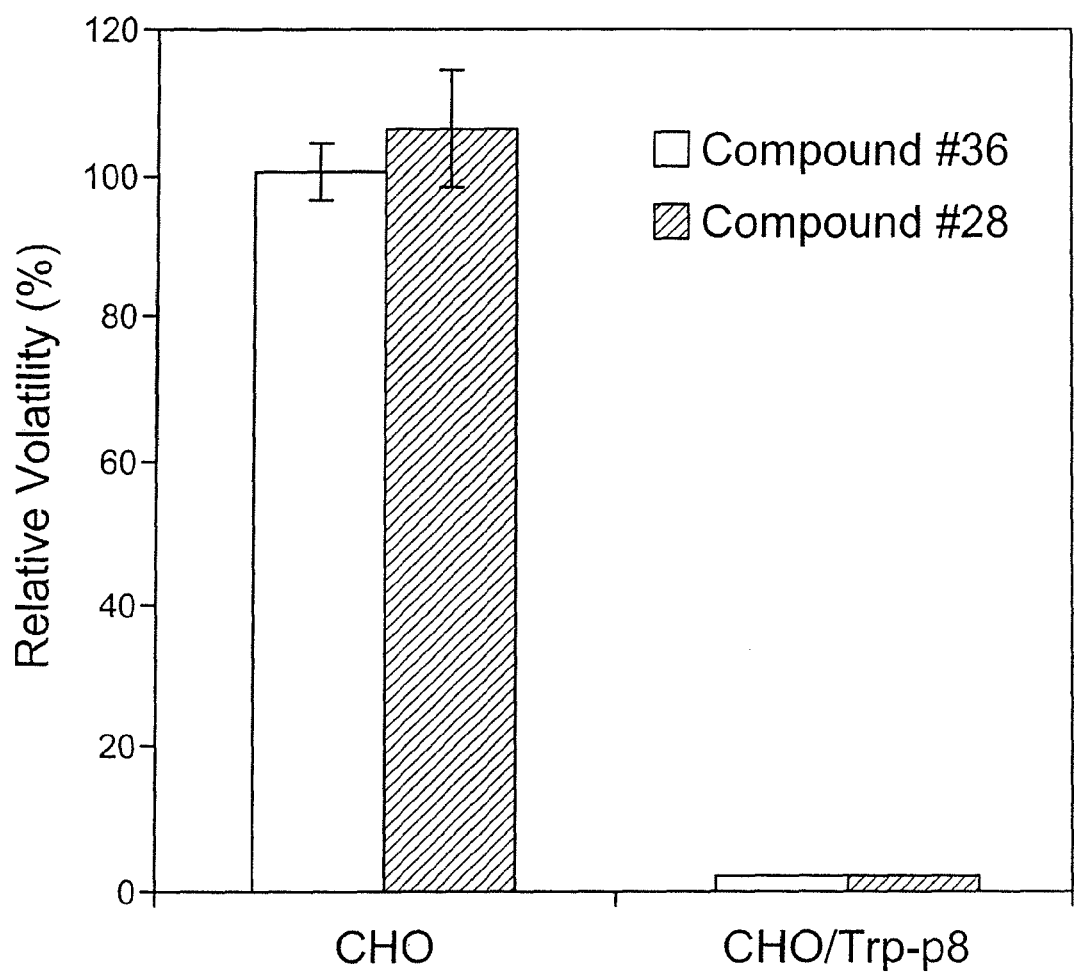

Viability of CHO/Trp-p8 cells following treatment with exemplary Trp-p8 agonists is presented in FIG. 1.

TABLE 1
Exemplary Compounds of Formula I-A
| Compound # | Structure | EC50 | X |
|---|---|---|---|
| 1 | 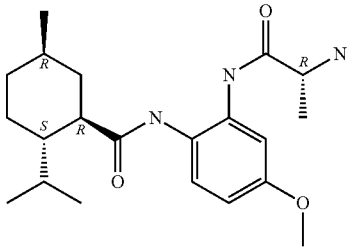 | A | 2-(2-amino-propionylamino)-4-methoxy-phenyl |
| 2 | 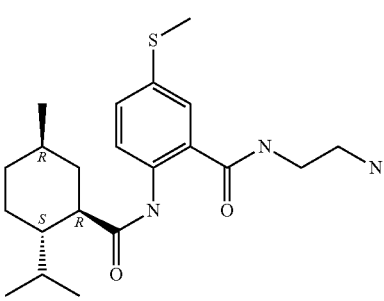 | A | N-(2-Amino-ethyl)-2-amino-5-methylsulfanyl-phenyl |
| 3 | 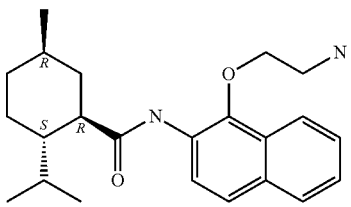 | A | 1-(2-amino-ethoxy)-naphthalen-2-yl |
| 4 | 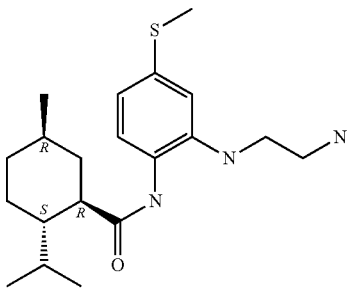 | A | 2-(2-amino-ethylamino)-4-methylsulfanyl-phenyl |
| 5 | 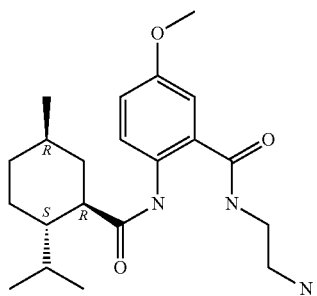 | A | N-(2-Amino-ethyl)-5-methoxy-benzamide |

TABLE 1-continued

Exemplary Compounds of Formula I-A

| Compound # | Structure | EC50 | X |
|---|---|---|---|
| 6 | 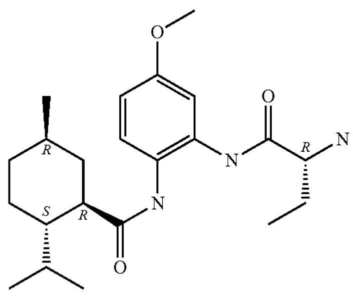 | B | 2-(2-amino-butyrylamino)-4-methoxy-phenyl |
| 7 | 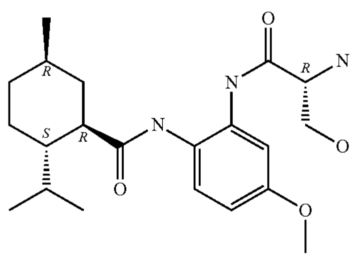 | B | 2-(2-amino-3-hydroxy-propionylamino)-4-methoxy-phenyl |
| 8 | 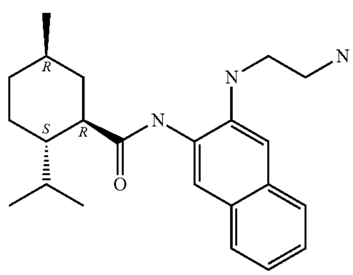 | B | 3-(2-amino-ethylamino)-naphthalen-2-yl |
| 9 | 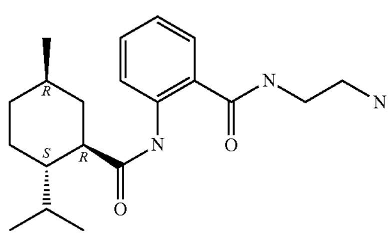 | B | N-(2-Amino-ethyl)-2-amino-benzamide |
| 10 | 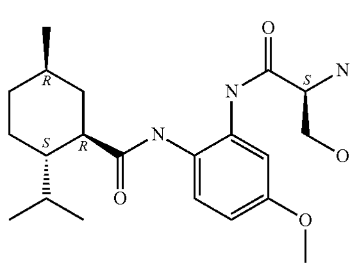 | B | 2-(2-amino-3-hydroxy-propionylamino)-4-methoxy-phenyl |

TABLE 1-continued

Exemplary Compounds of Formula I-A

| Compound # | Structure | EC50 | X |
|---|---|---|---|
| 11 | 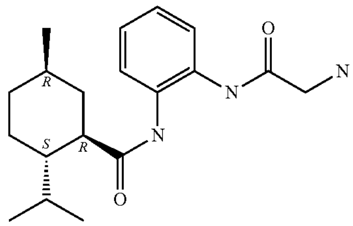 | C | 2-(2-amino-acetylamino)-phenyl |
| 12 | 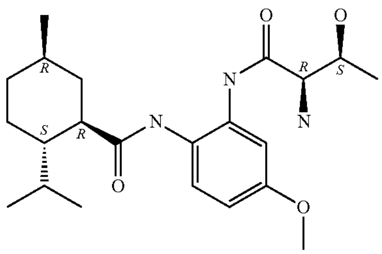 | C | 2-(2-amino-3-hydroxy-butyrylamino)-4-methoxy-phenylamide |
| 13 | 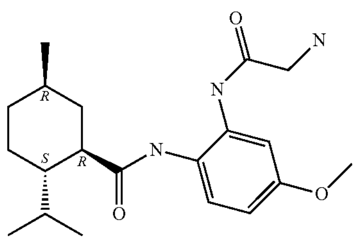 | C | 2-(2-amino-acetylamino)-4-methoxy-phenyl |

TABLE 2

Exemplary Compounds of Formula I-B

| Object ID | Structure | EC50 | X |
|---|---|---|---|
| 14 | 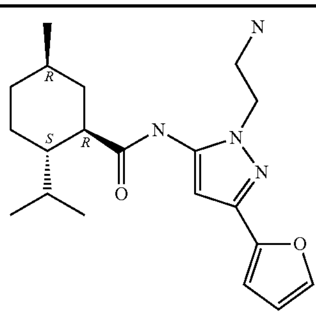 | A | 2-(2-amino-ethyl)-5-furan-2-yl-2H-pyrazol-3-yl |
| 15 | 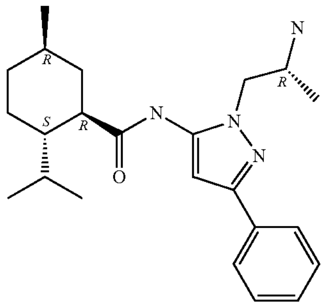 | A | 2-(2-amino-propyl)-5-phenyl-2H-pyrazol-3-yl |

TABLE 2-continued

Exemplary Compounds of Formula I-B

| Object ID | Structure | EC50 | X |
|---|---|---|---|
| 16 | 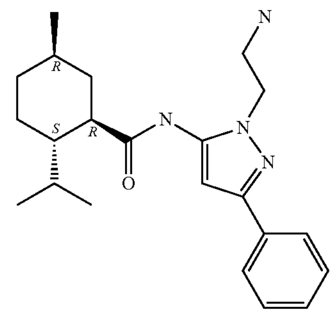 | A | 2-(2-amino-ethyl)-5-phenyl-2H-pyrazol-3-yl |
| 17 | 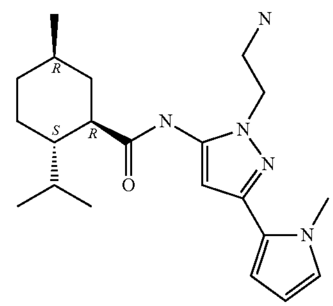 | A | 2-(2-amino-ethyl)-5-(1-methyl-1H-pyrrol-2-yl)-2H-pyrazol-3-yl |
| 18 | 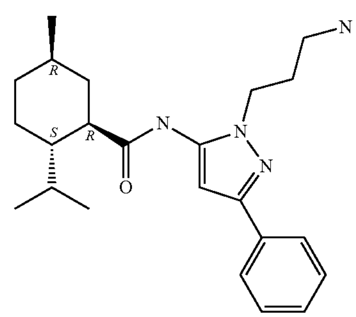 | A | 2-(2-amino-propyl)-5-phenyl-2H-pyrazol-3-yl |
| 19 | 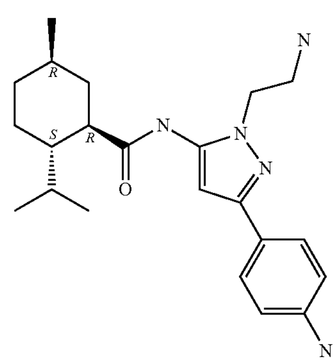 | B | 2-(2-amino-ethyl)-5-(4-amino-phenyl)-2H-pyrazol-3-yl |

TABLE 2-continued

Exemplary Compounds of Formula I-B

| Object ID | Structure | EC50 | X |
|---|---|---|---|
| 20 | 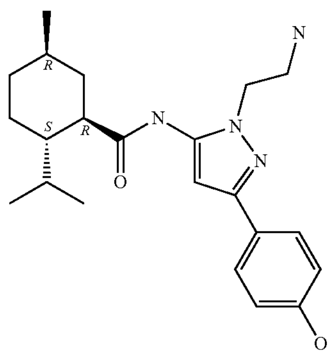 | B | 2-(2-amino-ethyl)-5-(4-hydroxy-phenyl)-2H-pyrazol-3-yl |
| 21 | 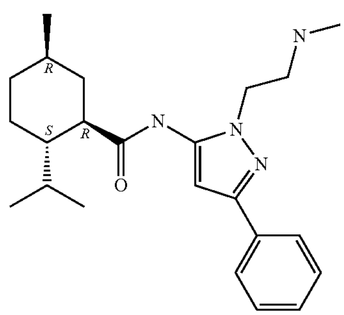 | B | 2-(2-methylamino-ethyl)-5-phenyl-2H-pyrazol-3-yl |
| 22 | 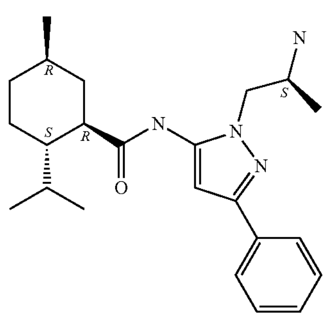 | B | 2-(2-amino-propyl)-5-phenyl-2H-pyrazol-3-yl |
| 23 | 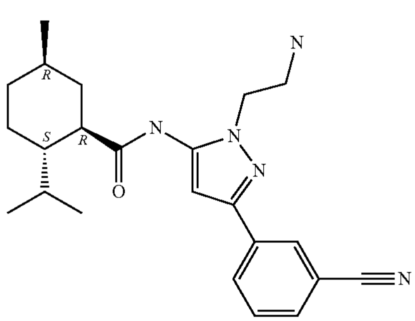 | B | 2-(2-amino-ethyl)-5-(3-cyano-phenyl)-2H-pyrazol-3-yl |

TABLE 2-continued

Exemplary Compounds of Formula I-B

| Object ID | Structure | EC50 | X |
|---|---|---|---|
| 24 | 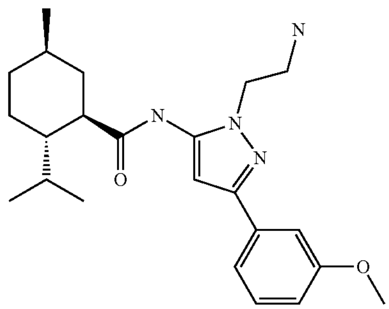 [SMILES: COc1cccc(-c2cc(NC(=O)[C@@H]3C[C@H](C)CC[C@H]3C(C)C)n(CCN)n2)c1] | B | 2-(2-amino-ethyl)-5-(3-methoxy-phenyl)-2H-pyrazol-3-yl |
| 25 | 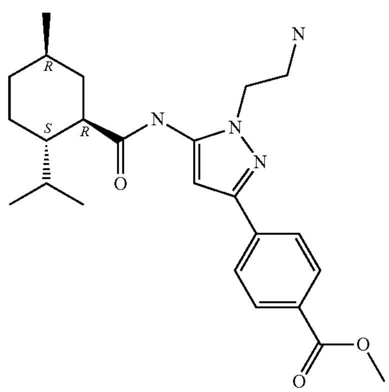 | C | 4-{1-(2-Amino-ethyl)-1H-pyrazol-3-yl}-benzoic acid methyl ester |
| 26 | 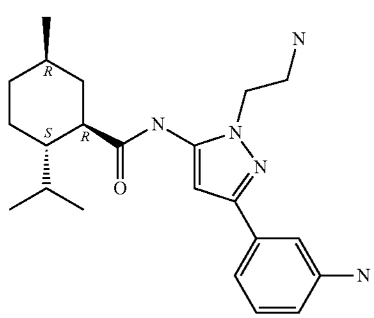 | C | 2-(2-amino-ethyl)-5-(3-amino-phenyl)-2H-pyrazol-3-yl |
| 27 | 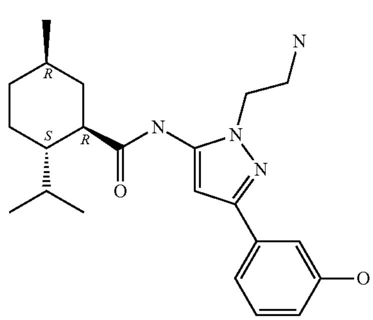 | C | 2-(2-amino-ethyl)-5-(3-hydroxy-phenyl)-2H-pyrazol-3-yl |

TABLE 3

Exemplary Compounds of Formula I-C

| Compound # | Structure | EC50 | X |
|---|---|---|---|
| 28 | 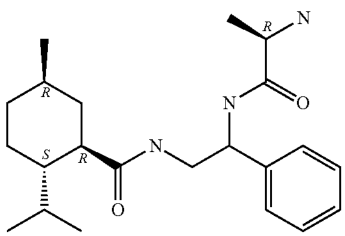 | A | 2-(2-amino-propionylamino)-2-phenyl-ethyl |
| 29 | 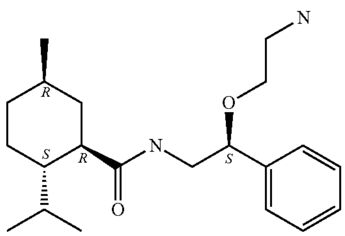 | A | 2-(2-amino-ethoxy)-2-phenyl-ethyl |
| 30 | 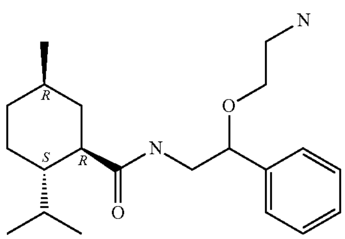 | A | 2-(2-amino-ethoxy)-2-phenyl-ethyl |
| 31 | 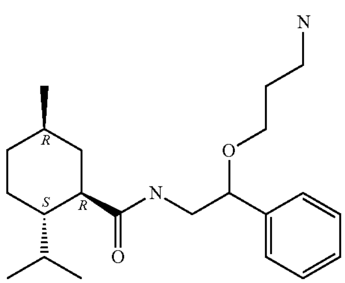 | B | 2-(3-amino-propoxy)-2-phenyl-ethyl |
| 32 | 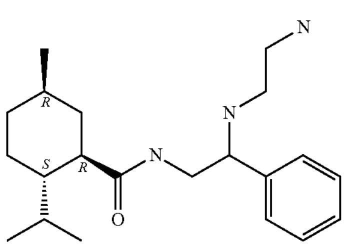 | C | 2-(2-amino-ethylamino)-2-phenyl-ethyl |

TABLE 4

Exemplary Compounds of Formula I-D

| Compound # | Structure | EC50 | X |
|---|---|---|---|
| 33 | 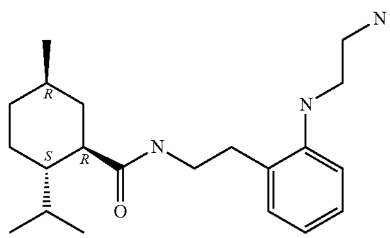 | A | 2-[2-(2-amino-ethylamino)-phenyl]-ethyl |
| 34 | 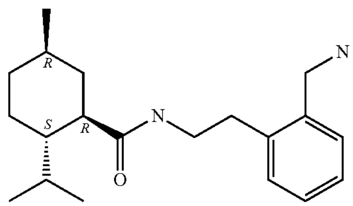 | A | 2-(2-aminomethyl-phenyl)-ethyl |
| 35 | 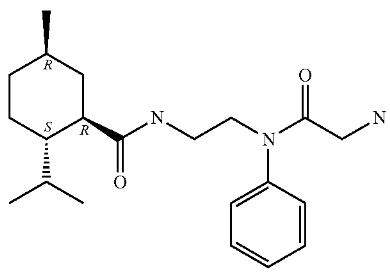 | B | 2-[(2-amino-acetyl)-phenyl-amino]-ethyl |

TABLE 5

Exemplary Compounds of Formula I-E

| Compound # | Structure | EC50 | X/Y |
|---|---|---|---|
| 36 | 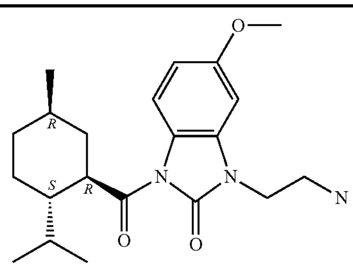 | A | 3-(2-Amino-ethyl)-5-methoxy-1,3-dihydro-benzoimidazol-2-one |
| 37 | 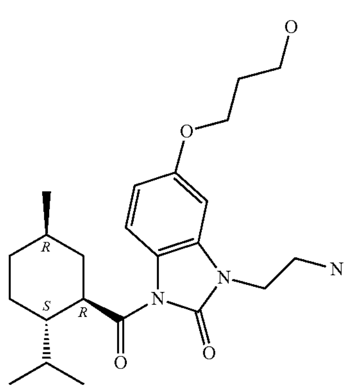 | A | 3-(2-Amino-ethyl)-5-(3-hydroxy-propoxy)-1,3-dihydro-benzoimidazol-2-one |

TABLE 5-continued

Exemplary Compounds of Formula I-E

| Compound # | Structure | EC50 | X/Y |
|---|---|---|---|
| 38 | 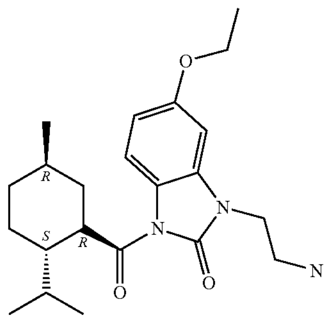 | A | 3-(2-Amino-ethyl)-5-ethoxy-1,3-dihydro-benzoimidazol-2-one |
| 39 | 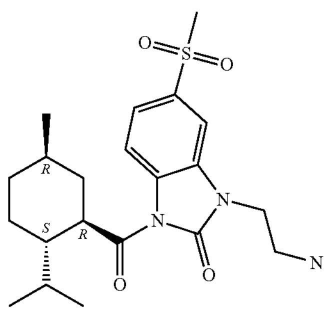 | A | 3-(2-Amino-ethyl)-5-methanesulfonyl-1,3-dihydro-benzoimidazol-2-one |
| 40 | 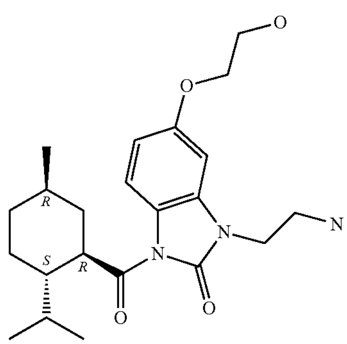 | A | 3-(2-Amino-ethyl)-5-(2-hydroxy-ethoxy)-1,3-dihydro-benzoimidazol-2-one |
| 41 | 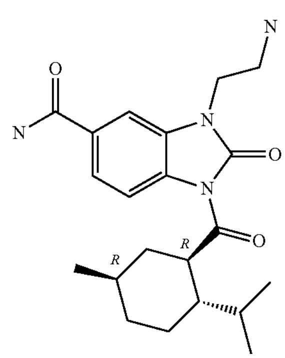 | A | 3-(2-Amino-ethyl)-2-oxo-2,3-dihydro-1H-benzoimidazole-5-carboxylic acid amide |

TABLE 5-continued

Exemplary Compounds of Formula I-E

| Compound # | Structure | EC50 | X/Y |
|---|---|---|---|
| 42 | 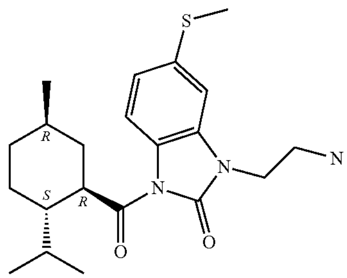 | A | 3-(2-Amino-ethyl)-5-methylsulfanyl-1,3-dihydro-benzoimidazol-2-one |
| 43 | 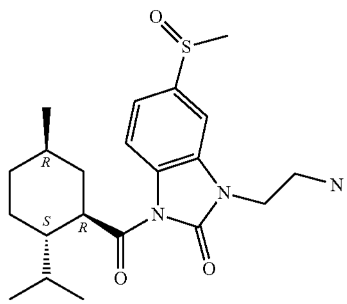 | A | 3-(2-Amino-ethyl)-5-methanesulfinyl-1,3-dihydro-benzoimidazol-2-one |
| 44 | 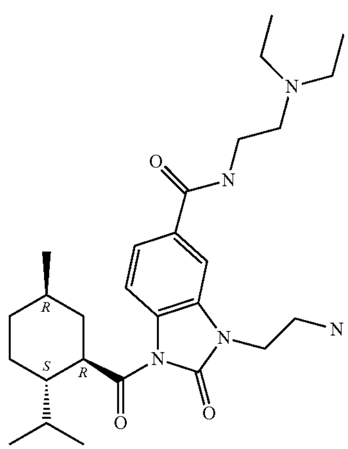 | A | 3-(2-Amino-ethyl)-2-oxo-2,3-dihydro-1H-benzoimidazole-5-carboxylic acid (2-diethylamino-ethyl)-amide |
| 45 | 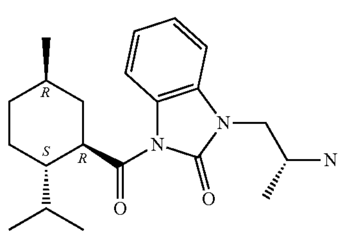 | A | 3-(2-Amino-propyl)-2,3-dihydro-benzoimidazol-2-one |

TABLE 5-continued

Exemplary Compounds of Formula I-E

| Compound # | Structure | EC50 | X/Y |
|---|---|---|---|
| 46 | 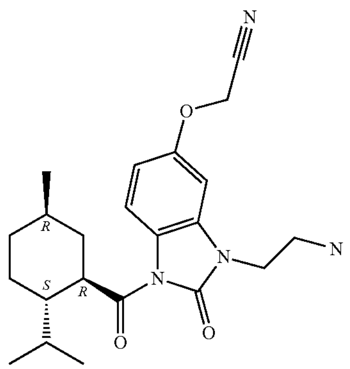 | A | [3-(2-Amino-ethyl)-2-oxo-2,3-dihydro-1H-benzoimidazol-5-yloxy]-acetonitrile |
| 47 | 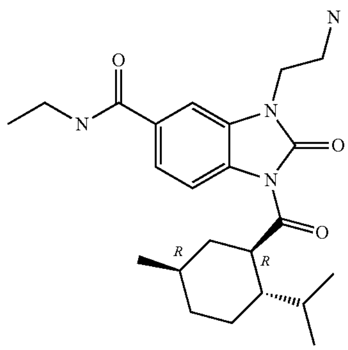 | A | 3-(2-Amino-ethyl)-2-oxo-2,3-dihydro-1H-benzoimidazole-5-carboxylic acid ethylamide |
| 48 | 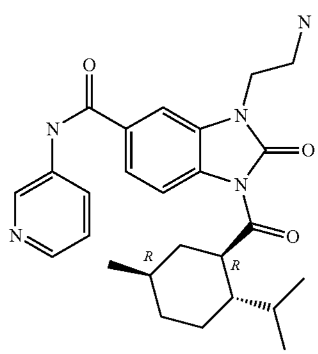 | A | 3-(2-Amino-ethyl)-2-oxo-2,3-dihydro-1H-benzoimidazole-5-carboxylic acid pyridin-3-ylamide |
| 49 | 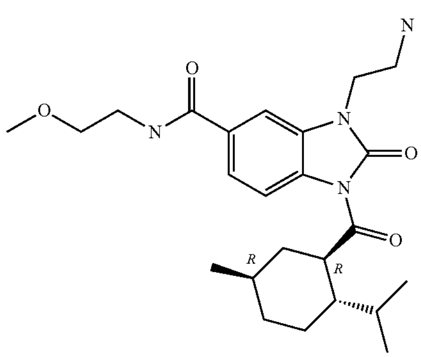 | A | 3-(2-Amino-ethyl)-2-oxo-2,3-dihydro-1H-benzoimidazole-5-carboxylic acid (2-methoxy-ethyl)-amide |

TABLE 5-continued

Exemplary Compounds of Formula I-E

| Compound # | Structure | EC50 | X/Y |
|---|---|---|---|
| 50 | 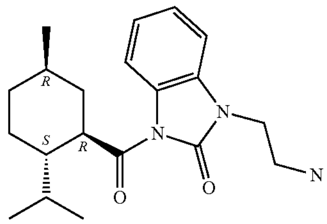 | A | 1-(2-Amino-ethyl)-1,3-dihydro-benzoimidazol-2-one |
| 51 | 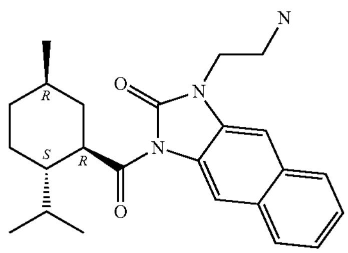 | A | 1-(2-Amino-ethyl)-1,3-dihydro-naphtho[2,3-d]imidazol-2-one |
| 52 | 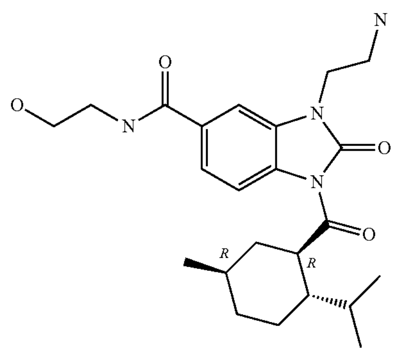 | A | 3-(2-Amino-ethyl)-2-oxo-2,3-dihydro-1H-benzoimidazole-5-carboxylic acid (2-hydroxy-ethyl)-amide |
| 53 | 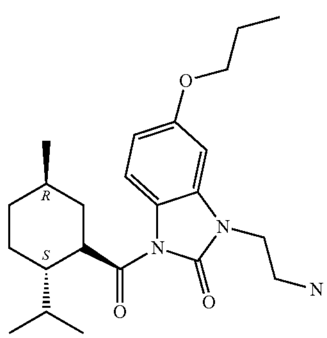 | A | 3-(2-Amino-ethyl)-5-propoxy-1,3-dihydro-benzoimidazol-2-one |
| 54 | 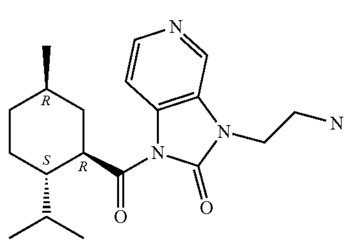 | B | 3-(2-Amino-ethyl)-1,3-dihydro-imidazo[4,5-c]pyridin-2-one |

TABLE 5-continued

Exemplary Compounds of Formula I-E

| Compound # | Structure | EC50 | X/Y |
|---|---|---|---|
| 55 | 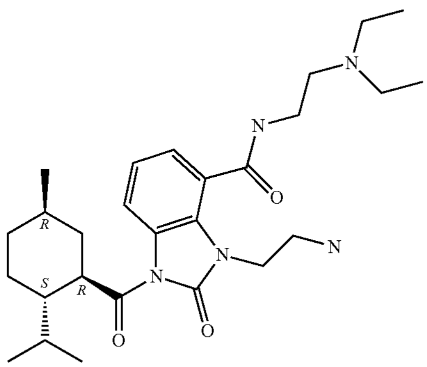 | B | 3-(2-Amino-ethyl)-2-oxo-2,3-dihydro-1H-benzoimidazole-4-carboxylic acid (2-diethylamino-ethyl)-amide |
| 56 | 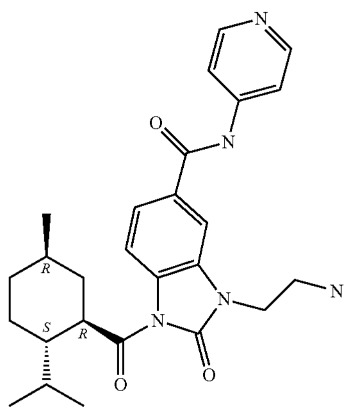 | B | 3-(2-Amino-ethyl)-2-oxo-2,3-dihydro-1H-benzoimidazole-5-carboxylic acid pyridin-4-ylamide |
| 57 | 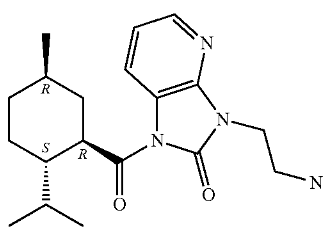 | B | 3-(2-Amino-ethyl)-1,3-dihydro-imidazo[4,5-b]pyridin-2-one |
| 58 | 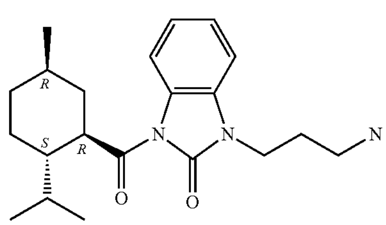 | B | 1-(3-Amino-propyl)-1,3-dihydro-benzoimidazol-2-one |
| 59 | 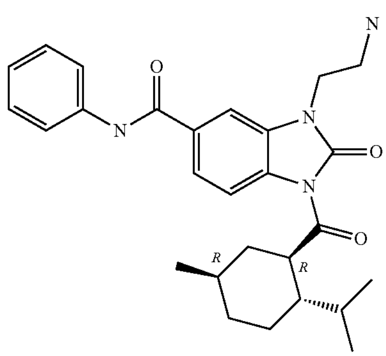 | B | 3-(2-Amino-ethyl)-2-oxo-2,3-dihydro-1H-benzoimidazole-5-carboxylic acid phenylamide |

TABLE 5-continued

Exemplary Compounds of Formula I-E

| Compound # | Structure | EC50 | X/Y |
|---|---|---|---|
| 60 | 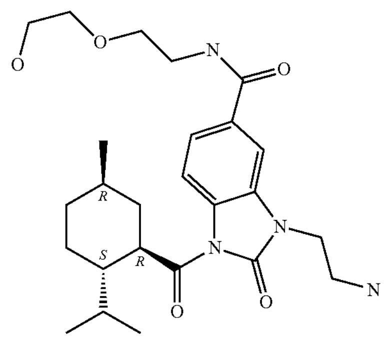 | B | 3-(2-Amino-ethyl)-2-oxo-2,3-dihydro-1H-benzoimidazole-5-carboxylic acid [2-(2-hydroxy-ethoxy)-ethyl]-amide |
| 61 | 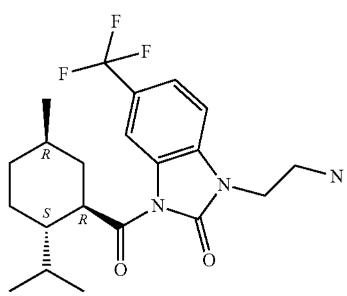 | B | 1-(2-Amino-ethyl)-5-trifluoromethyl-1,3-dihydro-benzoimidazol-2-one |
| 62 | 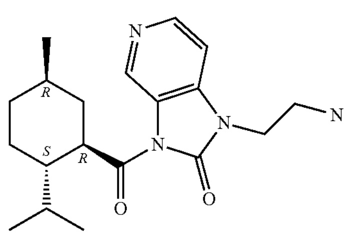 | B | 1-(2-Amino-ethyl)-1,3-dihydro-imidazo[4,5-c]pyridin-2-one |
| 63 | 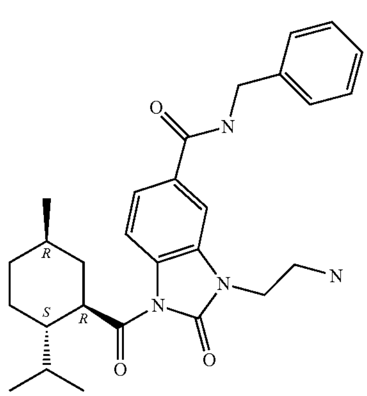 | B | 3-(2-Amino-ethyl)-2-oxo-2,3-dihydro-1H-benzoimidazole-5-carboxylic acid benzylamide |

TABLE 5-continued

Exemplary Compounds of Formula I-E

| Compound # | Structure | EC50 | X/Y |
|---|---|---|---|
| 64 | 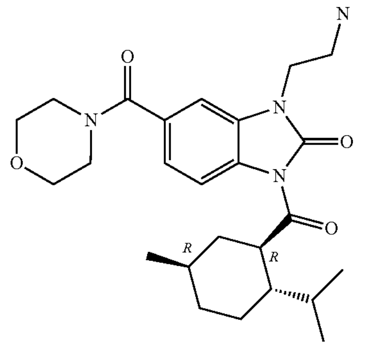 | B | 3-(2-Amino-ethyl)-5-(morpholine-4-carbonyl)-1,3-dihydro-benzoimidazol-2-one |
| 65 | 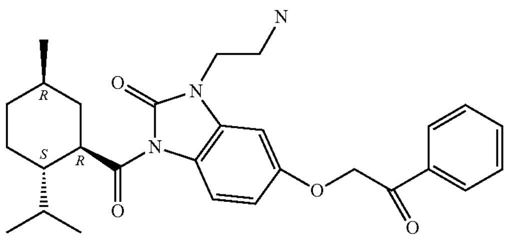 | B | 3-(2-Amino-ethyl)-5-(2-oxo-2-phenyl-ethoxy)-1,3-dihydro-benzoimidazol-2-one |
| 66 | 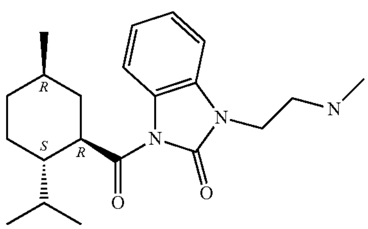 | B | 3-(2-methylamino-ethyl)-1,3-dihydro-benzoimidazol-2-one |
| 67 | 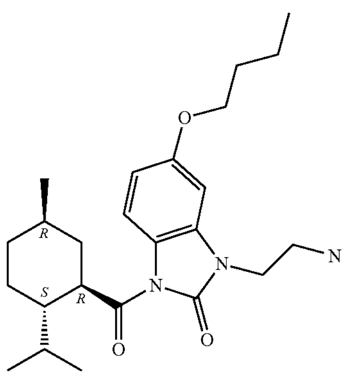 | C | 3-(2-Amino-ethyl)-5-butoxy-1,3-dihydro-benzoimidazol-2-one |
| 68 | 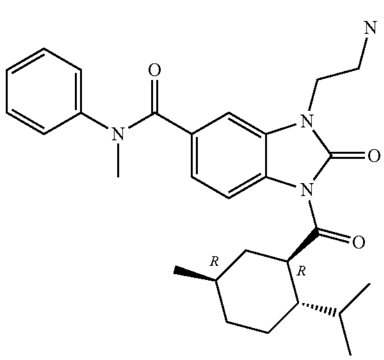 | C | 3-(2-Amino-ethyl)-2-oxo-2,3-dihydro-1H-benzoimidazole-5-carboxylic acid methyl-phenyl-amide |

TABLE 5-continued

Exemplary Compounds of Formula I-E

| Compound # | Structure | EC50 | X/Y |
|---|---|---|---|
| 69 | 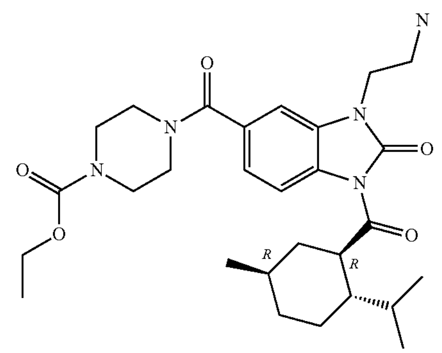 | C | 4-[3-(2-Amino-ethyl)-2-oxo-2,3-dihydro-1H-benzoimidazole-5-carbonyl]-piperazine-1-carboxylic acid ethyl ester |
| 70 | 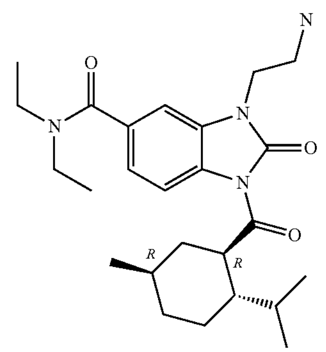 | C | 3-(2-Amino-ethyl)-2-oxo-2,3-dihydro-1H-benzoimidazole-5-carboxylic acid diethylamide |
| 71 | 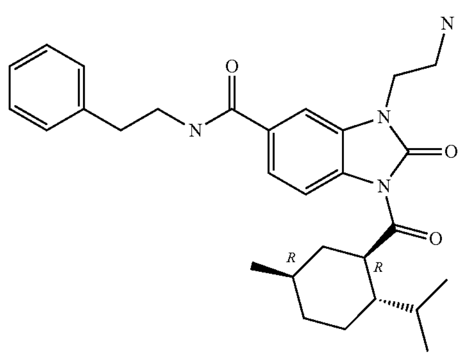 | C | 3-(2-Amino-ethyl)-2-oxo-2,3-dihydro-1H-benzoimidazole-5-carboxylic acid phenethyl-amide |
| 72 | 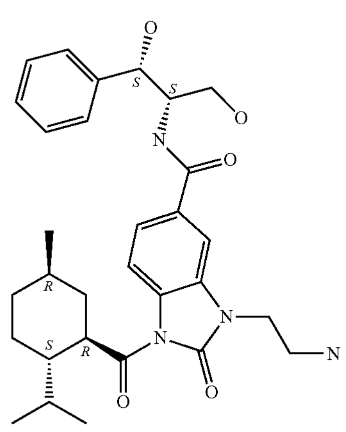 | C | 3-(2-Amino-ethyl)-2-oxo-2,3-dihydro-1H-benzoimidazole-5-carboxylic acid (2-hydroxy-1-hydroxymethyl-2-phenyl-ethyl)-amide |

TABLE 5-continued

Exemplary Compounds of Formula I-E

| Compound # | Structure | EC50 | X/Y |
|---|---|---|---|
| 73 | 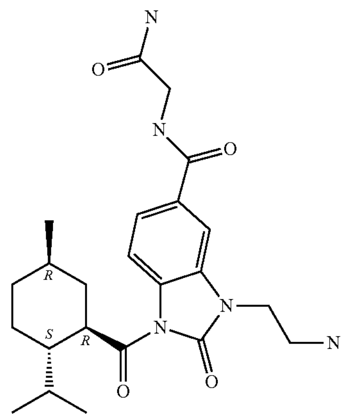 | C | 3-(2-Amino-ethyl)-2-oxo-2,3-dihydro-1H-benzoimidazole-5-carboxylic acid carbamoylmethyl-amide |
| 74 | 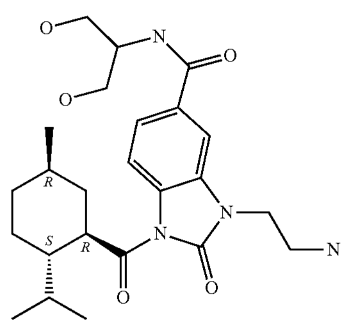 | C | 3-(2-Amino-ethyl)-2-oxo-2,3-dihydro-1H-benzoimidazole-5-carboxylic acid (2-hydroxy-1-hydroxymethyl-ethyl)-amide |
| 75 | 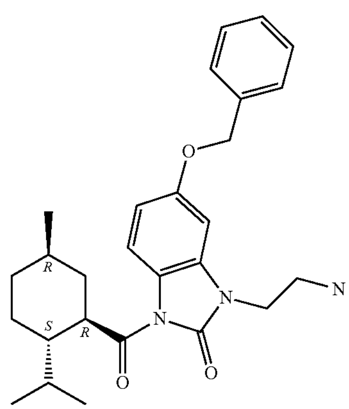 | C | 3-(2-Amino-ethyl)-5-benzyloxy-1,3-dihydro-benzoimidazol-2-one |
| 76 | 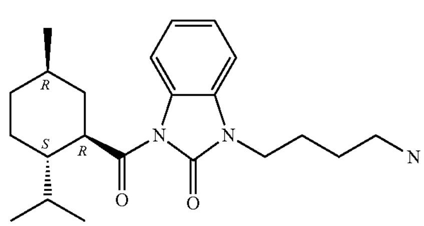 | C | 1-(4-Amino-butyl)-1,3-dihydro-benzoimidazol-2-one |

Example 12

Screen and Characterization of Trp-p8 Agonist Compounds by Measuring Calcium Influx in CHO/Trp-p8 cells at 37° C.

This example discloses a CHO/Trp-p8-based calcium influx assay used to further assess the activity of candidate Trp-p8 agonists of the present invention.

Calcium influx was measured using a Flexstation Microplate Fluorescence Plate Reader (Molecular Devices; Sunnyvale, Calif.). A typical assay for calcium flux was performed as follows. Cells in DMEM/Ham's F-12 based medium, typically at a density of 30,000 cells/well/100 µl, were plated in a 96-well black-walled, clear bottomed tissue culture plate (Greiner Bio-one) and incubated for 16-20 hours at 37° C. Cells in each well were incubated for one hour at 37° C. with a Fura2-AM Fluorescent Dye/Pluronic F-27 mixture (Molecular Probes; Eugene, Oreg.) and dissolved in the medium containing Probenecid. Typical final concentrations were: 5-8 µM of Fura2-AM, 0.01% Pluronic F-27, and 2.5 mM Probenecid (an anion exchange inhibitor that reduces transport of the hydrolyzed dye from inside the cell thereby minimizing loss of dye during the experiment). After one hour, cells were washed in a buffered solution (20 mM HEPES and Hanks Balanced Salt Solution with 1.26 mM $CaCl_2$), pH 7.4 containing Probenecid at a final concentration of 2.5 mM and pre-incubated for at least 30 minutes at the assay temperature of 37° C.

Typically, the above described HEPES/HBSS-based buffer containing either no additional calcium or with calcium to increase the concentration to 2 mM and various concentrations of compounds (at 5-times the final concentrations) were added to each well using the robotic multi-channel pipettor. The compounds were preincubated at 37° C. for at least 30 minutes before performing the assay (at 37° C.). Signals were read with dual excitation wavelengths of 340 and 380 nm and emission wavelength of 510 nm with a cut-off filter at 495 nm. The signal was reported as the ratio of emission when excited at 340 nm to the emission when excited at 380 nm [Relative Fluorescence Units (RFU)]. Ionomycin was routinely used as a positive control.

Figure 2B:
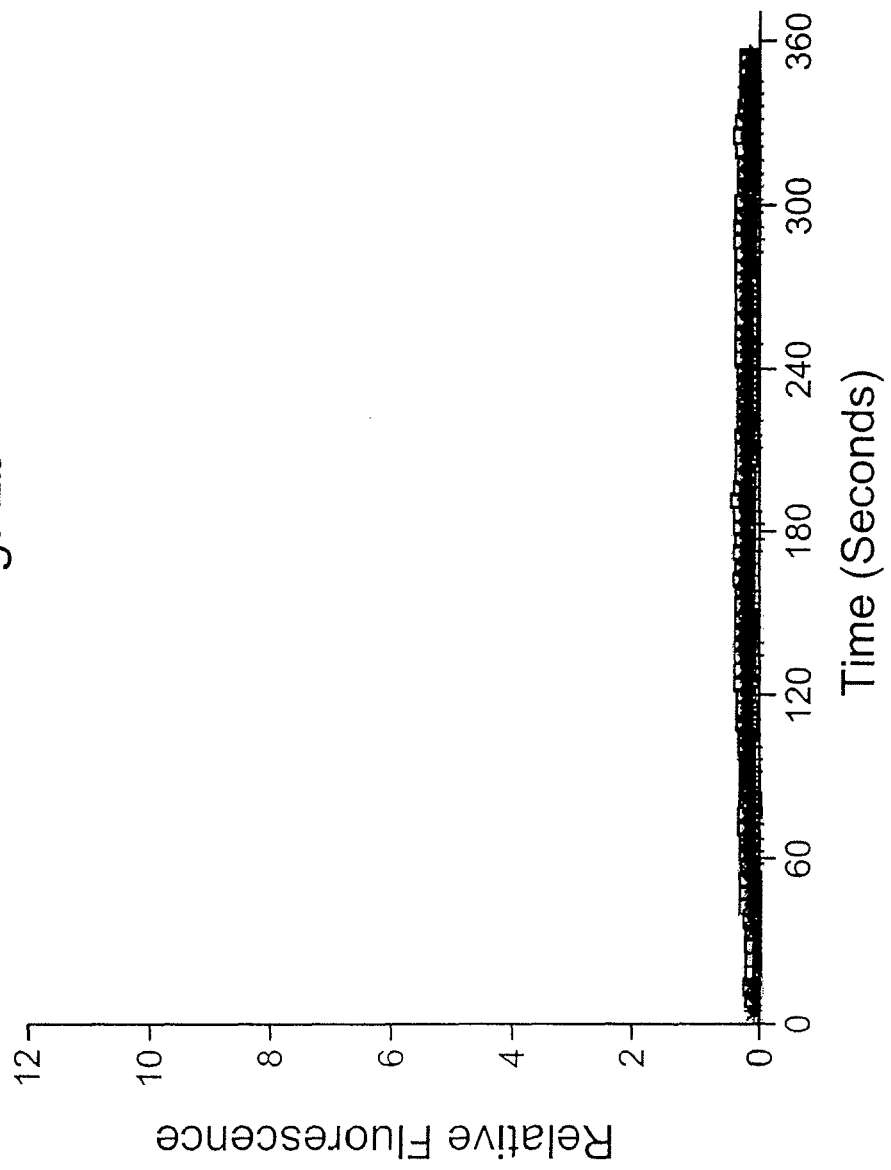
Figure 2C:
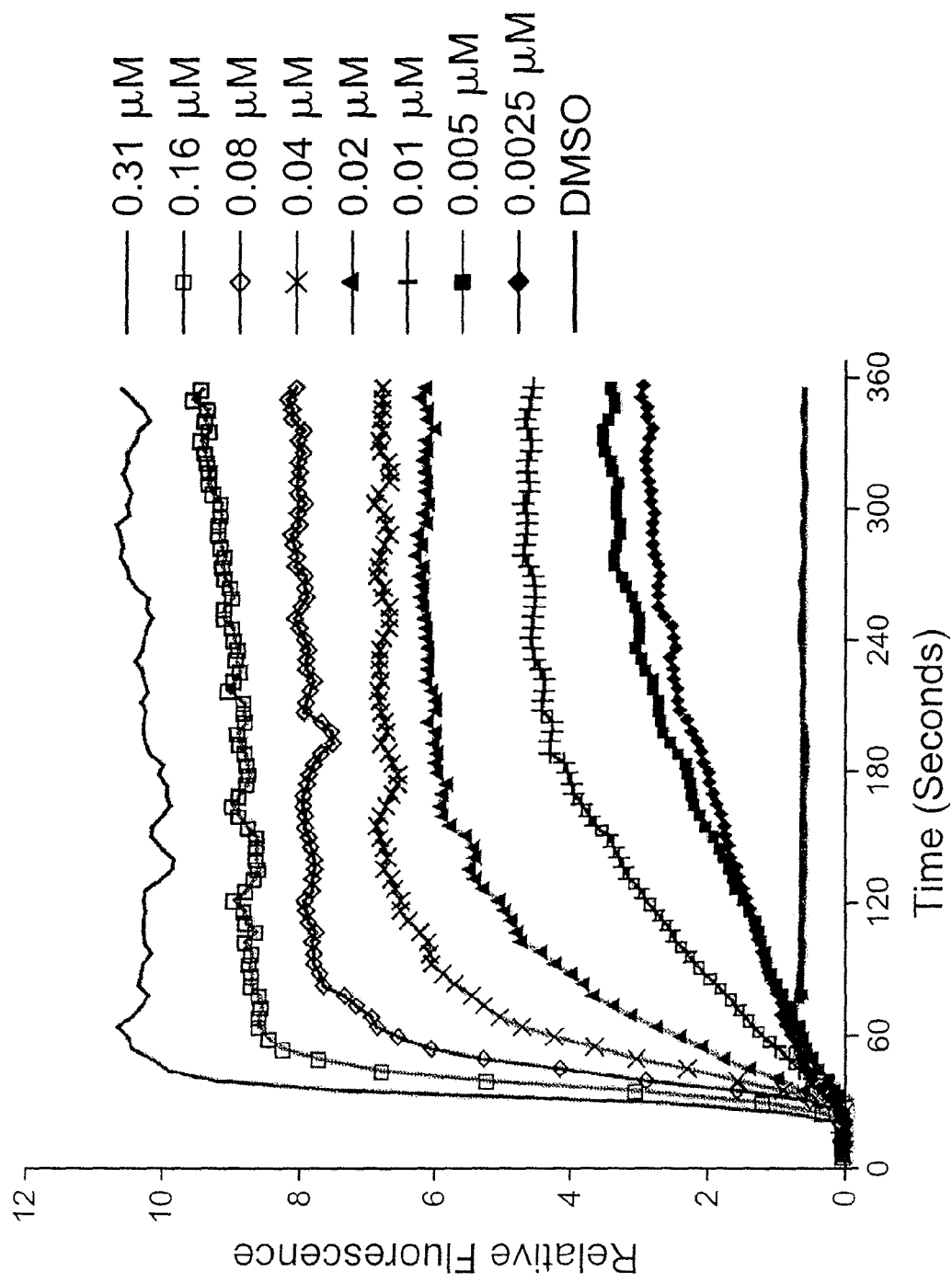

In the case of the agonist assay, the compounds at different concentrations were added to the dye-loaded cells (as described above). The increase in RFU was a measure of potency of the compound as an agonist. Exemplary results are presented in FIG. 2.

Example 13

Increase in Apoptosis following Exposure of CHO/Trp-p8 Cells with Trp-p8 Agonist Compounds at 37° C.

This example discloses the effectiveness of Trp-p8 agonist compounds in inducing apoptosis in Trp-p8 expressing cells.

An Annexin V/Propidium Iodide (PI) flow cytometry assay was used to provide additional insights into the mechanism of cell death induced by Trp-p8 agonist compounds. Annexin V staining detects translocation of Phosphatidylserine to the outer layer of plasma membrane, an event characteristic of apoptosis, while PI staining indicates dead cells with compromised membranes.

Cells were treated with compounds in 1% DMSO or with a 1% DMSO (control) for 24-26 hours at 37° C. The cells were briefly trypsinized under controlled conditions and stained with an Annexin V/PI reagent kit following the methodology provided by the supplier (e.g., Southern Biotech; Birmingham, Ala.). Exemplary results are presented in FIG. 3.

Example 14

In Vitro Screen using a Cell Viability Assay for Trp-p8 Antagonist Compounds Based Upon Protection of Trp-p8-Expressing Cells from Toxic Agonist Compounds This example discloses an assay system for identifying and characterizing candidate Trp-p8 antagonist compounds.

Trp-p8 antagonists were identified by employing a cell viability assay with CHO/Trp-p8 cells at 37° C. (see Example 11) with the following modification. Within the context of the present invention, compounds that protect CHO/Trp-p8 cells from the toxic effect of a control agonist thereby maintaining the viability of the CHO/Trp-p8 cell exposed to a Trp-p8 agonist is defined as antagonist. As a primary screen for antagonists, CHO/Trp-p8 cells were exposed to 10 µM of test compounds in 1% dimethylsulfoxide (DMSO) or 1% DMSO plus a toxic concentration of a control agonist. The relative viability at 10 µM, determined as described in Example 11, was a measure of the potential of the compound as a Trp-p8 antagonist—the higher the viability, the more potent the antagonist. Exemplary results are presented in FIG. 4.

Example 15

In Vitro Screen using a Calcium Flux Assay for Trp-p8 Antagonist Compounds Based upon their Abilities to Suppress the Calcium Influx Induced by Trp-p8 Agonists in CHO/Trp-p8 Cells This example discloses an in vitro assay system employed to further screen and characterize candidate Trp-p8 antagonists.

Trp-p8 antagonists were also screened and characterized using a calcium flux assay at 37° C. as described in Example 12 with the following two distinctions: (1) the compound was pre-mixed with the control agonist or only the control agonist is added to the cells and suppression of the response to the agonist is a measure of the potency of the compound as an antagonist and (2) the compound, at different concentrations, was added to the cells followed by addition of the control agonist after 2-3 minutes and the suppression of response induced by agonist was a measure of potency of the compound as an antagonist. Exemplary results are presented in FIG. 5.

Example 16

An Animal Model System for Assaying the In vivo Efficacy of Candidate Trp-p8 Agonists and Antagonists for the Treatment of Cancer This Example provides an animal model system suitable for determining the in vivo efficacy of candidate Trp-p8 modulators—including both agonists and antagonists.

Human prostate cancer xenografts expressing Trp-p8 (LuCaP, from Dr. Robert Vessella's lab in University of Washington—as assessed by in situ hybridization, quantitative polymerase chain reaction, and immunohistochemistry using a protein specific rabbit polyclonal antibody, T-904), as well as cell lines engineered to express Trp-p8, including CHO (Chinese Hamster Ovary) and EL-4 (Mouse Thymoma) cell lines, were used to establish tumor models in mice. Trp-p8 expression in the transfectants was confirmed by western blots and immunofluorescence using a Trp-p8 specific antibody (GS 2.20) as well as by response to known agonists in a calcium influx functional assay. In addition, the transfected cell lines were susceptible to killing by Trp-p8 agonists as evident from the ATP viability and apoptosis assays (as described herein in Examples 11 and 13).

A tumor model in mice was established by subcutaneously injecting CHO/Trp-p8 cells in SCID mice. Trp-p8 expression in tumors excised from these mice was confirmed by RT-PCR, immunohistochemistry, and western blot analysis. Further tumor model development is carried out using the human prostate cancer xenografts described above in athymic nude or SCID mice and using an EL4/Trp-p8 transfectant in normal mice. Prostate xenografts from other sources and other cell lines that may be engineered to express Trp-p8 are also potential candidates for building more model systems.

Based on results from in vitro and in vivo evaluations, a set of Trp-p8 agonists will be chosen to determine efficacy in mice. The in vitro evaluations would include potency in cell killing assay, aqueous solubility, plasma binding study and metabolic stability (potential for a compound to be metabolized by liver as determined by using hepatocytes and/or mouse microsomes). The in vivo evaluations would include pharmacokinetics and toxicity studies. The chosen compounds will be administered to mice with Trp-p8 expressing tumors by different routes [oral, intravenous, intraperitoneal, subcutaneous, intramuscular]. Tumor reduction and survival of these mice will be evaluated at different dosages of these compounds. The compound most effective in fighting tumor will be chosen for further investigations Example 17

Experimental Characterization of Several Exemplary Compounds

This Example discloses the experimental characterization and results of several exemplary small-molecule Trp-p8 modulators of Formula I, designated Compound I, II, III and IV. Their chemical formulas and molecular weight are summarized in Table 6.

TABLE 6

Chemical Formulas and Molecular Weights

| | Compound | | | |
|---|---|---|---|---|
| | I | II | III | IV |
| Chemical Formula | $C_{21}H_{31}N_3O_3$ | $C_{20}H_{29}N_3O_2$ | $C_{22}H_{32}N_4O$ | $C_{21}H_{34}N_2O_2$ |
| Molecular Weight | 373 | 343 | 368 | 346 |

In Vitro Activity

As summarized in Table 8, the compounds demonstrated a high degree of potency and specificity towards killing cells that express Trp-p8. Typically, >1000× higher concentrations of compound were required to kill cells lacking Trp-p8, compared to cells that express Trp-p8. Compounds II, III, and IV showed similar activity in this assay, while Compound I was approximately 3 times more potent.

TABLE 8

Results of ATP viability assay for several preferred compounds

| | Compound | | | |
|---|---|---|---|---|
| | I | II | III | IV |
| CHO/Trp-p8 $EC_{50}$ (uM) | 0.003 | 0.01 | 0.01 | 0.01 |
| Parent CHO $EC_{50}$ (uM) | >10 | >10 | >10 | >10 |

In Vivo Activity

Figure 9A:
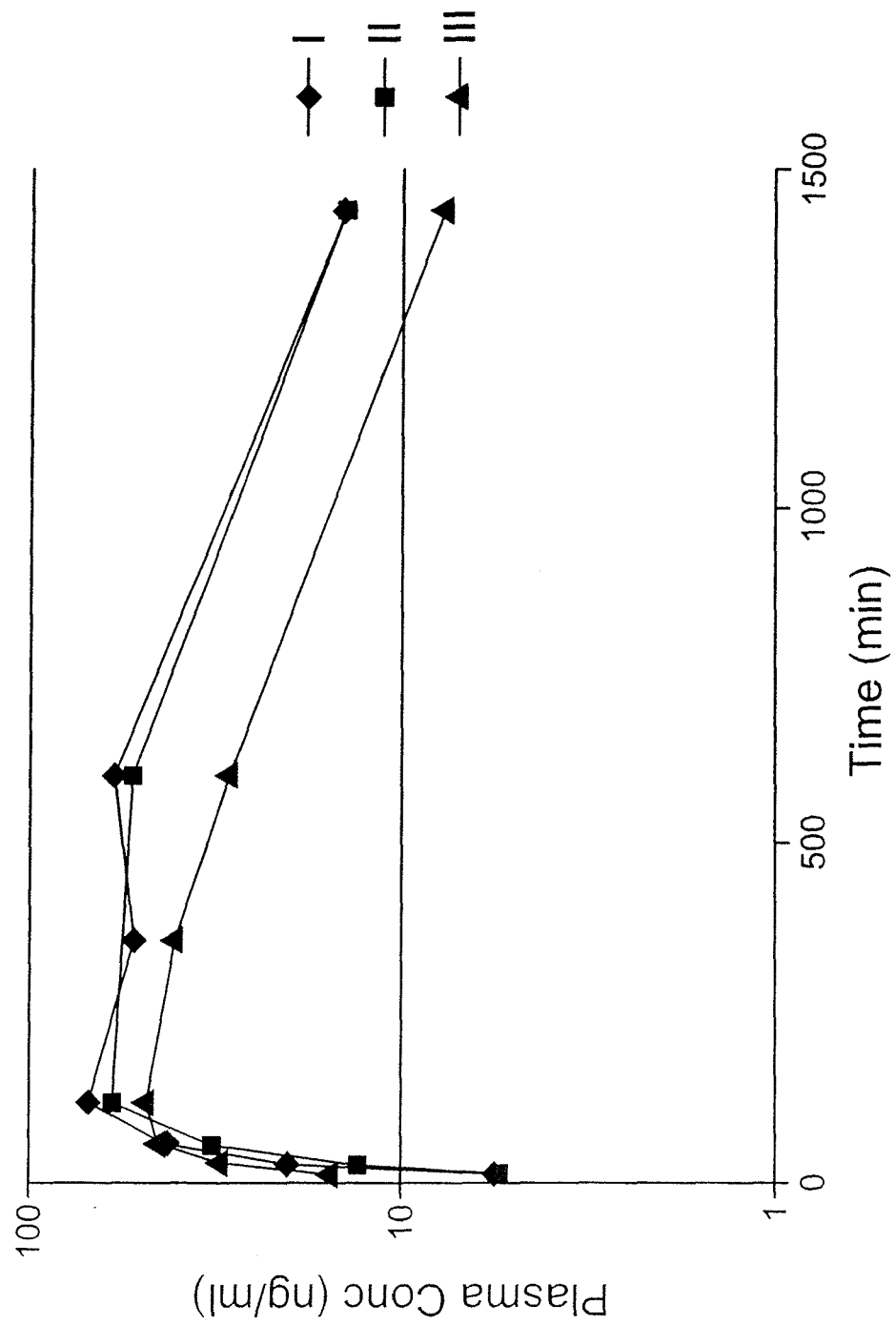
FIGS. 9A and 9B are graphs depicting the plasma concentrations of several compounds, as a function of time and dose, in rats (FIG. 9A), and dogs (FIG. 9B) after a single oral dose. The compounds were all dissolved in an aqueous formulation, and administered at comparable dose levels by oral gavage. Blood was collected at the indicated time points, and analyzed for drug levels.
Figure 9B:
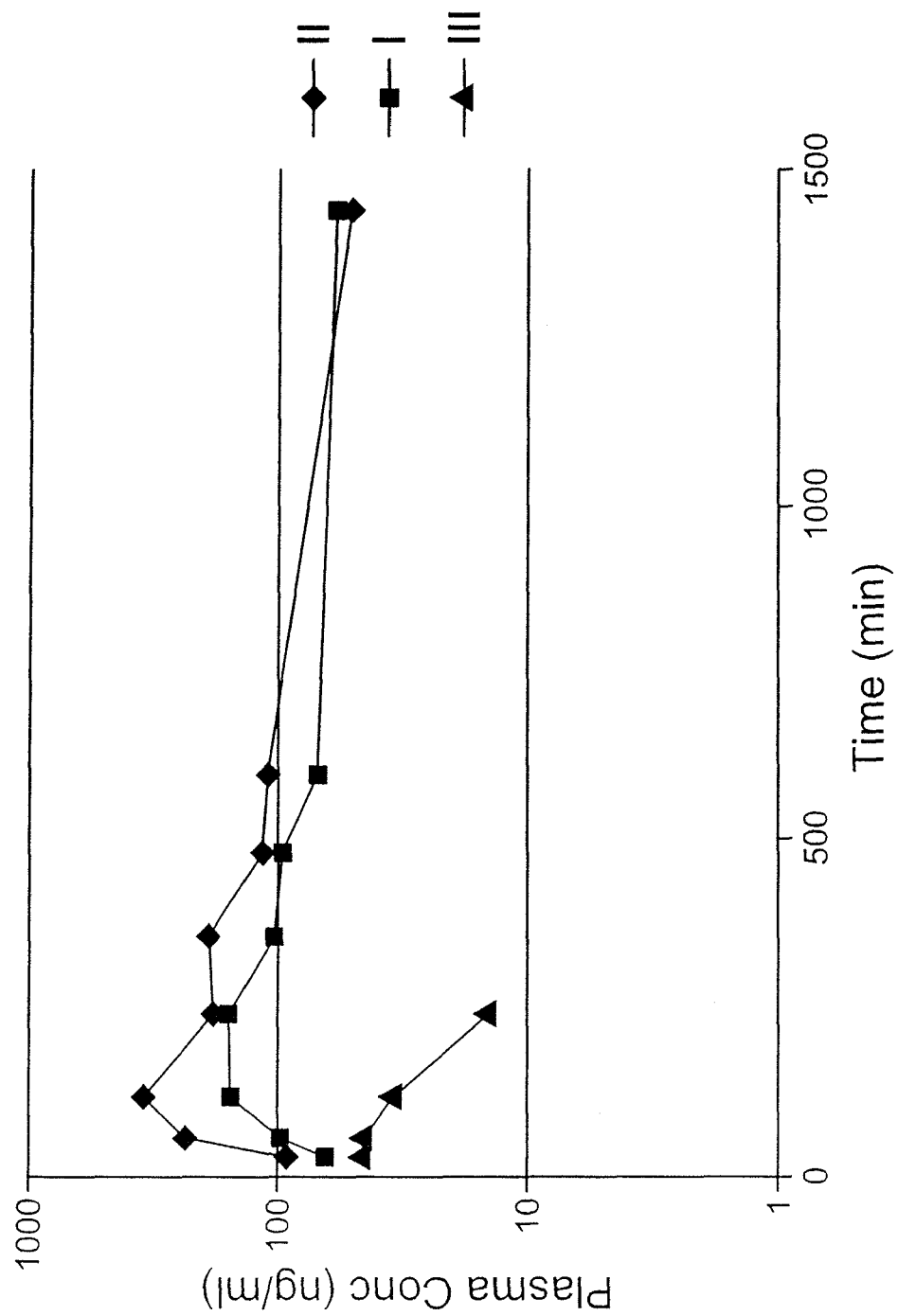

As illustrated in FIGS. 9A and 9B, Compounds I, II, and III produced prolonged exposure after a single oral administration in both rodents (FIG. 9A) and Beagle dogs (FIG. 9B). Compared to mice, rats require approximately twice the oral dose (based on body weight) to achieve comparable exposure, and dogs require less than a third. Consistent with the sustained plasma levels (t½~9 h), a single oral dose affords a prolonged durable response in the CHO/Trp-p8 xenograft model.

Figure 10A:
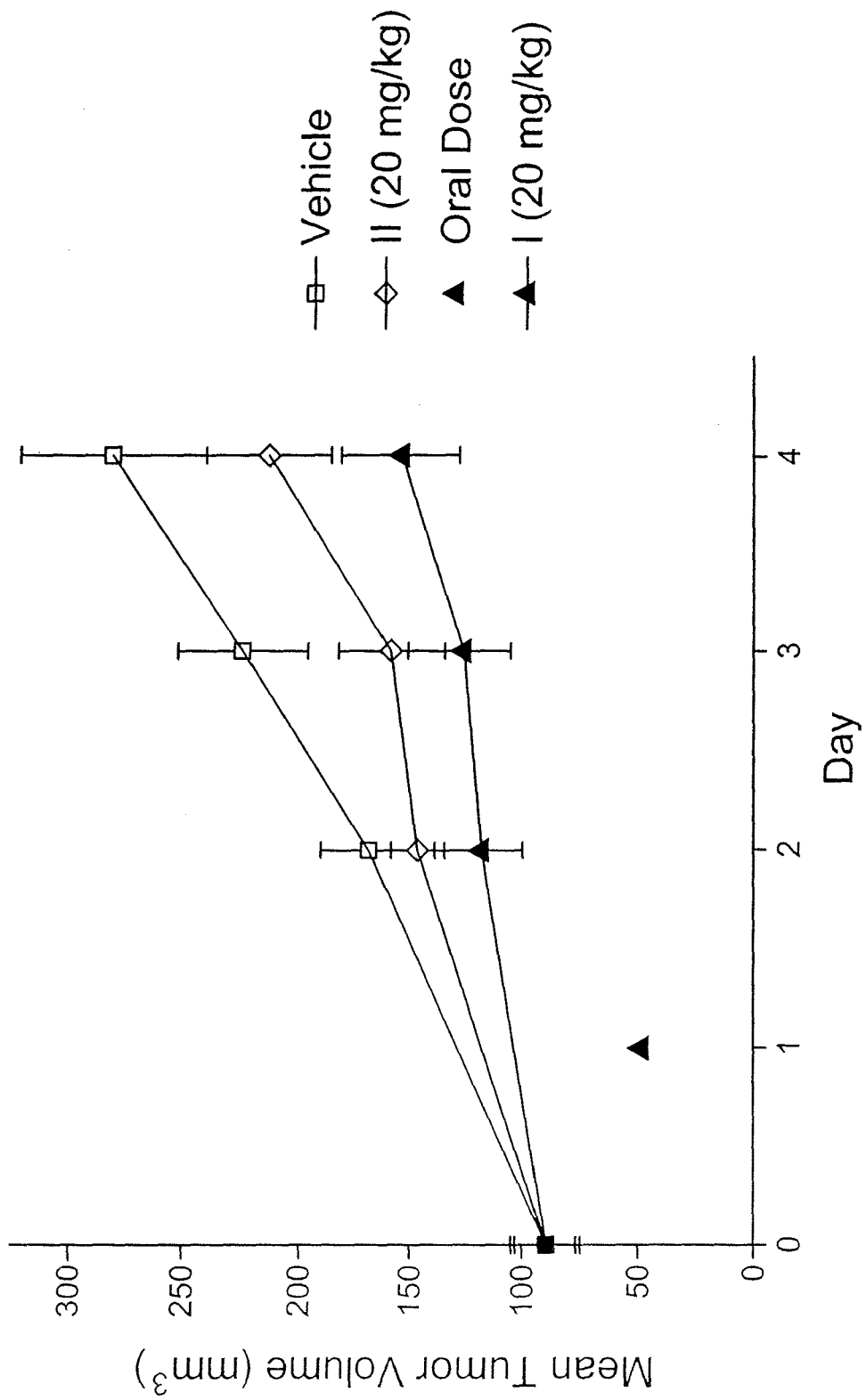
FIGS. 10A and 10B are graphs depicting the efficacy demonstrated by several compounds in a murine tumor xenograft model expressing Trp-p8. Mice were injected subcutaneously with CHO/Trp-p8 cells, resulting in the formation of solid tumors. The length (L; longest dimension) and width (W.
Figure 10B:
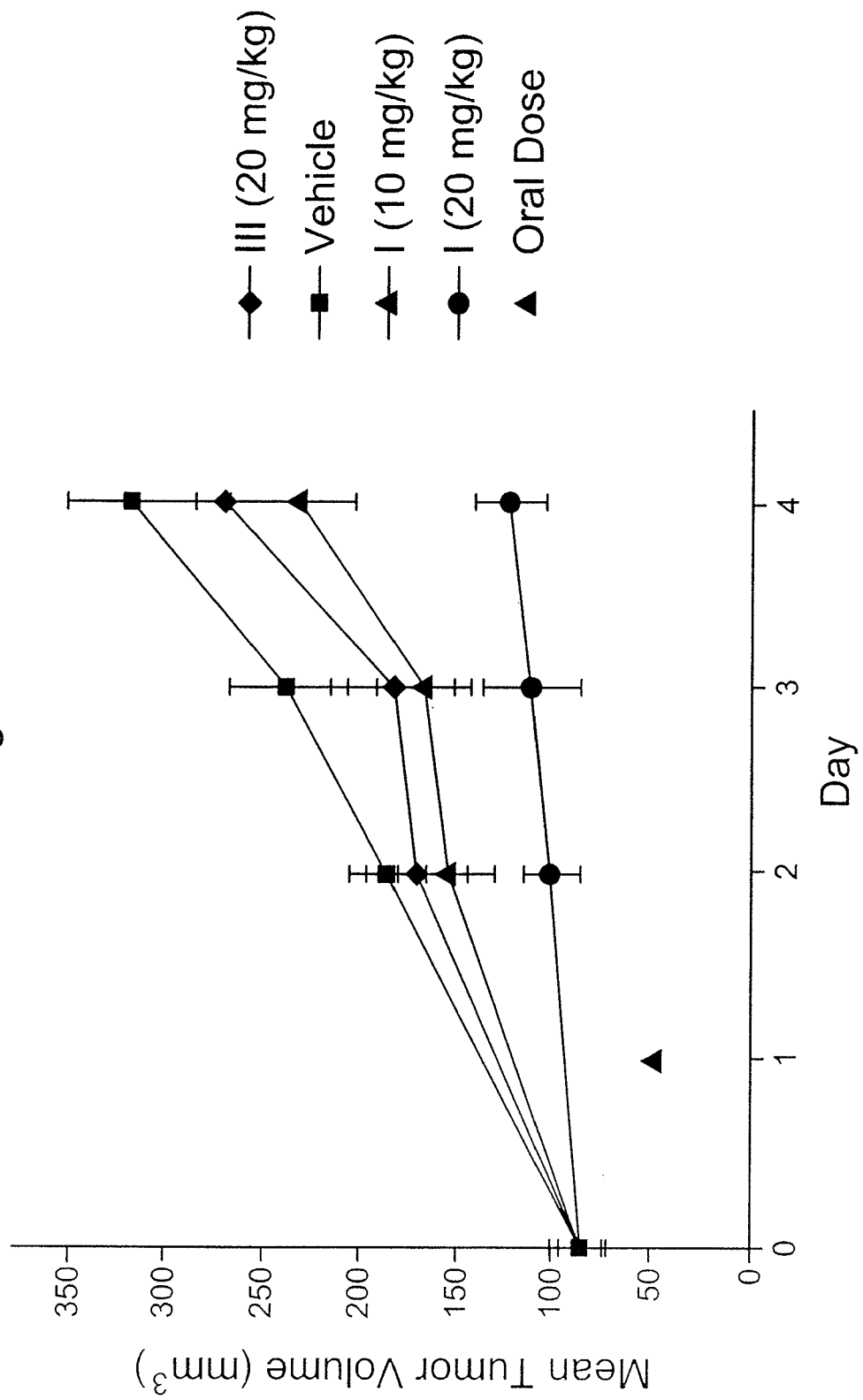

As illustrated in FIGS. 10A and 10B, oral dosing of these compounds afforded durable responses in the CHO/Trp-p8 xenograft model. Substantial inhibition of tumor growth was seen after a single dose as low as 10 mg/kg, and no significant toxicity was evident at 100 mg/kg; a therapeutic window of >10×.

Figure 7:
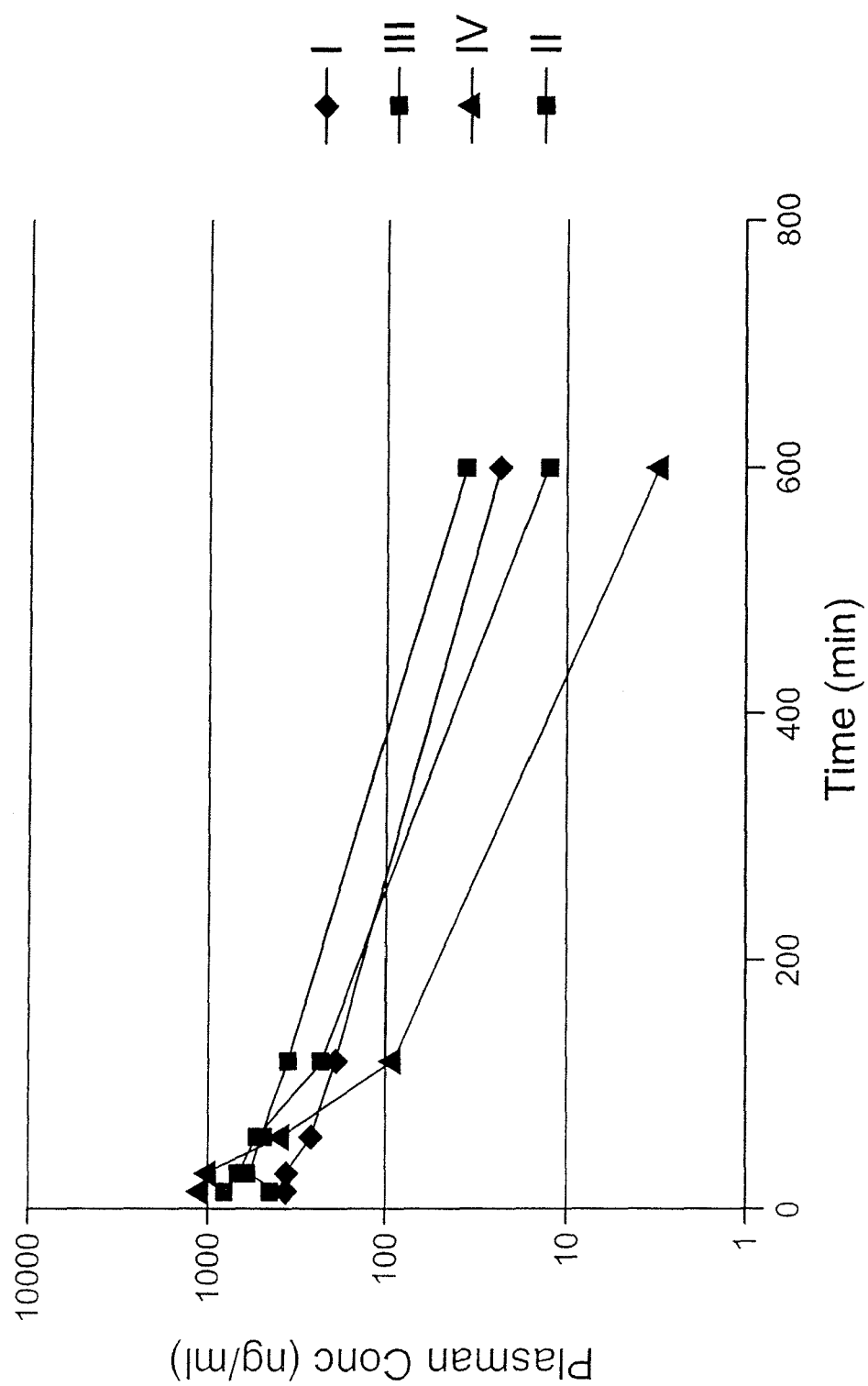
FIG. 7 is a graph depicting the plasma concentrations of several compounds, as a function of time and dose, in mice after administration via a single intraperitoneal injection. The compounds were all dissolved in an aqueous formulation, and administered at comparable dose levels. Blood was collected at the indicated time points, and analyzed for drug levels.
Figure 8A:
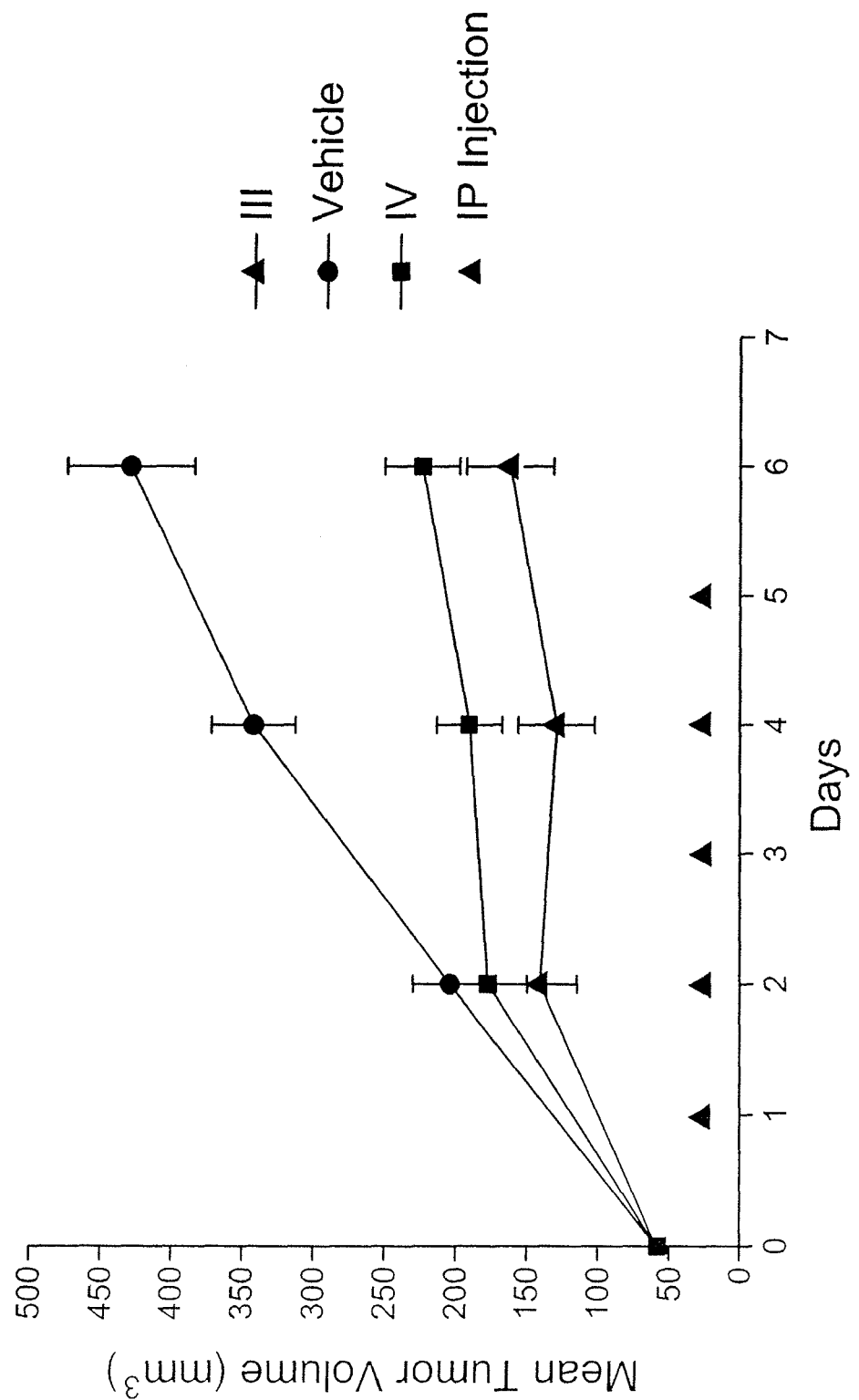
FIGS. 8A-8B are graphs depicting the efficacy demonstrated by several compounds in a murine tumor xenograft model expressing Trp-p8. Mice were injected subcutaneously with CHO/Trp-p8 cells, resulting in the formation of solid tumors. The length (L; longest dimension) and width (W; dimension perpendicular to and in the same plane as length) of each tumor was measured with calipers, and the tumor volume was approximated by a formula for the volume of an ellipsoid: $0.52*L*W^2$. When the mean tumor volume reached approximately 100 mm$^3$, the mice were randomized into groups, and administered either a compound as an aqueous formulation, or vehicle alone, by intraperitoneal injection, on the indicated days. All compounds were administered at comparable dose levels. Tumors were subsequently measured on the indicated days. The data is presented as mean tumor volumes±standard error of the mean.
Figure 8B:
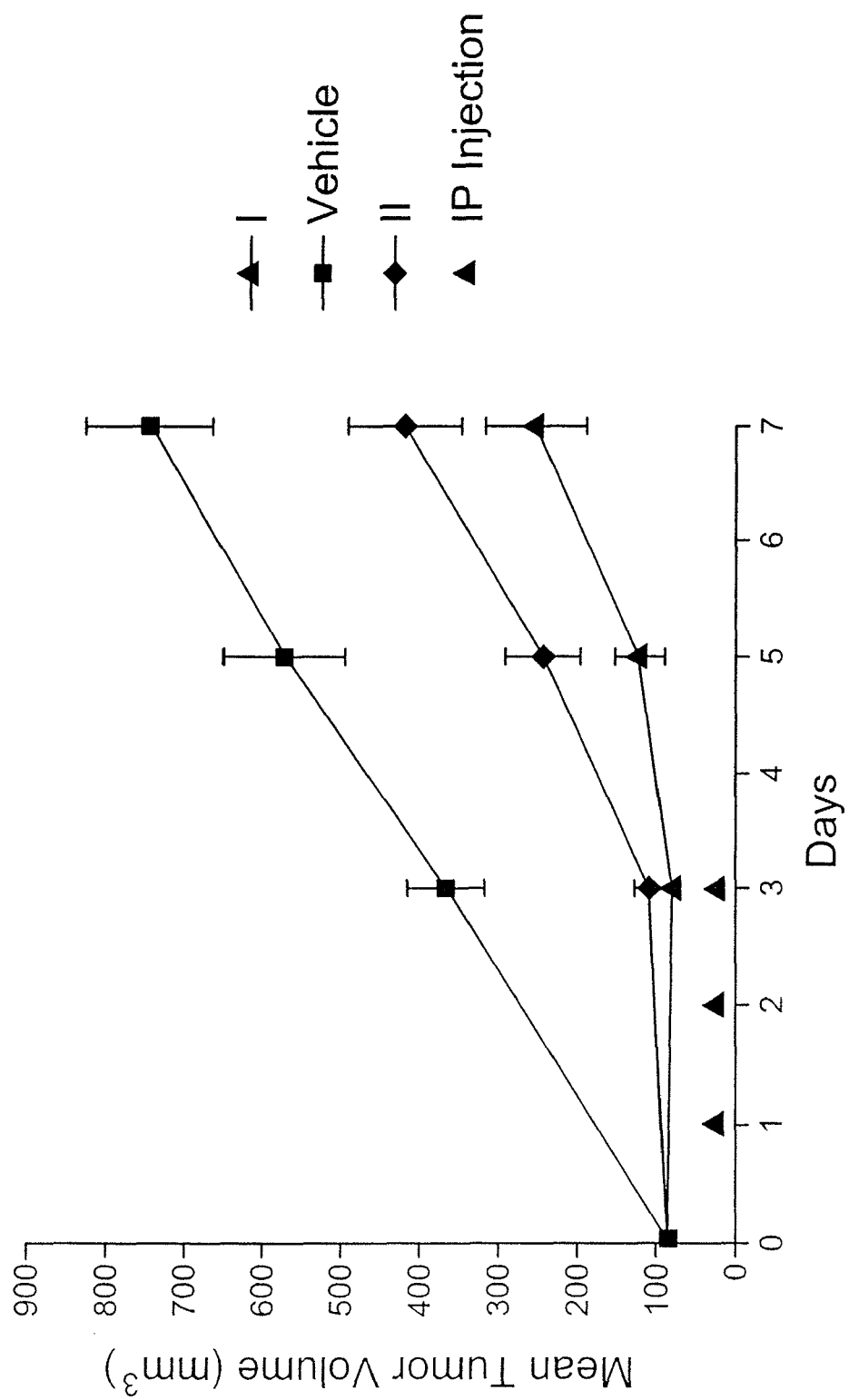

As illustrated in FIG. 7, compounds of Formula I generated substantially briefer exposure via a single intraperitoneal injection as compared to oral administration. As illustrated in FIGS. 8A and 8B, intraperitoneal injection of these compounds in mice results in briefer responses in the CHO/Trp-p8 xenograft model and appear less durable after cessation of IP dosing.

To demonstrate that efficacy is mediated by Trp-p8, FIG. 11 illustrates the evaluation of Compound I in the matched CHO (Trp-p8-) model. Consistent with the proposed mechanism of action, Compound I did not show significant efficacy at 100 mg/kg in this model; a dose 10 times higher than an efficacious dose in the analogous CHO/Trp-p8 model.

As illustrated in FIG. 12, the LuCaP model appeared to respond comparably or arguably better than the CHO/Trp-p8 model. CHO/Trp-p8 is a fast-growing tumor; treatment with Compound I attenuated growth, but did not cause regression. In contrast, LuCaP is a slower-growing tumor; treatment caused statistically significant regression, as well as growth-inhibition. In this instance, the LuCAP xenograft model exhibited levels of Trp-p8 comparable to the CHO/Trp-p8 model, as measured by immunohistochemistry of tumor tissues excised from the mice.

The highest dose orally administered to mice, 100 mg/kg, did not result in significant toxicity for any of the compounds. Since a single oral dose of 10 mg/kg of Compound I produced significant efficacy in the CHO/Trp-p8 xenograft model, a therapeutic window of >10 is achievable with Compounds of Formula I. This has been expanded upon by toxicology experiments in rats, where the compounds could be administered at higher dose levels. In toxicology studies performed in rats, oral doses of 250 mg/kg did not induce any observable toxic effects. Single Doses of 500 mg/kg and 1000 mg/kg resulted in mild to moderate toxicity, but the MTD was not reached. These data, representing the minimum therapeutic windows achievable with Compounds of Formula I, are summarized in Table 7.

TABLE 7

| Rat oral dose (mg/kg) | Observed degree of toxicity | Comparable mouse oral dose (mg/kg) | Multiple of lowest efficacious oral dose in mice |
|---|---|---|---|
| 250 | None | 125 | 12.5 |
| 500 | Mild | 250 | 25 |
| 1000 | Moderate | 500 | 50 |

Although the present invention has been described in some detail by way of illustration and example for purposes of clarity of understanding, changes and modifications can be carried out without departing from the scope of the invention which is intended to be limited only by the scope of the appended claims.

What is claimed is:

1. A compound of Formula I-B:

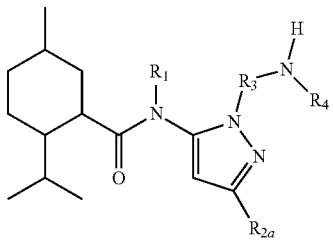

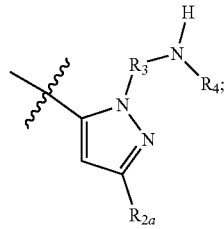

wherein $R_1$ is selected from the group consisting of H, alkyl, heteroalkyl, aryl, and arylalkyl;

$R_{2a}$ is selected from the group consisting of aryl, alkyl, heteroalkyl, and arylalkyl;

$R_3$ is selected from the group consisting of alkyl, heteroalkyl, and arylalkyl;

$R_4$ is selected from the group consisting of H, alkyl, heteroalkyl, and arylalkyl;

or a pharmaceutically acceptable salt thereof.

2. The compound of claim 1 or a pharmaceutically acceptable salt thereof wherein $R_1$ is H.

3. The compound of claim 1 or a pharmaceutically acceptable salt thereof wherein $R_3$ is alkyl, heteroalkyl or arylalkyl, each of which has 1, 2, 3, 4, 5, or 6 carbons.

4. The compound of claim 3 or a pharmaceutically acceptable salt thereof wherein $R_3$ is selected from methylene, ethylene, propylene, and butylene.

5. The compound of claim 1 or a pharmaceutically acceptable salt thereof wherein $R_4$ is selected from H and methyl.

6. The compound of claim 1 or a pharmaceutically acceptable salt thereof wherein $R_{2a}$ is a group selected from phenyl, furan, methylpyrrole, methylbenzoate, aminophenyl, hydroxyphenyl, cyanophenyl, and methoxyphenyl.

7. The compound of claim 1 or a pharmaceutically acceptable salt thereof wherein the moiety:

is selected from the group consisting of 2-(2-amino-ethyl)-5-furan-2-yl-2H-pyrazol-3-yl, 2-(2-amino-propyl)-5-phenyl-2H-pyrazol-3-yl, 2-(2-amino-ethyl)-5-phenyl-2H-pyrazol-3-yl, 2-(2-amino-ethyl)-5-(1-methyl-1H-pyrrol-2-yl)-2H-pyrazol-3-yl, 2-(2-amino-propyl)-5-phenyl-2H-pyrazol-3-yl, 2-(2-amino-ethyl)-5-(4-amino-phenyl)-2H-pyrazol-3-yl, 2-(2-amino-ethyl)-5-(4-hydroxy-phenyl)-2H-pyrazol-3-yl, 2-(2-methylamino-ethyl)-5-phenyl-2H-pyrazol-3-yl, 2-(2-amino-propyl)-5-phenyl-2H-pyrazol-3-yl, 2-(2-amino-ethyl)-5-(3-cyano-phenyl)-2H-pyrazol-3-yl, 2-(2-amino-ethyl)-5-(3-methoxy-phenyl)-2H-pyrazol-3-yl, 4-{1-(2-Amino-ethyl)-1H-pyrazol-3-yl}-benzoic acid methyl ester, 2-(2-amino-ethyl)-5-(3-amino-phenyl)-2H-pyrazol-3-yl, and 2-(2-amino-ethyl)-5-(3-hydroxy-phenyl)-2H-pyrazol-3-yl.

8. The compound of claim 7 wherein said compound is 2-isopropyl-5-methyl-cyclohexane carboxylic acid-[2-(2-amino-ethyl)-5-furan-2-yl-2H-pyrazol-3-yl]-amide, 2-isopropyl-5-methyl-cyclohexane carboxylic acid-[2-(2-amino-propyl)-5-phenyl-2H-pyrazol-3-yl]-amide, 2-isopropyl-5-methyl-cyclohexane carboxylic acid-[2-(2-amino-ethyl)-5-phenyl-2H-pyrazol-3-yl]-amide, 2-isopropyl-5-methyl-cyclohexane carboxylic acid-[2-(2-amino-ethyl)-5-(1-methyl-1H-pyrrol-2-yl)-2H-pyrazol-3-yl]-amide, 2-isopropyl-5-methyl-cyclohexane carboxylic acid-[2-(2-amino-propyl)-5-phenyl-2H-pyrazol-3-yl]-amide, 2-isopropyl-5-methyl-cyclohexane carboxylic acid-[2-(2-amino-ethyl)-5-(4-amino-phenyl)-2H-pyrazol-3-yl]-amide, 2-isopropyl-5-methyl-cyclohexane carboxylic acid-[2-(2-amino-ethyl)-5-(4-hydroxy-phenyl)-2H-pyrazol-3-yl]-amide, 2-isopropyl-5-methyl-cyclohexane carboxylic acid-[2-(2-methylamino-ethyl)-5-phenyl-2H-pyrazol-3-yl]-amide, 2-isopropyl-5-methyl-cyclohexane carboxylic acid-[2-(2-amino-propyl)-5-phenyl-2H-pyrazol-3-yl]-amide, 2-isopropyl-5-methyl-cyclohexane carboxylic acid-[, 2-(2- amino-ethyl)-5-(3-cyano-phenyl)-2H-pyrazol-3-yl]-amide, 2-isopropyl-5-methyl-cyclohexane carboxylic acid-[2-(2-amino-ethyl)-5-(3-methoxy-phenyl)-2H-pyrazol-3-yl]-amide, 2-isopropyl-5-methyl-cyclohexane carboxylic acid-[4-{1-(2-amino-ethyl)-1H-pyrazol-3-yl}-benzoic acid methyl ester]-amide, 2-isopropyl-5-methyl-cyclohexane carboxylic acid-[2-(2-amino-ethyl)-5-(3-amino-phenyl)-2H-pyrazol-3-yl]-amide, 2-isopropyl-5-methyl-cyclohexane carboxylic acid-[2-(2-amino-ethyl)-5-(3-hydroxy-phenyl)-2H-pyrazol-3-yl]-amide or a pharmaceutically acceptable salt thereof.

9. The compound of claim 8 in isolated or purified form.

10. A pharmaceutical composition comprising a compound of claim 1, and combinations thereof, or a pharmaceutically acceptable salt thereof, and a pharmaceutically acceptable excipient.

* * * * *

SEQUENCE LISTING

<160> NUMBER OF SEQ ID NOS: 2

<210> SEQ ID NO 1
<211> LENGTH: 5674
<212> TYPE: DNA
<213> ORGANISM: Homo sapiens
<220> FEATURE:
<223> OTHER INFORMATION: human transient receptor potential-p8 (Trp-p8)
      cation channel protein

<400> SEQUENCE: 1

| | | | | | |
|---|---|---|---|---|---|
| aagaaaatcc | tgcttgacaa | aaaccgtcac | ttaggaaaag | atgtcctttc | gggcagccag | 60 |
| gctcagcatg | aggaacagaa | ggaatgacac | tctggacagc | acccggaccc | tgtactccag | 120 |
| cgcgtctcgg | agcacagact | tgtcttacag | tgaaagcgac | ttggtgaatt | ttattcaagc | 180 |
| aaattttaag | aaacgagaat | gtgtcttctt | tatcaaagat | tccaaggcca | cggagaatgt | 240 |
| gtgcaagtgt | ggctatgccc | agagccagca | catgaaggc | acccagatca | accaaagtga | 300 |
| gaaatggaac | tacaagaaac | acaccaagga | atttcctacc | gacgcctttg | gggatattca | 360 |
| gtttgagaca | ctggggaaga | agggaagta | tatacgtctg | tcctgcgaca | cggacgcgga | 420 |
| aatcctttac | gagctgctga | cccagcactg | gcacctgaaa | acacccaacc | tggtcatttc | 480 |
| tgtgaccggg | ggcgccaaga | acttcgccct | gaagccgcgc | atgcgcaaga | tcttcagccg | 540 |
| gctcatctac | atcgcgcagt | ccaaaggtgc | ttggattctc | acgggaggca | cccattatgg | 600 |
| cctgatgaag | tacatcgggg | aggtggtgag | agataacacc | atcagcagga | gttcagagga | 660 |
| gaatattgtg | ccattggca | tagcagcttg | gggcatggtc | tccaaccggg | acaccctcat | 720 |
| caggaattgc | gatgctgagg | ctatttttt | agcccagtac | cttatggatg | acttcacaag | 780 |
| agatccactg | tatatcctgg | acaacaacca | cacacatttg | ctgctcgtgg | acaatggctg | 840 |
| tcatggacat | cccactgtcg | aagcaaagct | ccggaatcag | ctagagaagt | atatctctga | 900 |
| gcgcactatt | caagattcca | actatggtgg | caagatcccc | attgtgtgtt | ttgcccaagg | 960 |
| aggtggaaaa | gagactttga | agccatcaa | tacctccatc | aaaaataaaa | ttccttgtgt | 1020 |
| ggtggtggaa | ggctcgggcc | agatcgctga | tgtgatcgct | agcctggtgg | aggtggagga | 1080 |
| tgccctgaca | tcttctgccg | tcaaggagaa | gctggtgcgc | ttttacccc | gcacggtgtc | 1140 |
| ccggctgcct | gaggaggaga | ctgagagttg | gatcaaatgg | ctcaaagaaa | ttctcgaatg | 1200 |
| ttctcaccta | ttaacagtta | ttaaaatgga | agaagctggg | gatgaaattg | tgagcaatgc | 1260 |
| catctcctac | gctctataca | aagccttcag | caccagtgag | caagacaagg | ataactggaa | 1320 |
| tgggcagctg | aagcttctgc | tggagtggaa | ccagctggac | ttagccaatg | atgagatttt | 1380 |
| caccaatgac | cgccgatggg | agtctgctga | ccttcaagaa | gtcatgttta | cggctctcat | 1440 |
| aaaggacaga | cccaagtttg | tccgcctctt | tctggagaat | ggcttgaacc | tacgaagtt | 1500 |
| tctcacccat | gatgtcctca | ctgaactctt | ctccaaccac | ttcagcacgc | ttgtgtaccg | 1560 |
| gaatctgcag | atcgccaaga | attcctataa | tgatgccctc | ctcacgtttg | tctgaaaact | 1620 |
| ggttgcgaac | ttccgaagag | gcttccggaa | ggaagacaga | aatggccggg | acgagatgga | 1680 |
| catagaactc | cacgacgtgt | ctcctattac | tcggcacccc | ctgcaagctc | tcttcatctg | 1740 |
| ggccattctt | cagaataaga | aggaactctc | caaagtcatt | tgggagcaga | ccaggggctg | 1800 |
| cactctggca | gccctgggag | ccagcaagct | tctgaagact | ctggccaaag | tgaagaacga | 1860 |
| catcaatgct | gctggggagt | ccgaggagct | ggctaatgag | tacgagaccc | gggctgttga | 1920 |
| gctgttcact | gagtgttaca | gcagcgatga | agacttggca | gaacagctgc | tggtctattc | 1980 |

```
ctgtgaagct tggggtggaa gcaactgtct ggagctggcg gtggaggcca cagaccagca    2040
tttcatcgcc cagcctgggg tccagaattt tctttctaag caatggtatg gagagatttc    2100
ccgagacacc aagaactgga agattatcct gtgtctgttt attatacccct tggtgggctg    2160 tggctttgta tcatttagga agaaacctgt cgacaagcac aagaagctgc tttggtacta    2220
tgtggcgttc ttcacctccc ccttcgtggt cttctcctgg aatgtggtct tctacatcgc    2280
cttcctcctg ctgtttgcct acgtgctgct catggatttc cattcggtgc cacacccccc    2340
cgagctggtc ctgtactcgc tggtcttttgt cctcttctgt gatgaagtga cacagtggta    2400
cgtaaatggg gtgaattatt ttactgacct gtggaatgtg atggacacgc tggggctttt    2460
ttacttcata gcaggaattg tatttcggct ccactcttct aataaaagct ctttgtattc    2520
tggacgagtc attttctgtc tggactacat tattttcact ctaagattga ccacattttt    2580
tactgtaagc agaaacttag acccaagat tataatgctg cagaggatgc tgatcgatgt    2640
gttcttcttc ctgttcctct ttgcggtgtg gatggtggcc tttggcgtgg ccaggcaagg    2700
gatccttagg cagaatgagc agcgctggag gtggatattc cgttcggtca tctacgagcc    2760
ctacctggcc atgttcggcc aggtgcccag tgacgtggat ggtaccacgt atgactttgc    2820
ccactgcacc ttcactggga atgagtccaa gccactgtgt gtggagctgg atgagcacaa    2880
cctgccccgg ttccccgagt ggatcaccat ccccctggtg tgcatctaca tgttatccac    2940
caacatcctg ctggtcaacc tgctggtcgc catgtttggc tacacggtgg gcaccgtcca    3000
ggagaacaat gaccaggtct ggaagttcca gaggtacttc ctggtgcagg agtactgcag    3060
ccgcctcaat atccccttcc ccttcatcgt cttcgcttac ttctacatgg tggtgaagaa    3120
gtgcttcaag tgttgctgca aggagaaaaa catggagtct tctgtctgct gtttcaaaaa    3180
tgaagacaat gagactctgg catgggaggg tgtcatgaag gaaaactacc ttgtcaagat    3240
caacacaaaa gccaacgaca cctcagagga aatgaggcat cgatttagac aactggatac    3300
aaagcttaat gatctcaagg gtcttctgaa agagattgct aataaaatca ataaaatca    3360 aataaaactg tatgaaactc taatggagaa aaatctaatt atagcaagat catattaagg    3420
aatgctgatg aacaattttg ctatcgacta ctaaatgaga gttttcaga ccctgggta    3480 catggtggat gatttttaaat caccctagtg tgctgagacc ttgagaataa agtgtgtgat    3540
tggtttcata cttgaagacg gatataaagg aagaatattt cctttatgtg tttctccaga    3600
atggtgcctg tttctctctg tgtctcaatg cctgggactg gaggttgata gtttaagtgt    3660
gttcttaccg cctccttttt cctttaatct tatttttgat gaacacatat ataggagaac    3720
atctatccta tgaataagaa cctggtcatg ctttactcct gtattgttat tttgttcatt    3780
tccaattgat tctctacttt tcccttttt gtattatgtg actaattagt tggcatattg    3840
ttaaaagtct ctcaaattag gccagattct aaaacatgct gcagcaagag gaccccgctc    3900
tcttcaggaa aagtgttttc atttctcagg atgcttctta cctgtcagag gaggtgacaa    3960
ggcagtctct tgctctcttg gactcaccag gctcctattg aaggaaccac ccccattcct    4020
aaatatgtga aaagtcgccc aaaatgcaac cttgaaaggc actactgact tgttcttat    4080 tggatactcc tcttatttat tattttttcca ttaaaaataa tagctggcta ttatagaaaa    4140
tttagaccat acagagatgt agaaagaaca taaattgtcc ccattacctt aaggtaatca    4200
ctgctaacaa tttctggatg gttttttcaag tctatttttt ttctatgtat gtctcaattc    4260
tctttcaaaa ttttacagaa tgttatcata ctacatatat acttttttatg taagcttttt    4320 cacttagtat tttatcaaat atgtttttat tatattcata gccttcttaa acattatatc    4380
```

-continued

```
aataattgca taataggcaa cctctagcga ttaccataat tttgctcatt gaaggctatc    4440
tccagttgat cattgggatg agcatctttg tgcatgaatc ctattgctgt atttgggaaa    4500
attttccaag gttagattcc aataaatatc tatttattat taaatattaa aatatcgatt    4560
tattattaaa accatttata aggcttttc ataaatgtat agcaaatagg aattattaac     4620
ttgagcataa gatatgagat acatgaacct gaactattaa aataaaatat tatatttaac    4680
cctagtttaa gaagaagtca atatgcttat ttaaatatta tggatggtgg gcagatcact    4740
tgaggtcagg agttcgagac cagcctggcc aacatggcaa aaccacatct ctactaaaaa    4800
taaaaaaatt agctgggtgt ggtggtgcac tcctgtaatc ccagctactc agaaggctga    4860
ggtacaagaa ttgctggaac ctgggaggcg gaggttgcag tgaaccaaga ttgcaccact    4920
gcactccagc cggggtgaca gagtgagact ccgactgaaa ataaataaat aaataaataa    4980
ataaataaat aaataaatat tatgatggt gaagggaatg gtatagaatt ggagagatta     5040
tcttactgaa cacctgtagt cccagctttc tctggaagtg gtggtatttg agcaggatgt    5100
gcacaaggca attgaaatgc ccataattag tttctcagct ttgaatacac tataaactca    5160
gtggctgaag gaggaaattt tagaaggaag ctactaaaag atctaatttg aaaaactaca    5220
aaagcattaa ctaaaaaagt ttattttcct tttgtctggg cagtagtgaa aataactact    5280
cacaacattc actatgtttg caaggaatta acacaaataa aagatgcctt tttacttaaa    5340
cgccaagaca gaaaacttgc ccaatactga gaagcaactt gcattagaga gggaactgtt    5400
aaatgttttc aacccagttc atctggtgga tgttttttgca ggttactctg agaatttgc    5460 ttatgaaaaa tcattatttt tagtgtagtt cacaataatg tattgaacat acttctaatc    5520
aaaggtgcta tgtccttgtg tatggtacta aatgtgtcct gtgtacttt gcacaactga     5580 gaatcctgcg gcttggttta atgagtgtgt tcatgaaata aataatggag gaattgtcaa    5640
aaaaaaaaaa aaaaaaaaaa aaaaaaaaaa aaaa                                5674
```

<210> SEQ ID NO 2
<211> LENGTH: 1104
<212> TYPE: PRT
<213> ORGANISM: Homo sapiens
<220> FEATURE:
<223> OTHER INFORMATION: human transient receptor potential-p8 (Trp-p8) cation channel protein

<400> SEQUENCE: 2

```
Met Ser Phe Arg Ala Ala Arg Leu Ser Met Arg Asn Arg Arg Asn Asp
 1               5                   10                  15

Thr Leu Asp Ser Thr Arg Thr Leu Tyr Ser Ser Ala Ser Arg Ser Thr
            20                  25                  30

Asp Leu Ser Tyr Ser Glu Ser Asp Leu Val Asn Phe Ile Gln Ala Asn
        35                  40                  45

Phe Lys Lys Arg Glu Cys Val Phe Phe Ile Lys Asp Ser Lys Ala Thr
    50                  55                  60

Glu Asn Val Cys Lys Cys Gly Tyr Ala Gln Ser Gln His Met Glu Gly
65                  70                  75                  80

Thr Gln Ile Asn Gln Ser Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125
```

-continued

```
Leu Tyr Glu Leu Leu Thr Gln His Trp His Leu Lys Thr Pro Asn Leu
    130                 135                 140
Val Ile Ser Val Thr Gly Gly Ala Lys Asn Phe Ala Leu Lys Pro Arg
145                 150                 155                 160
Met Arg Lys Ile Phe Ser Arg Leu Ile Tyr Ile Ala Gln Ser Lys Gly
                165                 170                 175
Ala Trp Ile Leu Thr Gly Gly Thr His Tyr Gly Leu Met Lys Tyr Ile
            180                 185                 190
Gly Glu Val Val Arg Asp Asn Thr Ile Ser Arg Ser Ser Glu Glu Asn
        195                 200                 205
Ile Val Ala Ile Gly Ile Ala Ala Trp Gly Met Val Ser Asn Arg Asp
210                 215                 220
Thr Leu Ile Arg Asn Cys Asp Ala Glu Gly Tyr Phe Leu Ala Gln Tyr
225                 230                 235                 240
Leu Met Asp Asp Phe Thr Arg Asp Pro Leu Tyr Ile Leu Asp Asn Asn
                245                 250                 255
His Thr His Leu Leu Val Asp Asn Gly Cys His Gly His Pro Thr
            260                 265                 270
Val Glu Ala Lys Leu Arg Asn Gln Leu Glu Lys Tyr Ile Ser Glu Arg
        275                 280                 285
Thr Ile Gln Asp Ser Asn Tyr Gly Gly Lys Ile Pro Ile Val Cys Phe
290                 295                 300
Ala Gln Gly Gly Gly Lys Glu Thr Leu Lys Ala Ile Asn Thr Ser Ile
305                 310                 315                 320
Lys Asn Lys Ile Pro Cys Val Val Val Glu Gly Ser Gly Gln Ile Ala
                325                 330                 335
Asp Val Ile Ala Ser Leu Val Glu Val Glu Asp Ala Leu Thr Ser Ser
            340                 345                 350
Ala Val Lys Glu Lys Leu Val Arg Phe Leu Pro Arg Thr Val Ser Arg
        355                 360                 365
Leu Pro Glu Glu Glu Thr Glu Ser Trp Ile Lys Trp Leu Lys Glu Ile
370                 375                 380
Leu Glu Cys Ser His Leu Leu Thr Val Ile Lys Met Glu Glu Ala Gly
385                 390                 395                 400
Asp Glu Ile Val Ser Asn Ala Ile Ser Tyr Ala Leu Tyr Lys Ala Phe
                405                 410                 415
Ser Thr Ser Glu Gln Asp Lys Asp Asn Trp Asn Gly Gln Leu Lys Leu
            420                 425                 430
Leu Leu Glu Trp Asn Gln Leu Asp Leu Ala Asn Asp Glu Ile Phe Thr
        435                 440                 445
Asn Asp Arg Arg Trp Glu Ser Ala Asp Leu Gln Glu Val Met Phe Thr
450                 455                 460
Ala Leu Ile Lys Asp Arg Pro Lys Phe Val Arg Leu Phe Leu Glu Asn
465                 470                 475                 480
Gly Leu Asn Leu Arg Lys Phe Leu Thr His Asp Val Leu Thr Glu Leu
                485                 490                 495
Phe Ser Asn His Phe Ser Thr Leu Val Tyr Arg Asn Leu Gln Ile Ala
            500                 505                 510
Lys Asn Ser Tyr Asn Asp Ala Leu Leu Thr Phe Val Trp Lys Leu Val
        515                 520                 525
Ala Asn Phe Arg Arg Gly Phe Arg Lys Glu Asp Arg Asn Gly Arg Asp
530                 535                 540
Glu Met Asp Ile Glu Leu His Asp Val Ser Pro Ile Thr Arg His Pro
545                 550                 555                 560
```

```
Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
                580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Ser Asn Cys
                645                 650                 655

Leu Glu Leu Ala Val Glu Ala Thr Asp Gln His Phe Ile Ala Gln Pro
                660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
                740                 745                 750

Ala Tyr Val Leu Leu Met Asp Phe His Ser Val Pro His Pro Pro Glu
                755                 760                 765

Leu Val Leu Tyr Ser Leu Val Phe Val Leu Phe Cys Asp Glu Val Arg
                770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
                820                 825                 830

Cys Leu Asp Tyr Ile Ile Phe Thr Leu Arg Leu Ile His Ile Phe Thr
                835                 840                 845

Val Ser Arg Asn Leu Gly Pro Lys Ile Ile Met Leu Gln Arg Met Leu
850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
                900                 905                 910

Gly Gln Val Pro Ser Asp Val Asp Gly Thr Thr Tyr Asp Phe Ala His
                915                 920                 925

Cys Thr Phe Thr Gly Asn Glu Ser Lys Pro Leu Cys Val Glu Leu Asp
            930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
```

```
                  980              985              990
Val Trp Lys Phe Gln Arg Tyr Phe Leu Val Gln Glu Tyr Cys Ser Arg
            995                  1000             1005

Leu Asn Ile Pro Phe Pro Phe Ile Val Phe Ala Tyr Phe Tyr Met Val
        1010             1015             1020

Val Lys Lys Cys Phe Lys Cys Cys Lys Glu Lys Asn Met Glu Ser
1025            1030             1035                 1040

Ser Val Cys Cys Phe Lys Asn Glu Asp Asn Glu Thr Leu Ala Trp Glu
                1045             1050             1055

Gly Val Met Lys Glu Asn Tyr Leu Val Lys Ile Asn Thr Lys Ala Asn
            1060             1065             1070

Asp Thr Ser Glu Glu Met Arg His Arg Phe Arg Gln Leu Asp Thr Lys
        1075             1080             1085

Leu Asn Asp Leu Lys Gly Leu Leu Lys Glu Ile Ala Asn Lys Ile Lys
        1090             1095             1100
```